(12) United States Patent  
Suzuki et al.

(10) Patent No.: US 10,501,416 B2  
(45) Date of Patent: Dec. 10, 2019

(54) CATIONIC LIPID

(71) Applicant: EISAI R&D MANAGEMENT CO., LTD., Tokyo (JP)

(72) Inventors: Yuta Suzuki, Ibaraki (JP); Yoshinori Takahashi, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/307,202

(22) PCT Filed: Jun. 22, 2017

(86) PCT No.: PCT/JP2017/023051  
§ 371 (c)(1),  
(2) Date: Dec. 5, 2018

(87) PCT Pub. No.: WO2017/222016  
PCT Pub. Date: Dec. 28, 2017

(65) Prior Publication Data  
US 2019/0218180 A1    Jul. 18, 2019

(30) Foreign Application Priority Data  
Jun. 24, 2016  (JP) ................................. 2016-125925

(51) Int. Cl.  
*C07D 211/62*    (2006.01)  
*C07D 209/52*    (2006.01)  
(Continued)

(52) U.S. Cl.  
CPC ........ *C07D 211/62* (2013.01); *A61K 31/7105* (2013.01); *A61K 47/18* (2013.01);  
(Continued)

(58) Field of Classification Search  
CPC .. C07D 211/62; C07D 209/52; C07D 241/04; A61K 47/10; A61K 47/22; A61K 47/28  
See application file for complete search history.

(56) References Cited

U.S. PATENT DOCUMENTS

| 8,158,601 B2 | 4/2012 | Chen et al. |
| 9,873,669 B2 | 1/2018 | Suzuki et al. |

(Continued)

FOREIGN PATENT DOCUMENTS

| CN | 103167866 | 6/2013 |
| JP | 2012-530059 | 11/2012 |

(Continued)

OTHER PUBLICATIONS

Written Opinion in International Application No. PCT/JP2017/023051, dated Sep. 5, 2017, 9 pages (with English Translation).

(Continued)

*Primary Examiner* — Timothy R Rozof  
(74) *Attorney, Agent, or Firm* — Fish & Richardson P.C.

(57) ABSTRACT

The present invention provides a cationic lipid which is able to be used for nucleic acid delivery to the cytoplasm. A cationic lipid according to the present invention is, for example, a compound represented by formula (1a) or a pharmaceutically acceptable salt thereof. (In formula (1a), each of $L_1$ and $L_2$ independently represent an alkylene group having 3-10 carbon atoms; each of $R_1$ and $R_2$ independently represent an alkyl group having 4-22 carbon atoms or an alkenyl group having 4-22 carbon atoms; $X_1$ represents a single bond or —CO—O—; and ring P represents one of formulae (P-1) to (P-5).) (In formulae (P-1) to (P-5), $R_3$ represents an alkyl group having 1-3 carbon atoms.)

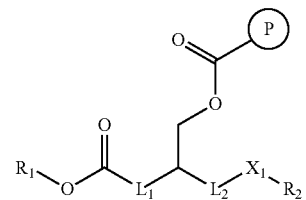

(1a)

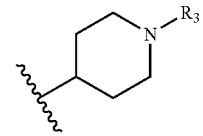

(P-1)

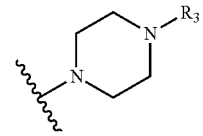

(P-2)

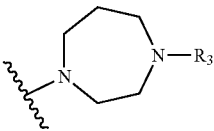

(P-3)

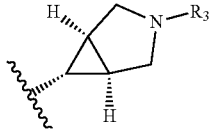

(P-4)

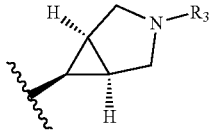

(P-5)

15 Claims, 1 Drawing Sheet  
Specification includes a Sequence Listing.

(51) Int. Cl.
| | |
|---|---|
| *C07D 241/04* | (2006.01) |
| *A61K 47/10* | (2017.01) |
| *A61K 47/22* | (2006.01) |
| *A61K 47/28* | (2006.01) |
| *A61K 47/44* | (2017.01) |
| *A61P 43/00* | (2006.01) |
| *A61K 47/18* | (2017.01) |
| *C07D 211/36* | (2006.01) |
| *A61K 31/7105* | (2006.01) |

(52) U.S. Cl.
CPC ............ *A61K 47/28* (2013.01); *A61K 47/44* (2013.01); *A61P 43/00* (2018.01); *C07D 209/52* (2013.01); *C07D 211/36* (2013.01); *C07D 241/04* (2013.01); *A61K 47/10* (2013.01); *A61K 47/22* (2013.01)

(56) References Cited

U.S. PATENT DOCUMENTS

| | | |
|---|---|---|
| 2010/0324120 A1 | 12/2010 | Chen et al. |
| 2011/0256175 A1 | 10/2011 | Hope |
| 2012/0027803 A1 | 2/2012 | Manoharan et al. |
| 2012/0183602 A1 | 7/2012 | Chen et al. |
| 2013/0178541 A1 | 7/2013 | Stanton et al. |
| 2013/0195920 A1 | 8/2013 | Maier et al. |
| 2015/0133519 A1 | 5/2015 | Colletti et al. |
| 2015/0166465 A1 | 6/2015 | Chen et al. |
| 2015/0273068 A1 | 10/2015 | Maier et al. |
| 2015/0306039 A1 | 10/2015 | Akinc et al. |
| 2015/0361434 A1 | 12/2015 | Stanton et al. |
| 2016/0009637 A1 | 1/2016 | Manoharan et al. |
| 2016/0317458 A1* | 11/2016 | Brito .................. C07D 319/06 |
| 2016/0326116 A1 | 11/2016 | Suzuki et al. |
| 2016/0367638 A1 | 12/2016 | Byers et al. |
| 2017/0135962 A1 | 5/2017 | Colletti et al. |
| 2017/0143631 A1 | 5/2017 | Chen et al. |
| 2017/0233734 A1 | 8/2017 | Akinc et al. |
| 2017/0334852 A1 | 11/2017 | Suzuki et al. |
| 2018/0193279 A1 | 7/2018 | Colletti et al. |

FOREIGN PATENT DOCUMENTS

| | | |
|---|---|---|
| JP | 2013-533224 | 8/2013 |
| WO | 2010/042877 | 4/2010 |
| WO | WO 2010/144740 | 12/2010 |
| WO | WO 2011/153493 | 12/2011 |
| WO | 2012/040184 | 3/2012 |
| WO | 2012/061259 | 5/2012 |
| WO | 2013/059496 | 4/2013 |
| WO | WO 2013/086354 | 6/2013 |
| WO | WO 2013/158579 | 10/2013 |
| WO | WO 2014/089239 | 6/2014 |
| WO | 2015/095351 | 6/2015 |
| WO | WO 2015/095346 | 6/2015 |
| WO | 2015/105131 | 7/2015 |
| WO | 2016/104580 | 6/2016 |

OTHER PUBLICATIONS

International Search Report of in International Application No. PCT/JP2017/023051, dated Sep. 5, 2017, 4 pages (with English translation).
Extended European Search Report in European Patent Application No. 15873148.9, dated May 4, 2018, 7 pages.
International Search Report and Written Opinion in International Application No. PCT/JP2015/085969, dated Mar. 15, 2016, 15 pages (with English Translation).
Suzuki et al., "Biodegradable lipid nanoparticles induce a prolonged RNA interference-mediated protein knockdown and show rapid hepatic clearance in mice and nonhuman primates", International Journal of Pharmaceutics, vol. 519, No. 1-2, Jan. 9, 2017, pp. 34-43.
Chinese Office Action in Chinese Application No. 201580003735.2, dated May 27, 2017, 10 pages (with English Translation).
Communication from the European Patent Office for corresponding European Patent Application No. 15735252.7, dated Jul. 12, 2018, 70 pages.
Decision to Grant a Patent for corresponding Japanese Patent No. 2015-556822, dated Jul. 31, 2018, 6 pages (with English Translation).
Decision to Grant a Patent for corresponding Japanese Patent No. 2016-566429, dated Sep. 3, 2019, 6 pages (with English Translation).
European Search Report in European Application No. 15735252.7, dated Jun. 8, 2017, 6 pages.
Gindy, M.E. et al., "Stabilization of Ostwald Ripening in Low Molecular Weight Amino Lipid Nanoparticles for Systemic Delivery of siRNA Therapeutics", Mal. Pharmaceutics (2014), 11: 4143-4153.
Intention to Grant in European Patent Application No. 15873148.9. dated Oct. 19, 2018, 99 pages.
International Search Report and Written Opinion in International Application No. PCT/JP2018/047440, dated Feb. 19, 2019, 16 pages (with English Translation).
International Search Report issued in International Application No. PCT/JP2015/050295, dated Feb. 17, 2015, 5 pages (with English Translation).
Jayaraman, M. et al., "Maximizing the Potency of siRNA Lipid Nanoparticles for Hepatic Gene Silencing in Vivo", Angew. Chem. Int. Ed. (2012), 51:8529-8533.
Notice of Allowance in U.S. Appl. No. 15/109,512, dated Sep. 18, 2017, 7 pages.
Notice of Allowance in U.S. Appl. No. 15/841,652, dated Oct. 1, 2018, 10 pages.
Office Action in Chinese Patent Application No. 201580003735.2, dated Dec. 21, 2017, 6 pages (with English Translation).
Office Action in Chinese Patent Application No. 201580068712.X, dated Sep. 6, 2018, 13 pages (with English Translation).
Office Action in Japanese Patent Application No. 2016-566429, dated Apr. 23, 2019, 6 pages (with English Translation).
Office Action in U.S. Appl. No. 15/109,512, dated May 19, 2017, 34 pages.
Office Action in U.S. Appl. No. 15/841,652, dated May 18, 2018, 8 pages.
Office Action issued for Taiwanese Patent Application No. 104100437, dated Aug. 31, 2018, 6 pages (with English Translation).
Official Notification to Grant in Chinese Patent Application No. 201580068712.X, dated Mar. 12, 2019, 4 pages (with English Translation).
Official Notification to Grant in Taiwanese Patent Application No. 104100437, dated Nov. 27, 2018, 6 pages (with English Translation).
Response to Restriction Requirement filed in U.S. Appl. No. 15/841,652, dated Mar. 22, 2018, 3 pages.
Response filed in Chinese Patent Application No. 201580003735.2, dated Feb. 28, 2018, 10 pages (with English Translation).
Response filed in Chinese Patent Application No. 201580003735.2, dated Sep. 25, 2017, 5 pages (with English Translation).
Response filed in Chinese Patent Application No. 201580068712.X, dated Nov. 14, 2018, 27 pages (with English Translation).
Response filed in European Patent Application No. 15873148.9, dated Aug. 17, 2018, 93 pages.
Response filed in Japanese Patent Application No. 2016-566429, dated Aug. 9, 2019, 12 pages (with English Translation).
Response filed in Taiwanese Patent Application No. 104100437, dated Nov. 16, 2018, 16 pages (with English Translation).
Response to Office Action in U.S. Appl. No. 15/841,652, filed Jul. 24, 2018, 3 pages.
Response to Office Action in U.S. Appl. No. 15/109,512, filed Aug. 16, 2017, 10 pages.
Response to Restriction Requirement in U.S. Appl. No. 15/109,512, filed May 10, 2017, 3 pages.
Restriction Requirement in U.S. Appl. No. 15/109,512, filed Mar. 13, 2017, 8 pages.

(56) References Cited

OTHER PUBLICATIONS

Restriction Requirement in U.S. Appl. No. 15/841,652, filed Jan. 30, 2018, 6 pages.
The People's Republic of China State Intellectual Property Office, Notice of Allowance issued on Jul. 10, 2018 for corresponding Chinese Patent Application No. 201580003735.2, 4 pages (with English Translation).
Wan et al., "Lipid nanoparticle delivery systems for siRNA-based therapeutics," Drug Delivery and Translational Research, Spring, Germany, 4(1):74-83 (2013).
Written Opinion of the International Searching Authority issued in International Application No. PCT/JP2015/050295, dated Feb. 17, 2015, 6 pages (with English Translation).
Office Action in Taiwanese Patent Application No. 104143612, dated Oct. 2, 2019, 7 pages (with English Translation).

\* cited by examiner

[Figure 1]
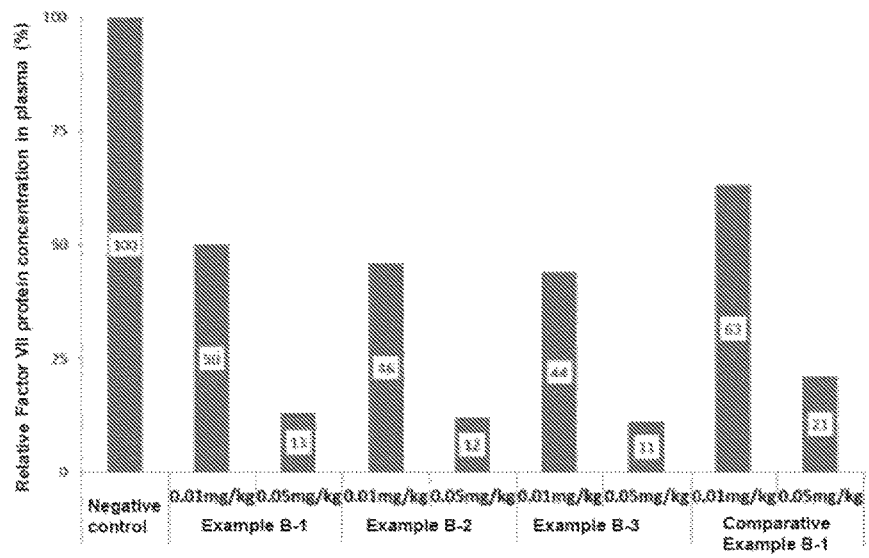
[Figure 2]
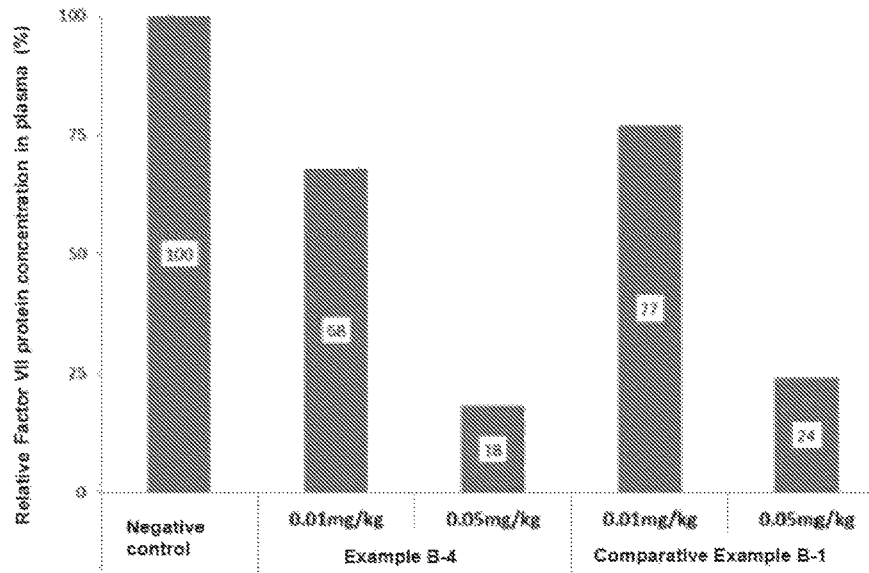

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: #1 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_feature
<222> LOCATION: (4)..(4)
<223> OTHER INFORMATION: n stands for 2'- fluorouridine
<220> FEATURE:
<221> NAME/KEY: misc_feature
<222> LOCATION: (5)..(5)
<223> OTHER INFORMATION: n stands for 2'- fluorocytidine
<220> FEATURE:
<221> NAME/KEY: misc_feature
<222> LOCATION: (7)..(7)
<223> OTHER INFORMATION: n stands for 2'- fluorouridine
<220> FEATURE:
<221> NAME/KEY: misc_feature
<222> LOCATION: (8)..(8)
<223> OTHER INFORMATION: n stands for 2'- fluorocytidine
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (10)..(10)
<223> OTHER INFORMATION: n stands for 2'- fluorocytidine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (15)..(15)
<223> OTHER INFORMATION: n stands for 2'- fluorocytidine
<220> FEATURE:
<221> NAME/KEY: misc_feature
<222> LOCATION: (16)..(16)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (19)..(19)
<223> OTHER INFORMATION: n stands for 2'- fluorocytidine
<220> FEATURE:
<221> NAME/KEY: misc_difference
<222> LOCATION: (20)..(21)
<223> OTHER INFORMATION: DNA
<220> FEATURE:
<221> NAME/KEY: misc_binding
<222> LOCATION: (20)..(21)
<223> OTHER INFORMATION: phosphorothioate binding

<400> SEQUENCE: 1
ggannannnn aagnnnnant t                                              21

<210> SEQ ID NO 2
<211> LENGTH: 21
<212> TYPE: DNA
<213> ORGANISM: Artificial Sequence
<220> FEATURE:
<223> OTHER INFORMATION: #1 antisense
<220> FEATURE:
<221> NAME/KEY: misc_difference

```
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n stands for 2'- fluorouridine
<220> FEATURE:
<221> NAME/KEY: misc_feature
<222> LOCATION: (7)..(7)
<223> OTHER INFORMATION: n stands for 2'- fluorocytidine
<220> FEATURE:
<221> NAME/KEY: misc_feature
<222> LOCATION: (8)..(8)
<223> OTHER INFORMATION: n stands for 2'- fluorouridine
<220> FEATURE:
<221> NAME/KEY: misc_feature
<222> LOCATION: (9)..(9)
<223> OTHER INFORMATION: n stands for 2'- fluorouridine
<220> FEATURE:
<221> NAME/KEY: misc_feature
<222> LOCATION: (14)..(14)
<223> OTHER INFORMATION: n stands for 2'- fluorouridine
<220> FEATURE:
<221> NAME/KEY: misc_feature
<222> LOCATION: (17)..(17)
<223> OTHER INFORMATION: n stands for 2'- fluorouridine
<220> FEATURE:
<221> NAME/KEY: misc_feature
<222> LOCATION: (18)..(18)
<223> OTHER INFORMATION: n stands for 2'- fluorocytidine
<220> FEATURE:
<221> NAME/KEY: misc_feature
<222> LOCATION: (19)..(19)
<223> OTHER INFORMATION: n stands for 2'- fluorocytidine
<220> FEATURE:
<221> NAME/KEY: misc_difference
<222> LOCATION: (20)..(21)
<223> OTHER INFORMATION: DNA
<220> FEATURE:
<221> NAME/KEY: misc_binding
<222> LOCATION: (20)..(21)
<223> OTHER INFORMATION: phosphorothioate binding

<400> SEQUENCE: 2
gnaagannng agangannnt t                                              21

<210> SEQ ID NO 3
<211> LENGTH: 21
<212> TYPE: DNA
<213> ORGANISM: Artificial Sequence
<220> FEATURE:
<223> OTHER INFORMATION: #2 sense
<220> FEATURE:
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA
<220> FEATURE:
<221> NAME/KEY: misc_binding
<222> LOCATION: (20)..(21)
<223> OTHER INFORMATION: phosphorothioate binding

<400> SEQUENCE: 3
cuuacgcuga guacuucgat t                                              21

<210> SEQ ID NO 4
<211> LENGTH: 21
<212> TYPE: DNA
<213> ORGANISM: Artificial Sequence
<220> FEATURE:
<223> OTHER INFORMATION: #2 antisense
<220> FEATURE:
```

```
<221> NAME/KEY: misc_difference
<222> LOCATION: (1)..(19)
<223> OTHER INFORMATION: RNA
<220> FEATURE:
<221> NAME/KEY: misc_difference
<222> LOCATION: (20)..(21)
<223> OTHER INFORMATION: DNA
<220> FEATURE:
<221> NAME/KEY: misc_binding
<222> LOCATION: (20)..(21)
<223> OTHER INFORMATION: phosphorothioate binding

<400> SEQUENCE: 4
ucgaaguacu cagcguaagt t                                              21
```

CATIONIC LIPID

TECHNICAL FIELD

The present invention relates to a novel cationic lipid.

BACKGROUND ART

Nucleic acids such as siRNA (small interfering RNA), miRNA (micro RNA) and shRNA (short hairpin RNA or small hairpin RNA) expression vectors and antisense oligonucleotides induce sequence-specific gene silencing in vivo and are known as oligonucleotide therapeutics.

Among the oligonucleotide therapeutics, siRNAs have attracted particular attention. siRNAs are double-stranded RNAs consisting of 19 to 23 base pairs and induce sequence-specific gene silencing called RNA interference (RNAi).

siRNAs are chemically stable; however, siRNAs have issues in therapeutic applications such as being liable to be decomposed by RNase (ribonuclease) in plasma and being unlikely to pass through the cell membrane alone (for example, see Patent Literature 1).

In order to address the above issues, it has been known that by encapsulating siRNA in a fine particle containing a cationic lipid, the encapsulated siRNA is protected from decomposition in blood plasma and can penetrate a lipophilic cell membrane (for example, see Patent Literature 1).

Patent Literature 2 to 5 disclose cationic lipids where are used for delivery of oligonucleotide therapeutics such as siRNAs and which have improved biodegradability.

Fine particles containing cationic lipids have such an issue of stability that the particles are likely to aggregate during storage, and a method for preventing aggregation by adding polyethylene glycol-modified lipids (PEG lipids) to the fine particles is known.

Further, Patent Literature 6 discloses a method for preventing aggregation and improving a delivery efficiency of nucleic acids by configuring fine particles that comprise a specific PEG lipid, which is PEG-DPG, and a preparation that comprises the fine particles and a deionized solvent.

CITATION LIST

Patent Literature

Patent Literature 1: WO 2010/144740
Patent Literature 2: WO 2011/153493
Patent Literature 3: WO 2013/086354
Patent Literature 4: WO 2013/158579
Patent Literature 5: WO 2015/095346
Patent Literature 6: WO 2014/089239

SUMMARY OF INVENTION

Technical Problem

However, despite recent developments, there is still a need for a cationic lipid that can be used for nucleic acid delivery to the cytoplasm.

Solution to Problem

The present invention relates to [1] to [15] indicated below.

[1] A compound represented by formula (1a) below or a pharmaceutically acceptable salt thereof:

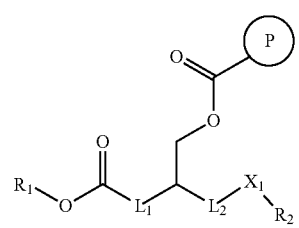

wherein $L_1$ and $L_2$ independently represent an alkylene group having 3 to 10 carbon atoms; $R_1$ and $R_2$ independently represent an alkyl group having 4 to 22 carbon atoms or an alkenyl group having 4 to 22 carbon atoms; $X_1$ represents a single bond or —CO—O—; and the ring P represents any of formulae (P-1) to (P-5) below:

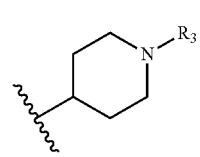

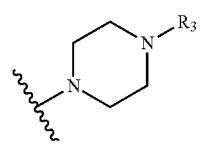

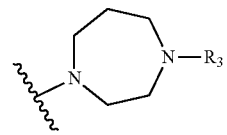

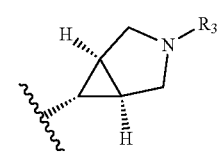

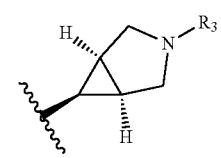

wherein $R_3$ represents an alkyl group having 1 to 3 carbon atoms.

[2] The compound according to [1] represented by formula (1) below, or a pharmaceutically acceptable salt thereof:

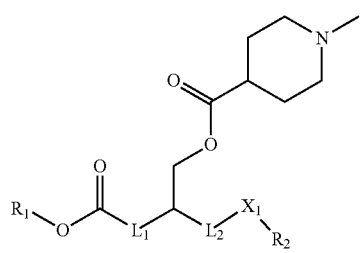

(1)

wherein $L_1$ and $L_2$ independently represent an alkylene group having 3 to 10 carbon atoms; $R_1$ and $R_2$ independently represent an alkyl group having 4 to 22 carbon atoms or an alkenyl group having 4 to 22 carbon atoms; and $X_1$ represents a single bond or —CO—O—.

[3] The compound according to [1] or [2] selected from the group consisting of compounds represented by formulae (A1) to (A22) below, or a pharmaceutically acceptable salt thereof.

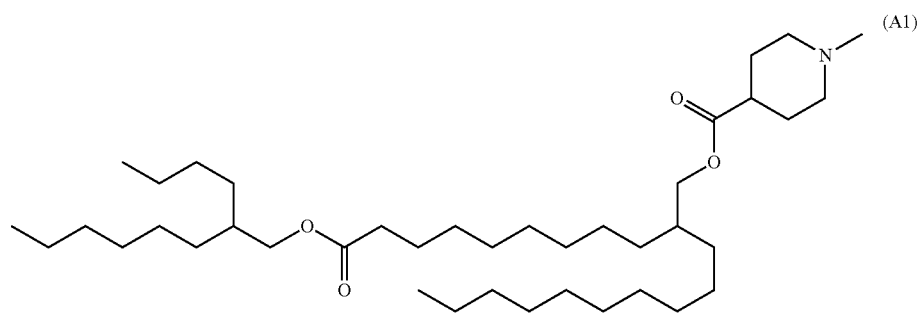

(A1)

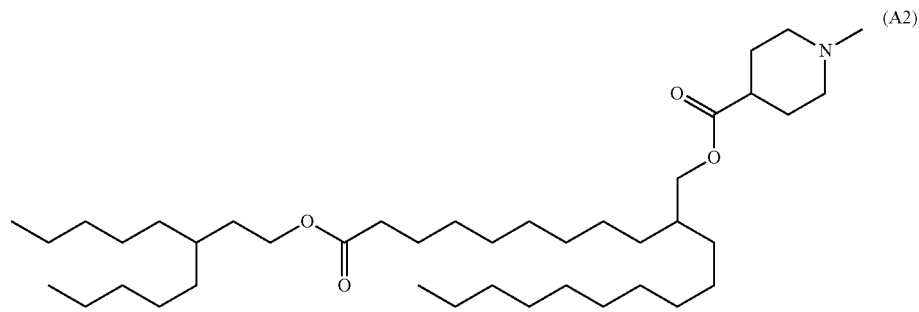

(A2)

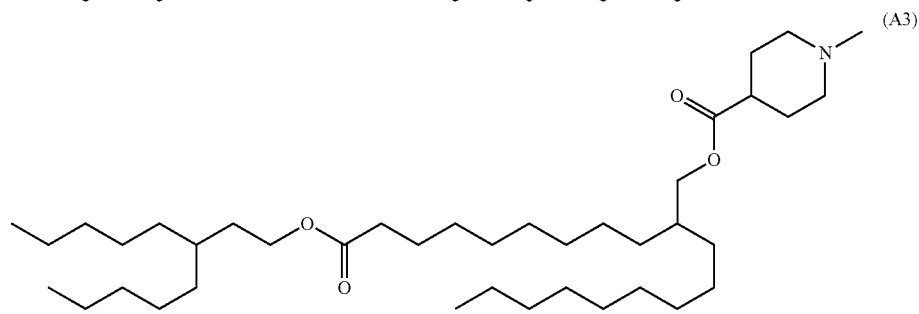

(A3)

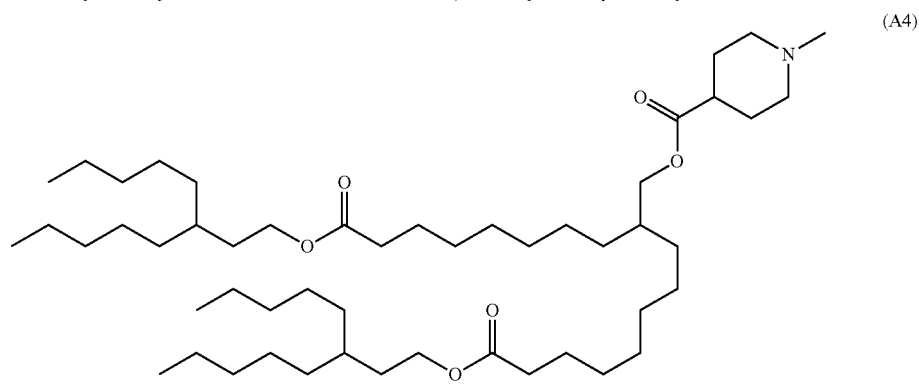

(A4)

-continued
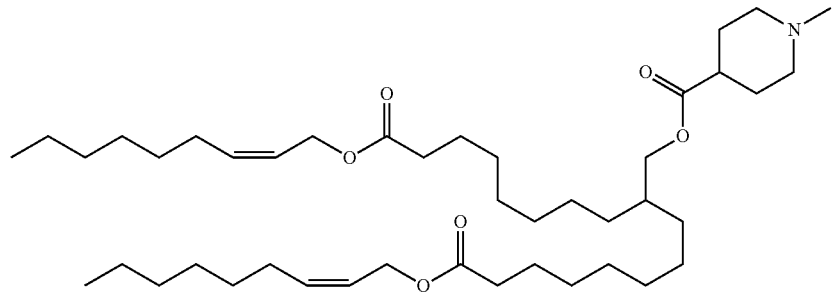
(A5)
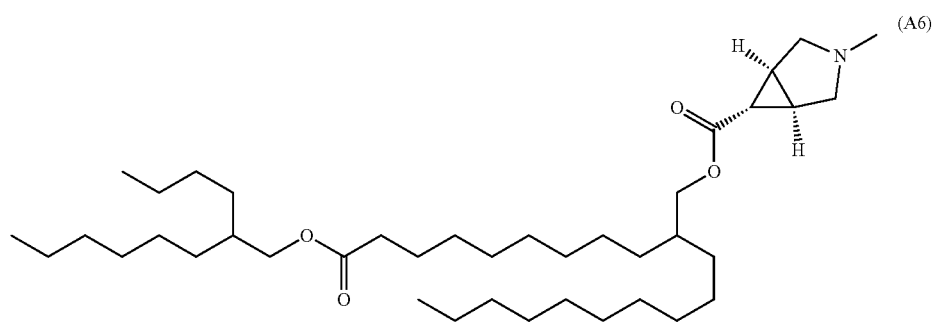
(A6)
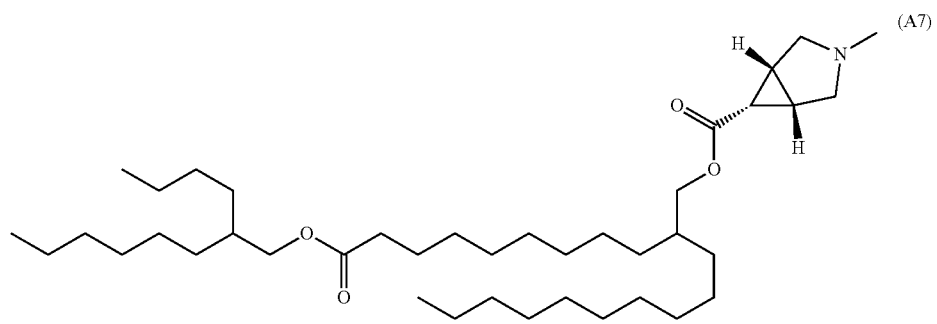
(A7)
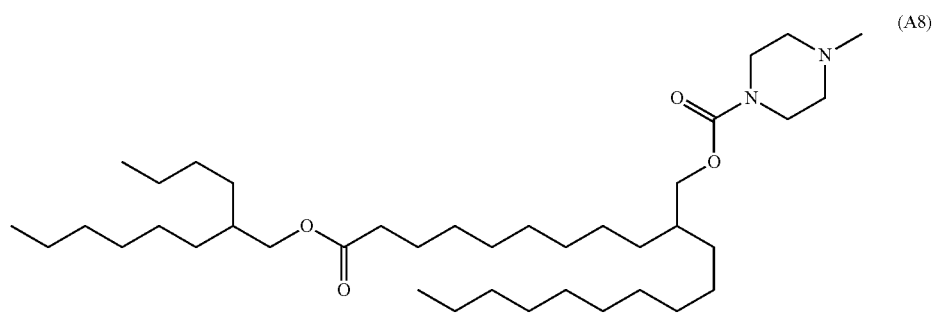
(A8)
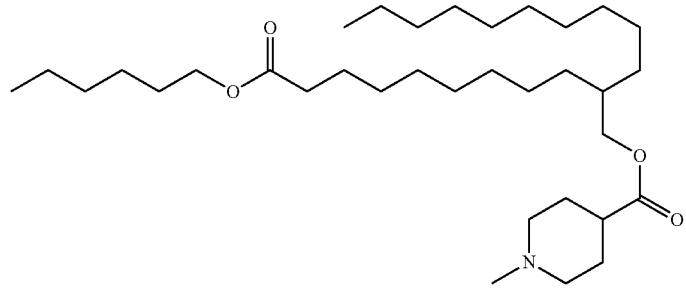
(A9)

-continued
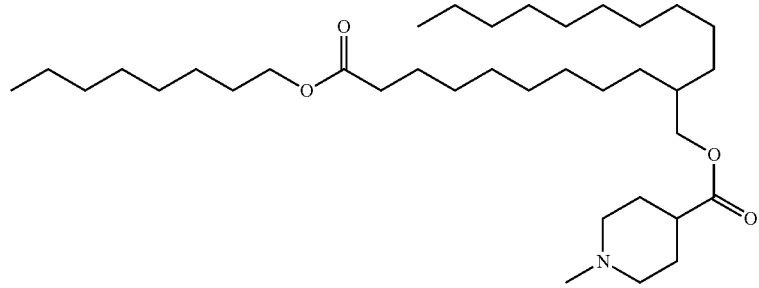
(A10)
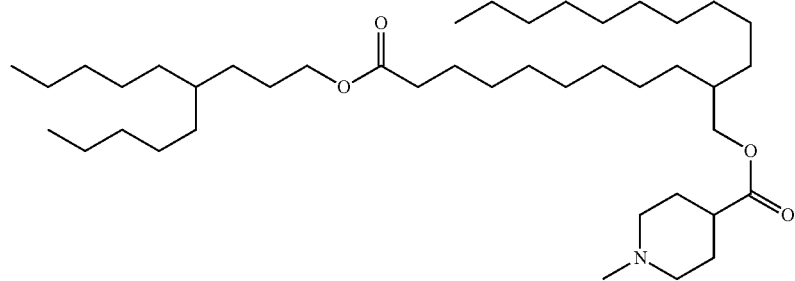
(A11)
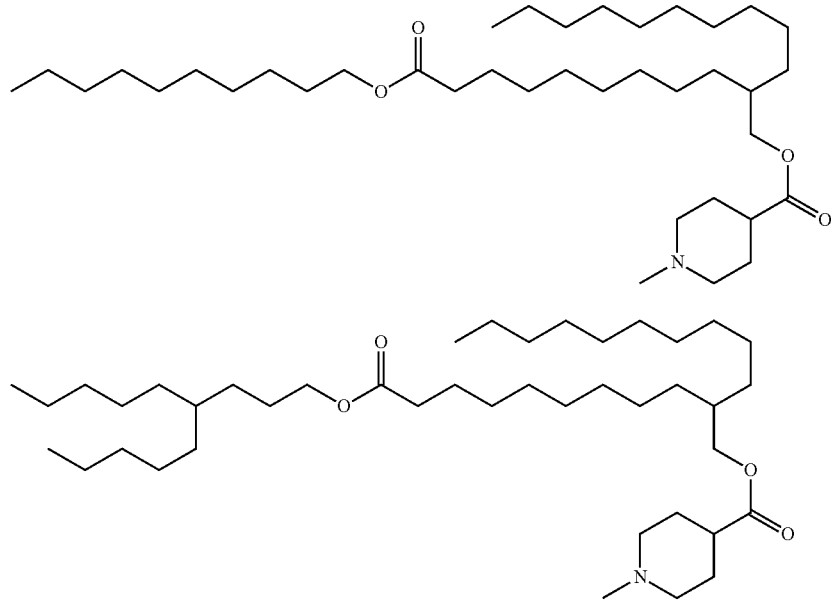
(A12)
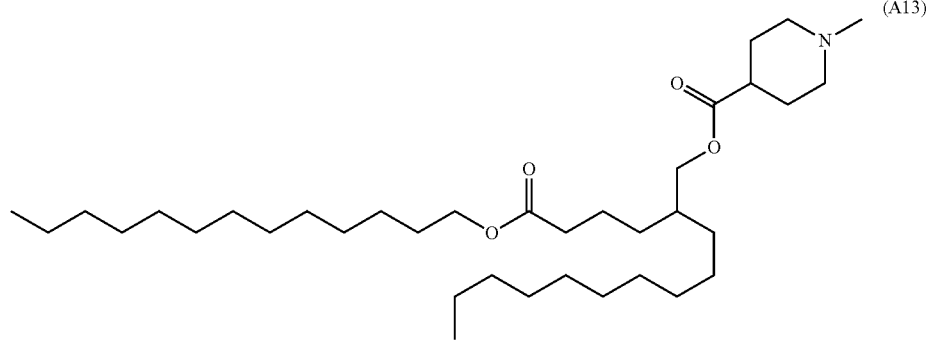
(A13)
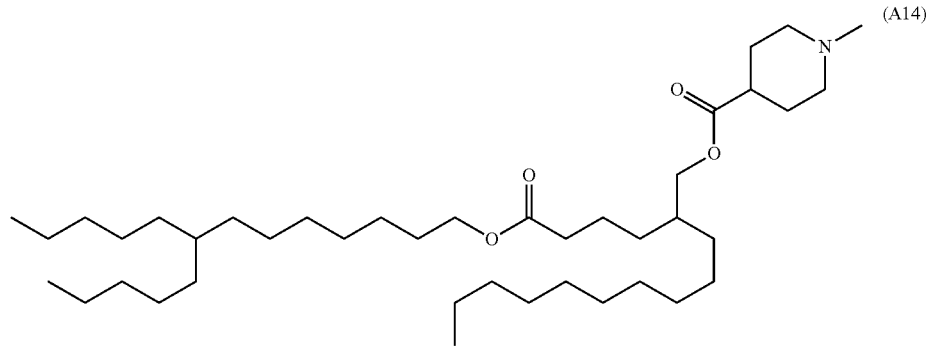
(A14)

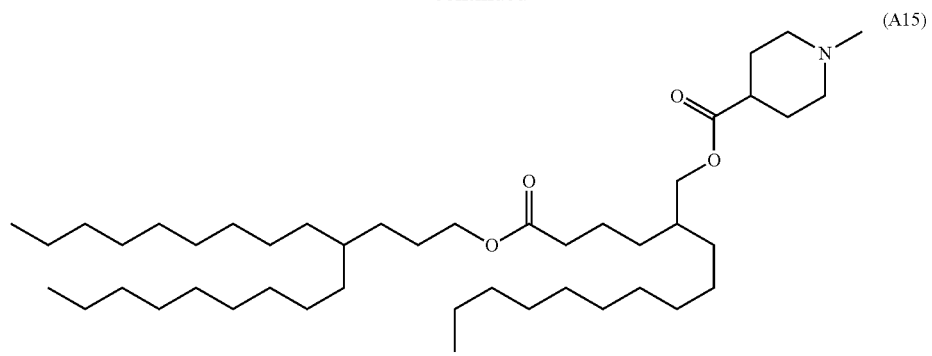
(A15)
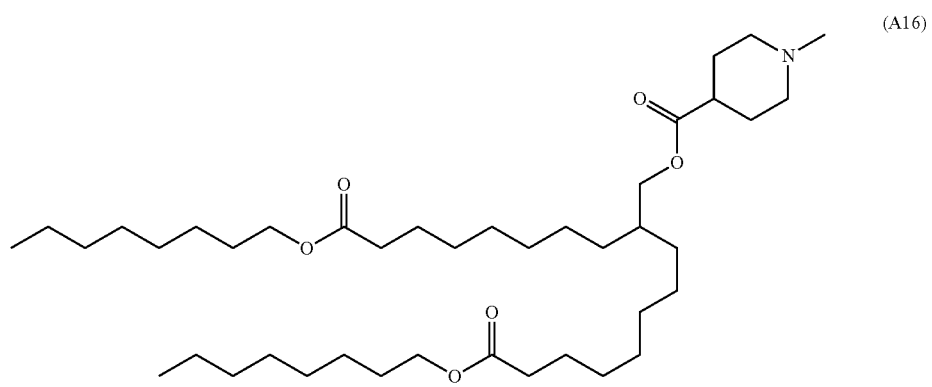
(A16)
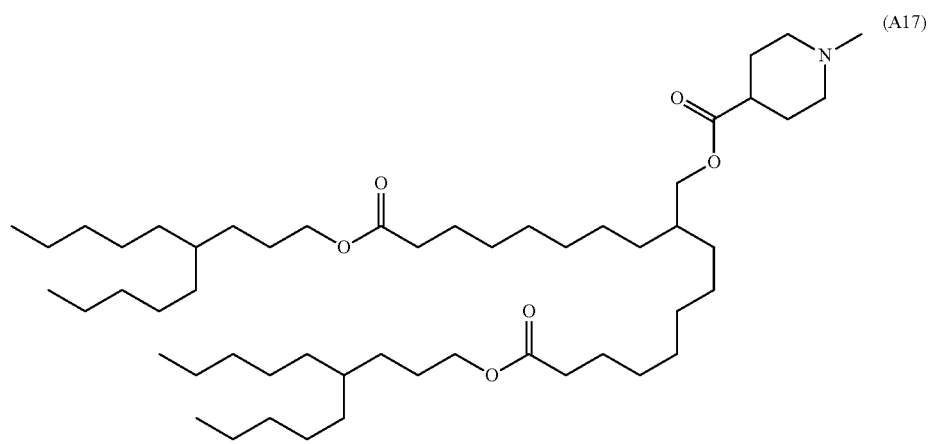
(A17)
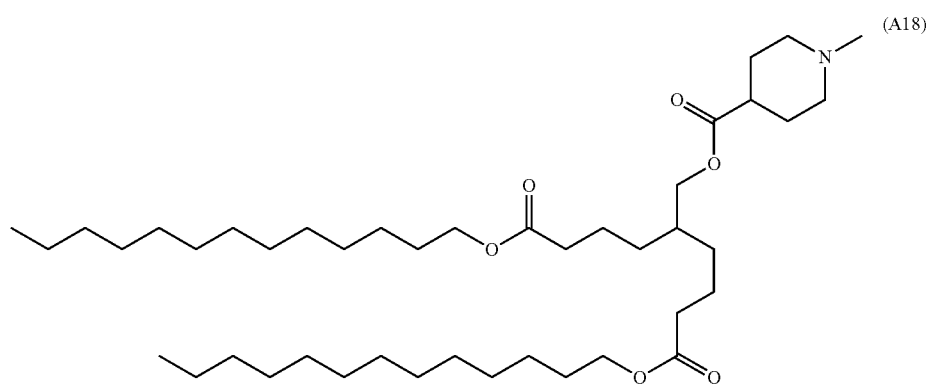
(A18)

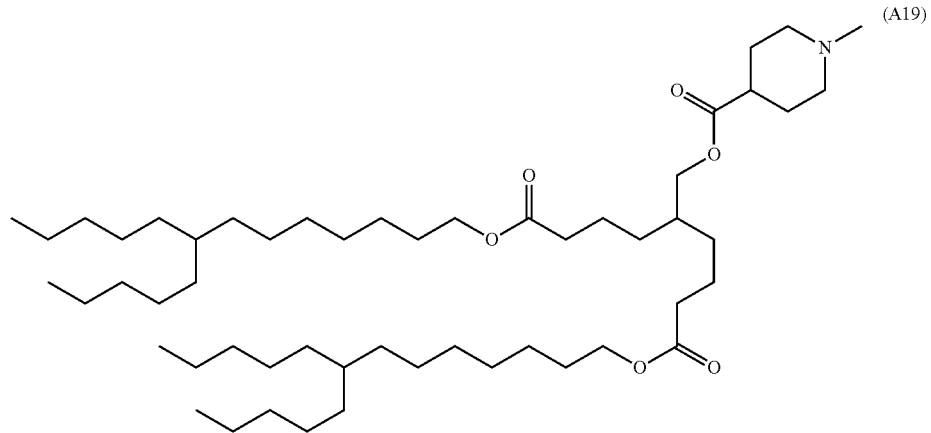
(A19)
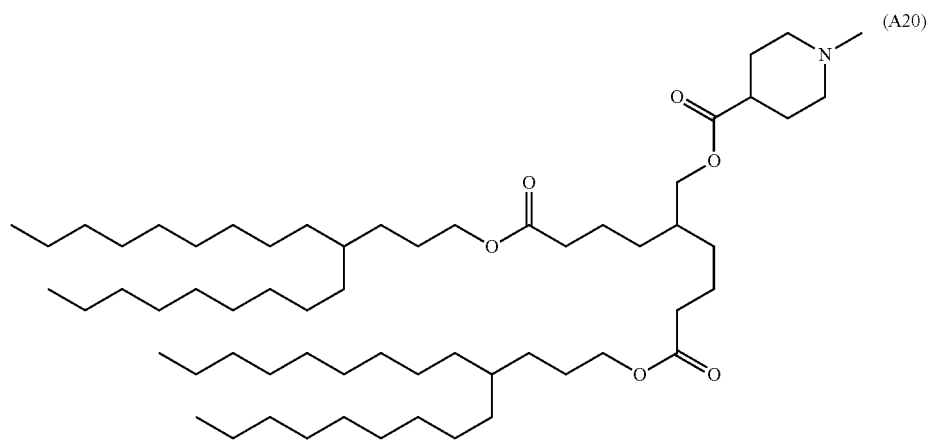
(A20)
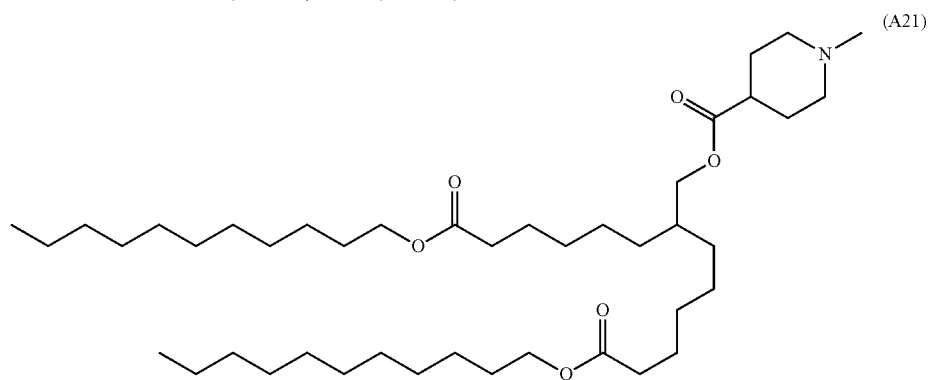
(A21)
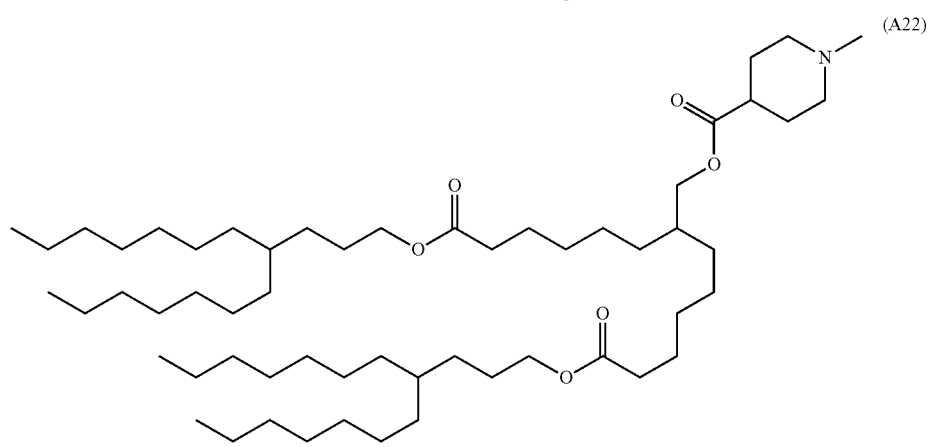
(A22)

[3a] The compound according to [3] selected from the group consisting of compounds represented by formulae (A1), (A2), (A3), (A4), (A5), (A9), (A12), (A15), (A16), (A17), (A19), (A20) and (A22) above, or a pharmaceutically acceptable salt thereof.

[3b] The compound according to [3] selected from the group consisting of compounds represented by formulae (A1), (A2), (A3), (A4), (A5), (A9), (A12), (A15) and (A20) above, or a pharmaceutically acceptable salt thereof.

[3c] The compound according to [3] selected from the group consisting of compounds represented by formulae (A1) to (A5) above, or a pharmaceutically acceptable salt thereof.

[3d] The compound according to [3] selected from the group consisting of compounds represented by formulae (A6) to (A5) above, or a pharmaceutically acceptable salt thereof.

[3] The compound according to any of [1] to [3] represented by formula (A1) below, or a pharmaceutically acceptable salt thereof.

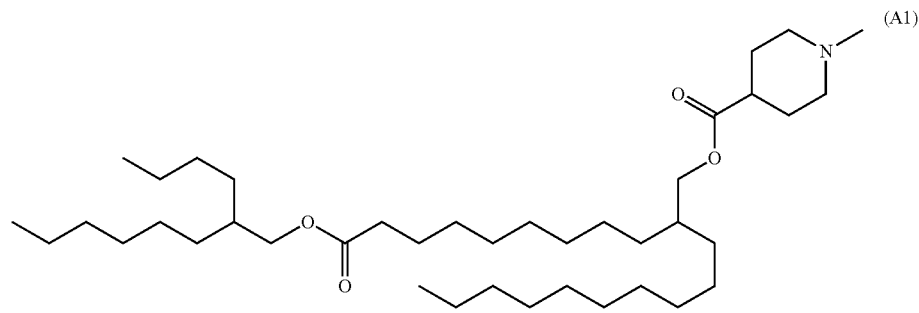 [SMILES: CCCCCCCCCCC(CCCCCCCCC(=O)OCC(CCCC)CCCCCC)COC(=O)C1CCN(C)CC1]

[4] The compound according to any of [1] to [3] represented by formula (A2) below, or a pharmaceutically acceptable salt thereof.

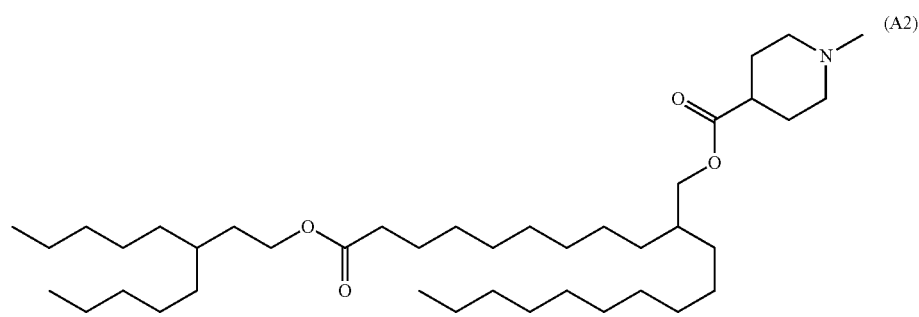 [SMILES: CCCCCCCCCCC(CCCCCCCCC(=O)OCCC(CCCCC)CCCCC)COC(=O)C1CCN(C)CC1]

[5] The compound according to any of [1] to [3] represented by formula (A3) below, or a pharmaceutically acceptable salt thereof.

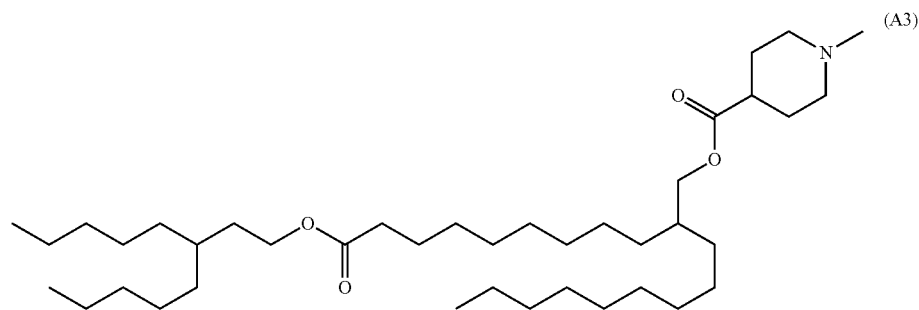 [SMILES: CCCCCCCCCC(CCCCCCCCC(=O)OCCC(CCCCC)CCCCC)COC(=O)C1CCN(C)CC1]

[6] The compound according to any of [1] to [3] represented by formula (A4) below, or a pharmaceutically acceptable salt thereof.

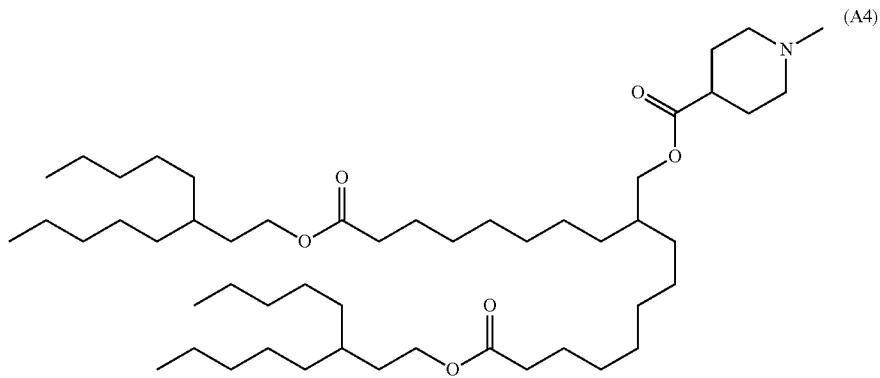 [SMILES: CCCCCC(CCCCC)CCOC(=O)CCCCCCCC(CCCCCCCC(=O)OCCC(CCCCC)CCCCC)COC(=O)C1CCN(C)CC1]

[7] The compound according to any of [1] to [3] represented by formula (A5) below, or a pharmaceutically acceptable salt thereof.

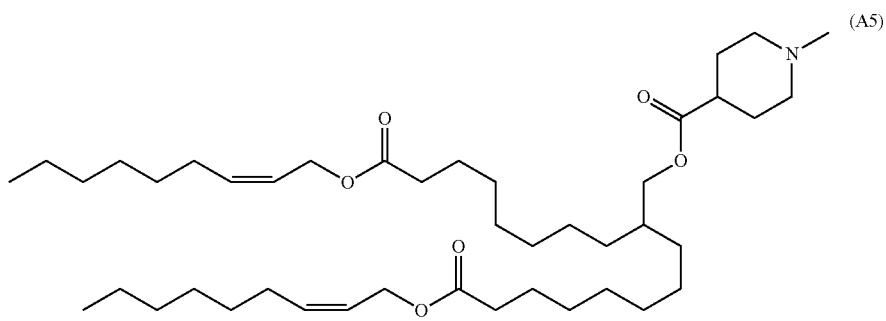 [SMILES: CCCCCC/C=C\COC(=O)CCCCCCCC(CCCCCCCC(=O)OC/C=C\CCCCCC)COC(=O)C1CCN(C)CC1]

[8] The compound according to any of [1] to [3] represented by formula (A9) below, or a pharmaceutically acceptable salt thereof.

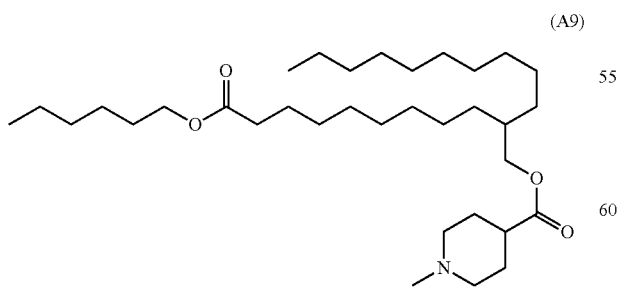

[9] The compound according to any of [1] to [3] represented by formula (A12) below, or a pharmaceutically acceptable salt thereof.

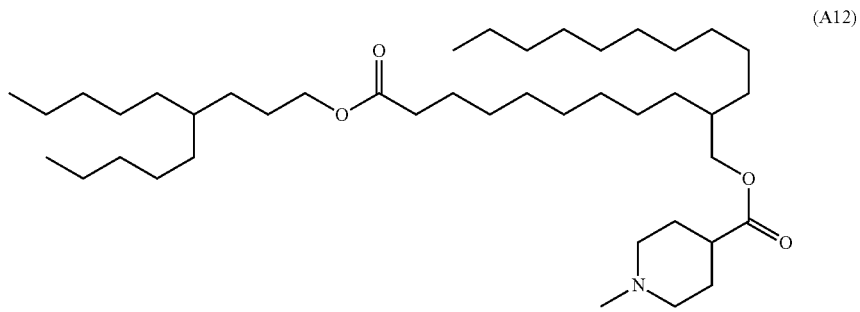 [SMILES: CCCCCCCCCCC(CCCCCCCCC(=O)OCCCC(CCCCC)CCCCC)COC(=O)C1CCN(C)CC1]

(A12)

[10] The compound according to any of [1] to [3] represented by formula (A15) below, or a pharmaceutically acceptable salt thereof.

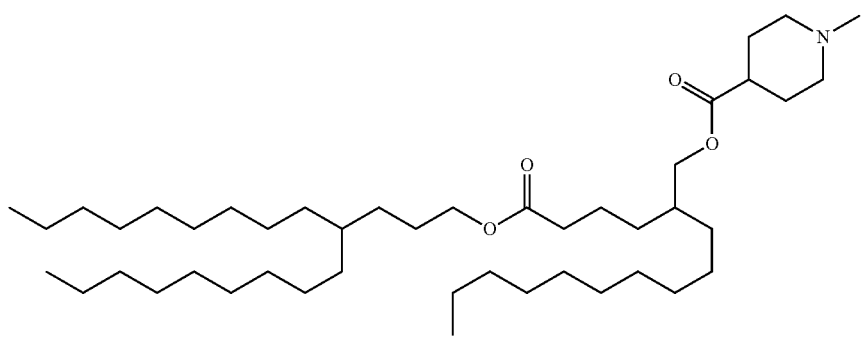 [SMILES: CCCCCCCCCCC(CCCC(=O)OCCCC(CCCCCCCCC)CCCCCCCCC)COC(=O)C1CCN(C)CC1]

[11] The compound according to any of [1] to [3] represented by formula (A20) below, or a pharmaceutically acceptable salt thereof.

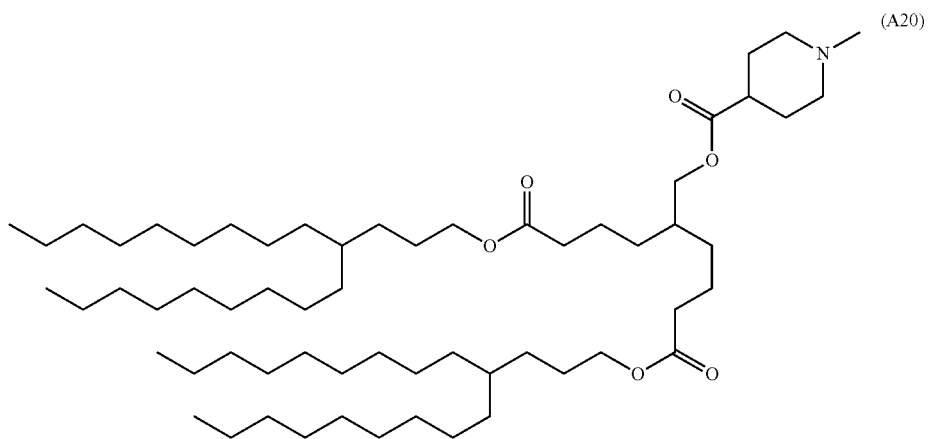 [SMILES: CCCCCCCCCC(CCCCCCCCC)CCCOC(=O)CCCC(CCCC(=O)OCCCC(CCCCCCCCC)CCCCCCCCC)COC(=O)C1CCN(C)CC1]

(A20)

[13] A lipid complex containing: (I) the compound according to any one of [1] to [12] or a pharmaceutically acceptable salt thereof; and (II) at least one lipid selected from the group consisting of a neutral lipid, a polyethylene glycol-modified lipid and a sterol.

[14] A composition containing: (I) the compound according to any one of [1] to [12] or a pharmaceutically acceptable salt thereof; (II) at least one lipid selected from the group consisting of a neutral lipid, a polyethylene glycol-modified lipid and a sterol; and (III) a nucleic acid.

[15] A method for producing a composition, the method including: the step of mixing a polar organic solvent-containing aqueous solution containing (I) the compound according to any one of [1] to [12] or a pharmaceutically acceptable salt thereof, and (II) at least one lipid selected from the group consisting of a neutral lipid, a polyethylene glycol-modified lipid and a sterol with an aqueous solution containing (III) a nucleic acid to obtain a mixed solution; and the step of reducing a content percentage of the polar organic solvent in the mixed solution.

Effect of the Invention

The cationic lipid of the present invention has one or more effects indicated below:

(1) The cationic lipid of the present invention allows effective release of nucleic acids to the cytoplasm;

(2) The cationic lipid of the present invention can prevent an increase in the particle diameter of the lipid complex during the storage over a certain period of time.

Therefore, the cationic lipid of the present invention can be applied as a lipid used to deliver a nucleic acid into the cytoplasm.

BRIEF DESCRIPTION OF DRAWINGS

FIG. 1 is a graph illustrating the result of Test Example 1.
FIG. 2 is a graph illustrating the result of Test Example 2.

DESCRIPTION OF EMBODIMENTS

The present invention is hereinafter described in detail by presenting embodiments and examples. However, the present invention is not limited to the embodiments and examples described below and may be arbitrarily modified and worked within the scope that does not deviate the concept of the present invention. All the documents and publications cited in the present specification are entirely incorporated herein by reference regardless of the purpose thereof.

(Cationic lipid)

In one embodiment, the present invention is a compound represented by formula (1a) below or a pharmaceutically acceptable salt thereof, and may be used as a cationic lipid. The cationic lipid may be a hydrate of the salt or a solvate of the salt.

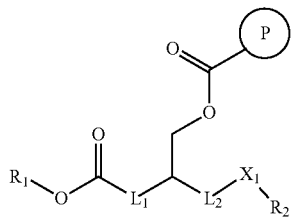

(1a)

In formula (1a), the ring P represents any of formulae (P-1) to (P-5) below.

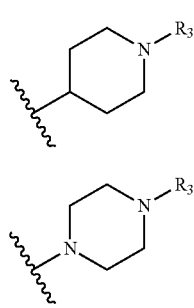

(P-1)

(P-2)

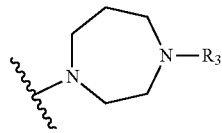

(P-3)

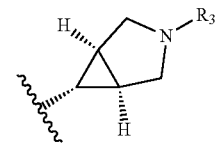

(P-4)

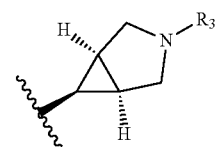

(P-5)

In formulae (P-1) to (P-5) above, $R_3$ represents an alkyl group having 1 to 3 carbon atoms.

In one embodiment, the ring P represents any of formula (P-1), formulae (P-2), (P-4) and (P-5).

In one embodiment, the ring P represents formula (P-1).

In one embodiment, the present invention is a compound represented by formula (1) below or a pharmaceutically acceptable salt thereof, and may be used as a cationic lipid. The cationic lipid may be a hydrate of the salt or a solvate of the salt.

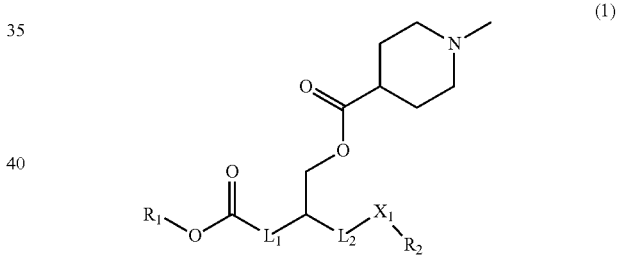

(1)

In formula (1a) and formula (1), $L_1$ and $L_2$ independently represent an alkylene group having 3 to 10 carbon atoms; $R_1$ and $R_2$ independently represent an alkyl group having 4 to 22 carbon atoms or an alkenyl group having 4 to 22 carbon atoms; and $X_1$ represents a single bond or —CO—O—.

As used herein, "alkyl" means a linear, cyclic or branched saturated aliphatic hydrocarbon group having a denoted number of carbon atoms.

As used herein, "alkenyl" means a linear or branched hydrocarbon group having a denoted number of carbon atoms and at least one carbon-carbon double bond. Examples thereof include monoenes, dienes, trienes and tetraenes; however, the term is not limited thereto.

As used herein, "alkylene" means a linear, cyclic or branched bivalent saturated aliphatic hydrocarbon group having a denoted number of carbon atoms.

As used herein, "halogen" means F, Cl, Br or I.

One embodiment of the present invention is a compound represented by formula (1a) or formula (1) above, wherein $L_1$ and $L_2$ independently represent an alkylene group having 3 to 10 carbon atoms (for example 5 to 10 carbon atoms or 3 to 8 carbon atoms); $R_1$ and $R_2$ independently represent an alkyl group having 4 to 18 carbon atoms or an alkenyl group having 4 to 18 carbon atoms; and $X_1$ represents a single bond or —CO—O—, or a pharmaceutically acceptable salt thereof, and may be used as a cationic lipid. The cationic lipid may be a hydrate of the salt or a solvate of the salt.

One embodiment of the present invention is a compound represented by formula (1a) or formula (1) above, wherein $L_1$ and $L_2$ independently represent a linear alkylene group having 3 to 10 carbon atoms (for example 5 to 10 carbon atoms or 3 to 8 carbon atoms); $R_1$ and $R_2$ independently represent a linear or branched alkyl group having 4 to 18 carbon atoms or a linear alkenyl group having 4 to 18 carbon atoms; and $X_1$ is —CO—O—, or a pharmaceutically acceptable salt thereof, and may be used as a cationic lipid. The cationic lipid may be a hydrate of the salt or a solvate of the salt.

Therefore, one embodiment of the present invention is a compound represented by formula (1b) below or a pharmaceutically acceptable salt thereof.

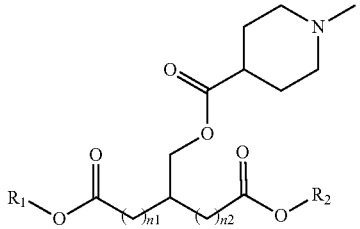

(1b)

In formula (1b), $R_1$ and $R_2$ independently represent an alkyl group having 4 to 22 carbon atoms or an alkenyl group having 4 to 22 carbon atoms, preferably a linear or branched alkyl group having 4 to 18 carbon atoms or a linear alkenyl group having 4 to 18 carbon atoms; and n1 and n2 independently represent an integer of 3 to 10 (for example 5 to 10 or 3 to 8).

In one embodiment of the present invention, the present invention is a compound of formula (1a) or formula (1) above, wherein $X_1$ is —CO—O—; $L_1$ is the same as $L_2$; and $R_1$ is the same as $R_2$ or a pharmaceutically acceptable salt thereof, and may be used as a cationic lipid. The cationic lipid may be a hydrate of the salt or a solvate of the salt.

In one embodiment of the present invention, the present invention is a compound of formula (1a) or formula (1) above, wherein $L_1$ and $L_2$ independently represent a linear alkylene group having 5 to 10 carbon atoms; $R_1$ is a linear or branched alkyl group having 4 to 18 carbon atoms or a linear alkenyl group having 4 to 18 carbon atoms; $R_2$ is a linear alkyl group having 4 to 18 carbon atoms; and $X_1$ is a single bond, or a pharmaceutically acceptable salt thereof. In the present embodiment, the total number of carbon atoms of $L_2$ and $R_2$ is preferably 9 to 12. The compound of the present embodiment may be used as a cationic lipid. The cationic lipid may be a hydrate of the salt or a solvate of the salt.

Therefore, one embodiment of the present invention is a compound represented by formula (1c) below or a pharmaceutically acceptable salt thereof.

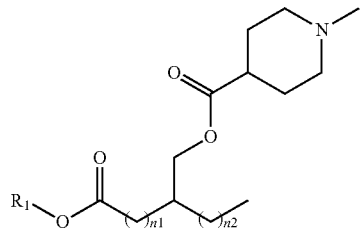

(1c)

In the formula (1c), $R_1$ is an alkyl group having 4 to 22 carbon atoms or an alkenyl group having 4 to 22 carbon atoms, preferably a linear or branched alkyl group having 4 to 18 carbon atoms or a linear alkenyl group having 4 to 18 carbon atoms; n1 represents an integer of 3 to 10 (for example 5 to 10 or 3 to 8); and n2 represents an integer of 8 to 25, preferably 8 to 11.

Examples of the compound according to the embodiment are indicated below.

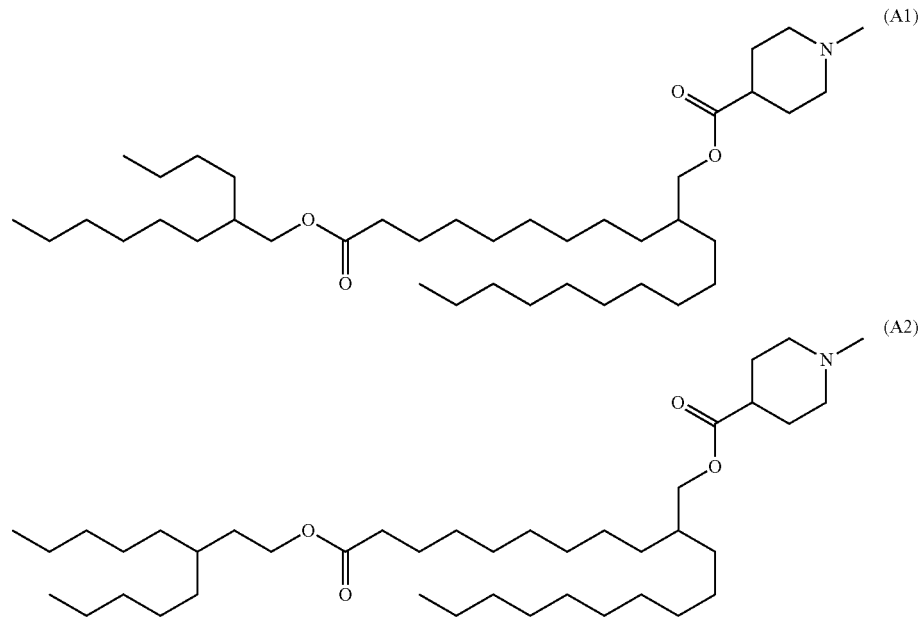

-continued
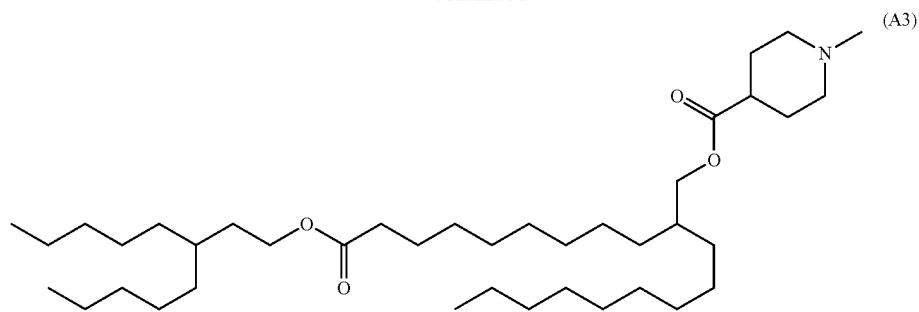
(A3)
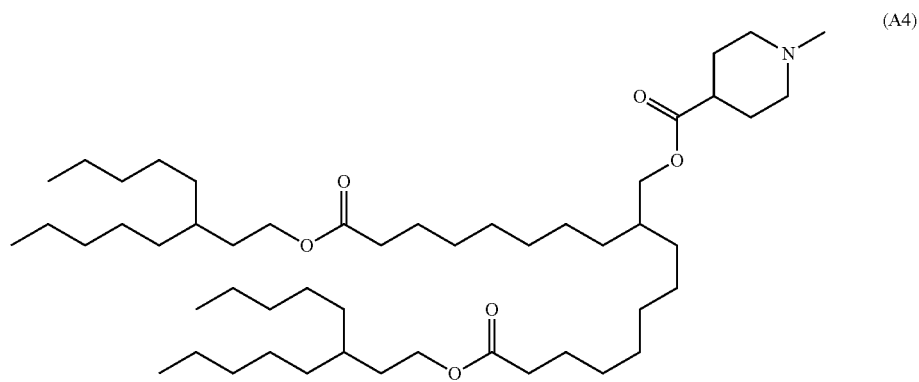
(A4)
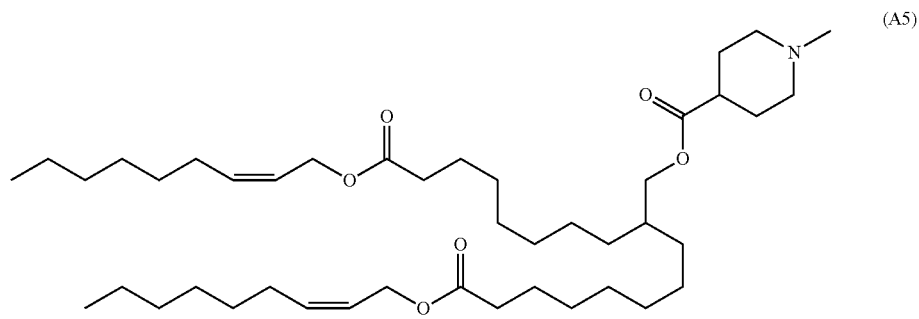
(A5)
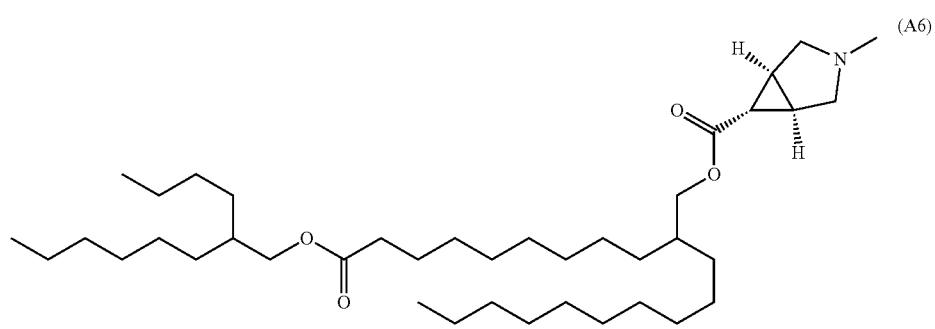
(A6)
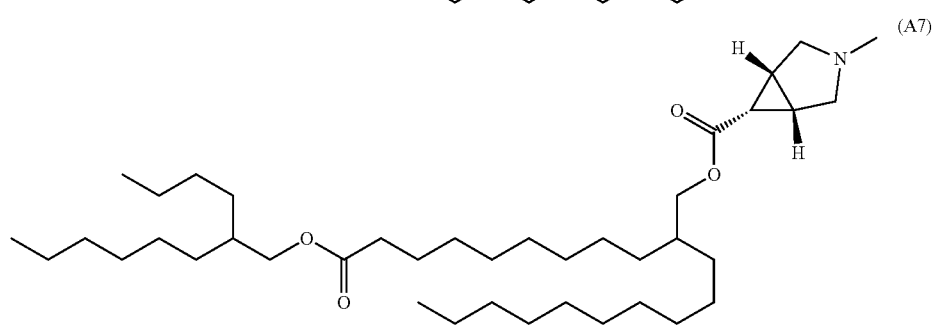
(A7)

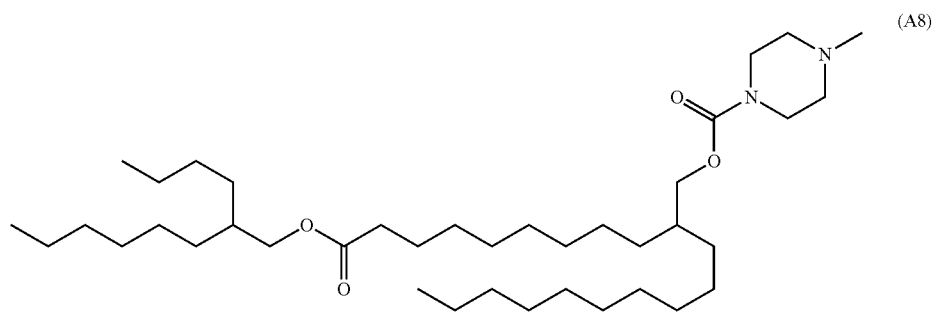
(A8)
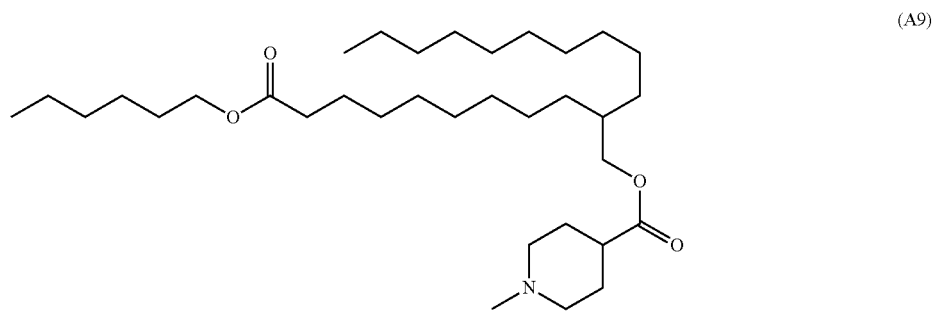
(A9)
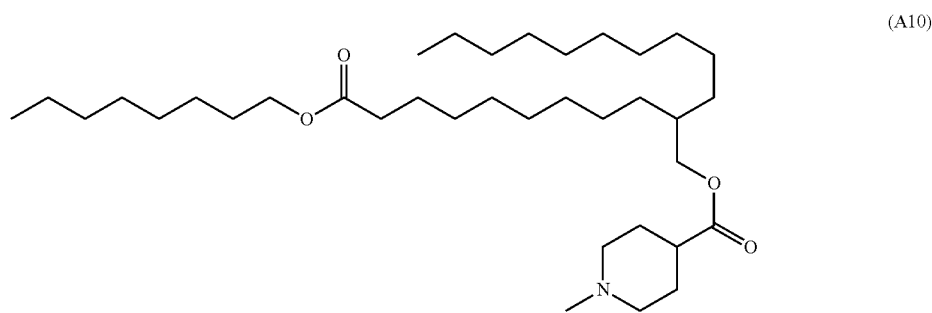
(A10)
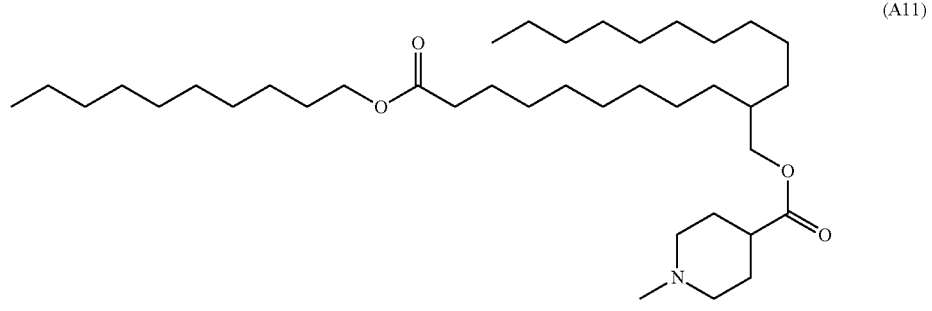
(A11)
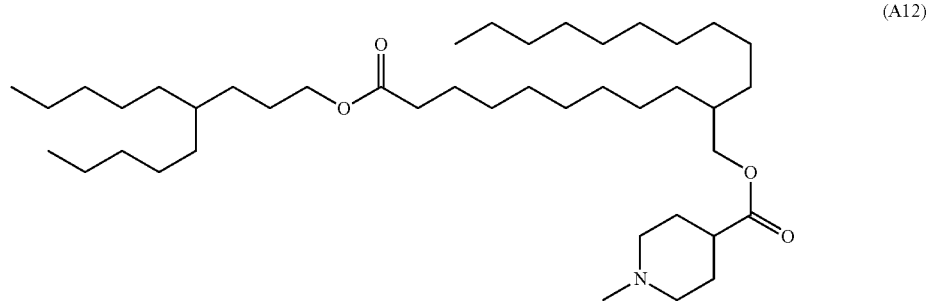
(A12)

-continued
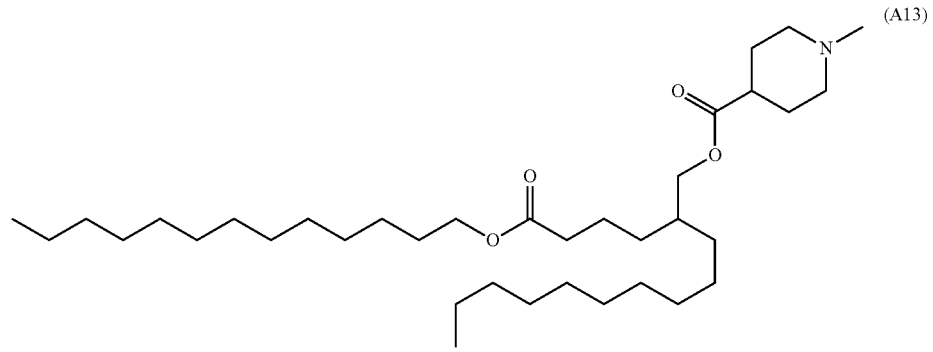
(A13)
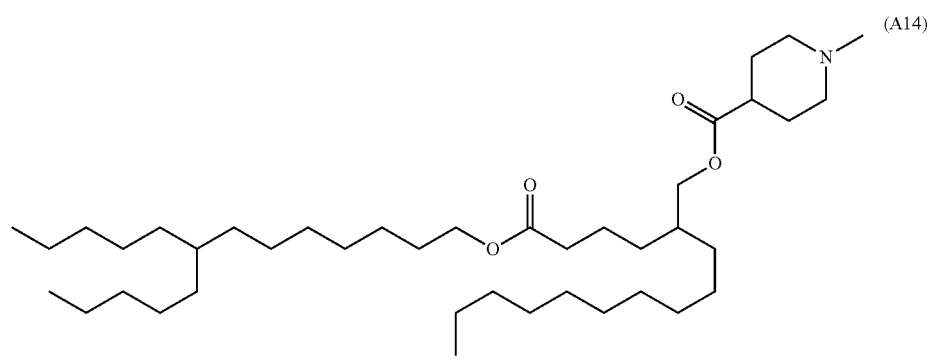
(A14)
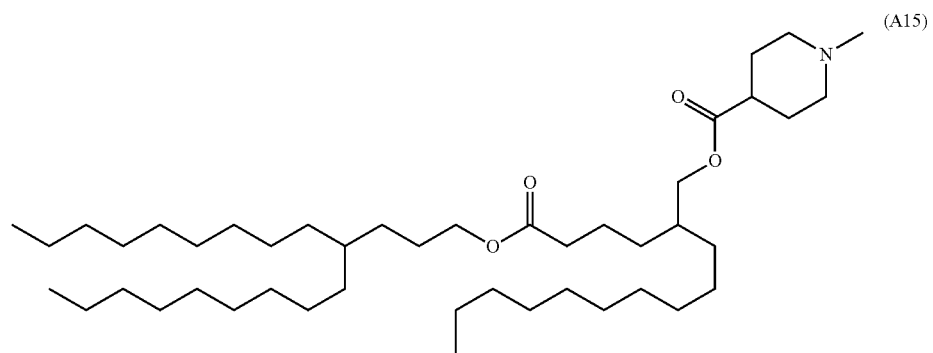
(A15)
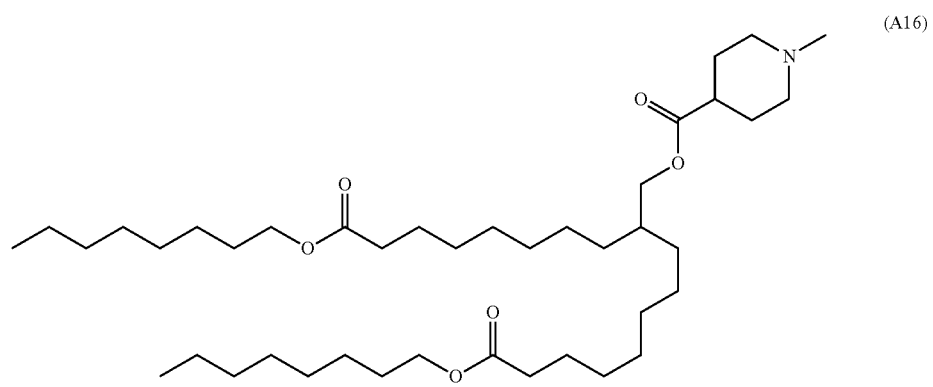
(A16)

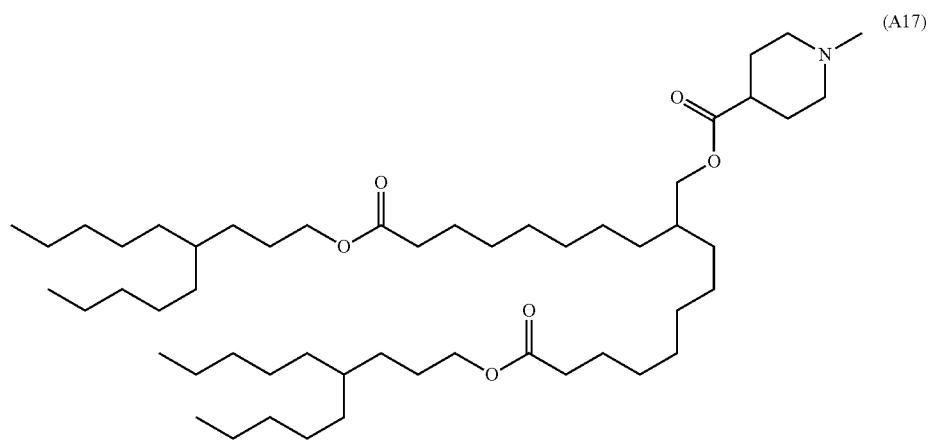
(A17)
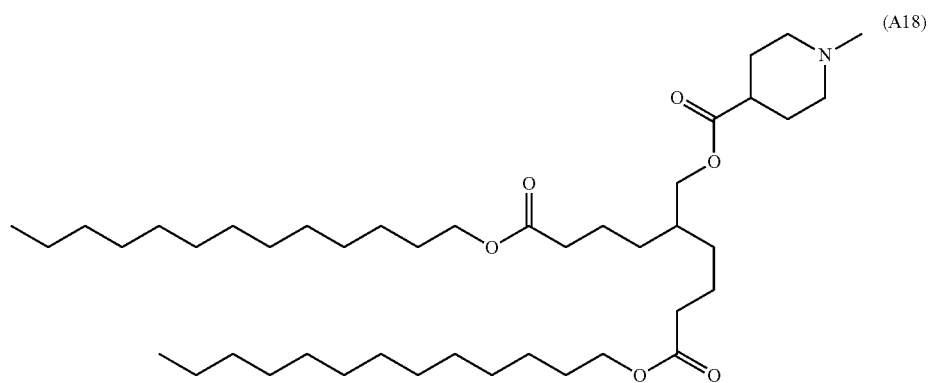
(A18)
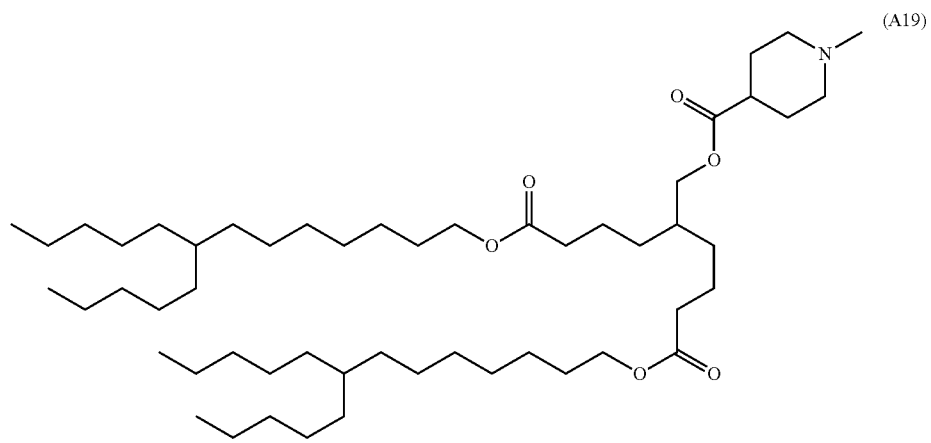
(A19)
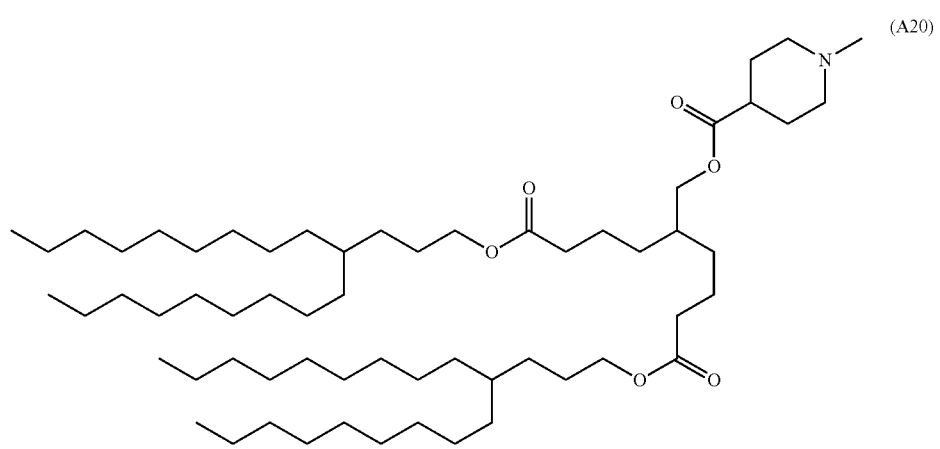
(A20)

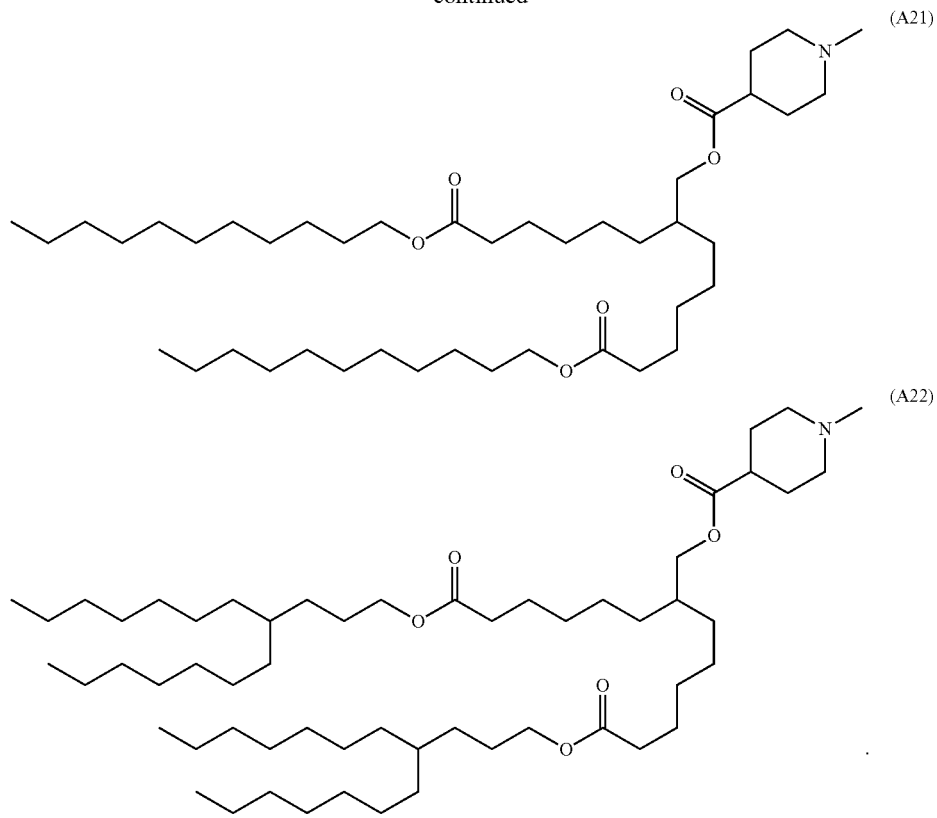

(A21)

(A22)

One embodiment of the present invention is a compound represented by any of formulae (A1) to (A22) above or a pharmaceutically acceptable salt thereof, and may be used as a cationic lipid. The cationic lipid may be a hydrate of the salt or a solvate of the salt.

One embodiment of the present invention is a compound represented by any of formulae (A1) to (A5) and (A9) to (A22) above, or a pharmaceutically acceptable salt thereof, and may be used as a cationic lipid. The cationic lipid may be a hydrate of the salt or a solvate of the salt.

One embodiment of the present invention is a compound represented by any of formulae (A1), (A2), (A3), (A4), (A5), (A9), (A12), (A15), (A16), (A17), (A19), (A20) and (A22) above, or a pharmaceutically acceptable salt thereof, and may be used as a cationic lipid. The cationic lipid may be a hydrate of the salt or a solvate of the salt.

One embodiment of the present invention is a compound represented by any of formulae (A1), (A2), (A3), (A4), (A5), (A9), (A12), (A15) and (A20) above, or a pharmaceutically acceptable salt thereof, and may be used as a cationic lipid. The cationic lipid may be a hydrate of the salt or a solvate of the salt.

One embodiment of the present invention is a compound represented by any of formulae (A1), (A2), (A3), (A4) and (A5) above or a pharmaceutically acceptable salt thereof, and may be used as a cationic lipid. The cationic lipid may be a hydrate of the salt or a solvate of the salt.

One embodiment of the present invention is a compound represented by any of formulae (A6), (A7) and (A5) above or a pharmaceutically acceptable salt thereof, and may be used as a cationic lipid. The cationic lipid may be a hydrate of the salt or a solvate of the salt.

As used herein, "cationic lipid" is an amphiphilic molecule having a lipophilic region containing one or more hydrocarbon groups and a hydrophilic region containing a polar group that undergoes protonation at a physiological pH. Namely, the cationic lipid of the present invention may be protonated to form a cation. For example, the compound represented by formula (1) above encompasses the compound (cation) represented by formula (1)' below in which a hydrogen ion coordinates with a lone electron-pair on the nitrogen atom on the piperidine ring.

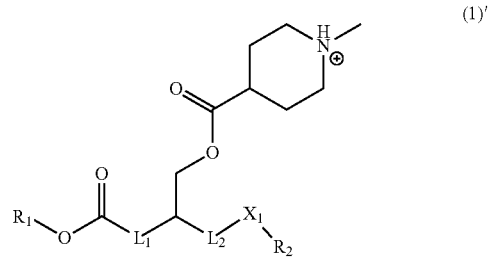

(1)'

The anion that may be included in the cationic lipid of the present embodiment by forming a pair with the cation is not particularly limited as far as the anion is pharmaceutically acceptable. Examples thereof include inorganic ions such as a chloride ion, an iodide ion, a nitrate ion, a sulphate ion and a phosphate ion; organic acid ions such as an acetate ion, an oxalate ion, a maleate ion, a fumarate ion, a citrate ion, a benzoate ion and a methanesulphonate ion; and the like.

The cationic lipid of the present invention may have a stereoisomer such as a geometric isomer and an optical isomer or a tautomer. The cationic lipid of the present invention encompasses all possible isomers including the above and mixtures thereof.

(Production Method of the Cationic Lipid)

The method for producing the cationic lipid of the present invention is now described. Embodiments of the synthetic scheme of the cationic lipid are indicated in formulae (10) and (11) below. All the compounds described herein are encompassed by the present invention as the compounds. The compound of the present invention may be synthesized according to at least one method illustrated in the schemes indicated below.

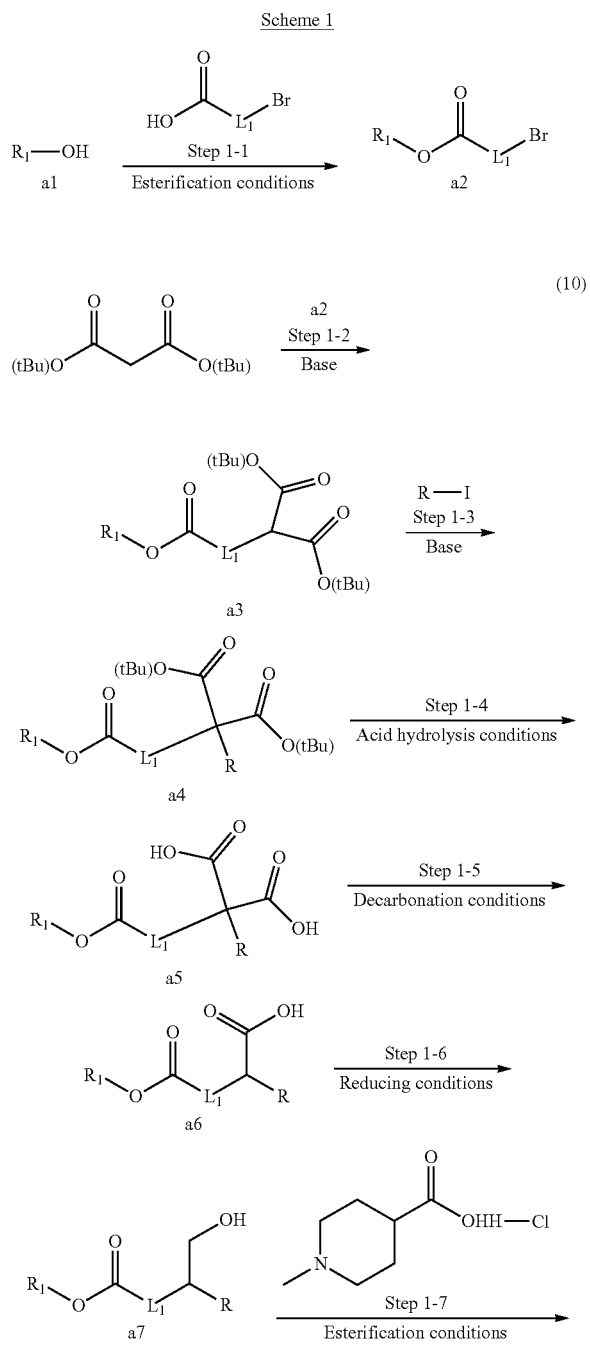

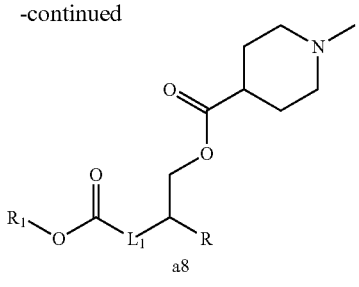

In the formula, $L_1$ and $R_1$ respectively are defined as above; and R is $-L_2$-$X_1$—$R_2$ (wherein $L_2$, $X_1$ and $R_2$ respectively are defined as above) in formula (1).

The cationic lipid of formula (1) (compound wherein $X_1$ is a single bond) may be synthesized, for example, according to scheme 1 illustrated in formula (10) above.

(Step 1-1: Esterification)

First, alcohol (a1) and a halogenated alkylcarboxylic acid X-$L_1$-COOH (X is a halogen atom and $L_1$ is defined as above) (preferably a brominated alkylcarboxylic acid) are reacted in the presence of a condensation agent to obtain halogenated ester (a2). Examples of the condensation agent include 1-[3-(dimethylamino)propyl]-3-ethylcarbodiimide (EDC) hydrochloride, N,N'-dicyclohexylcarbodiimide (DCC) and the like. Optionally, a base may be added. Examples of the base include NMM, TEA, DIPEA, DMAP, pyridine, picoline, lutidine and the like. Examples of the solvent include tetrahydrofuran (THF), methylene chloride, chloroform, benzene, hexane, ethyl acetate and the like.

(Step 1-2: Introduction of Alkyl Chain)

Next, halogenated ester (a2) and di-tert-butyl malonate are reacted in the presence of a base. By the reaction, a hydrogen atom of active methylene in the malonic diester is abstracted to introduce an alkylester chain, thereby obtaining compound (a3). Examples of the base include NaH. Examples of the solvent include ethers such as dioxane, tetrahydrofuran, cyclopentyl methyl ether and 1,2-dimethoxyethane.

(Step 1-3: Introduction of Alkyl Chain)

Next, compound (a3) and an alkyl halide (preferably iodide) are reacted in the presence of a base to introduce an alkyl chain, thereby obtaining compound (a4). The base and the solvent may be similar to those in step 1-2 above.

(Step 1-4: Deprotection)

Next, the tert-butyl group of compound (a4) is deprotected under acid hydrolysis conditions to obtain compound (a5). Examples of the acid used for deprotection include trifluoroacetic acid (TFA), hydrochloric acid and the like. Examples of the solvent include methylene chloride and the like.

(Step 1-5: Decarbonation)

Next, carboxylic acid (a6) is obtained by decarbonation of compound (a5). The decarbonation reaction may be conducted by, for example, heating in a solvent. Examples of the solvent include aromatic hydrocarbons such as benzene, toluene and xylene.

(Step 1-6: Reduction Step)

The carboxyl group of compound (a6) is reduced to a hydroxyl group in the presence of a reducing agent to obtain compound (a7). Examples of the reducing agent include borane complexes such as borane ($BH_3$)-tetrahydrofuran complex and borane-dimethyl sulphide complex. Examples of the solvent include ethers such as diethyl ether, tetrahydrofuran and dioxane; halogenated hydrocarbons such as chloroform, methylene chloride and dichloroethane; hydrocarbons such as hexane, benzene and toluene; and mixed solvents thereof.

(Step 1-7: Esterification)

The obtained alcohol (a7) and 1-methyl-piperidine-4-carboxylic acid or a derivative thereof (hydrogen halide and the like) are reacted in the presence of a condensation agent and a base to obtain a final product, compound (a8) (R=$L_2$-$X_1$—$R_2$) (compound corresponding to the cationic lipid of formula (1)). The condensation agent and the base used may be similar to those in step 1-1.

When the compound wherein $X_1$ is —CO—O— is synthesized, a compound of which carboxyl group is protected according to step 2-1 described below may be prepared in step 1-3 in scheme 1 above, the compound may be reacted with compound (a3) and deprotection and esterification may be finally conducted.

Scheme 2

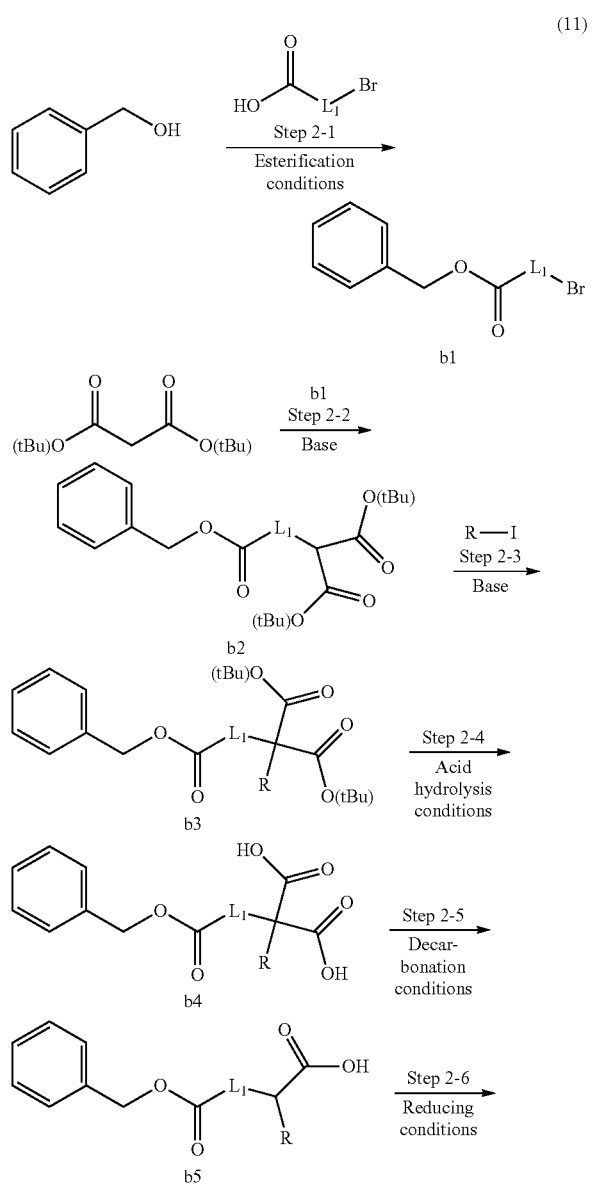

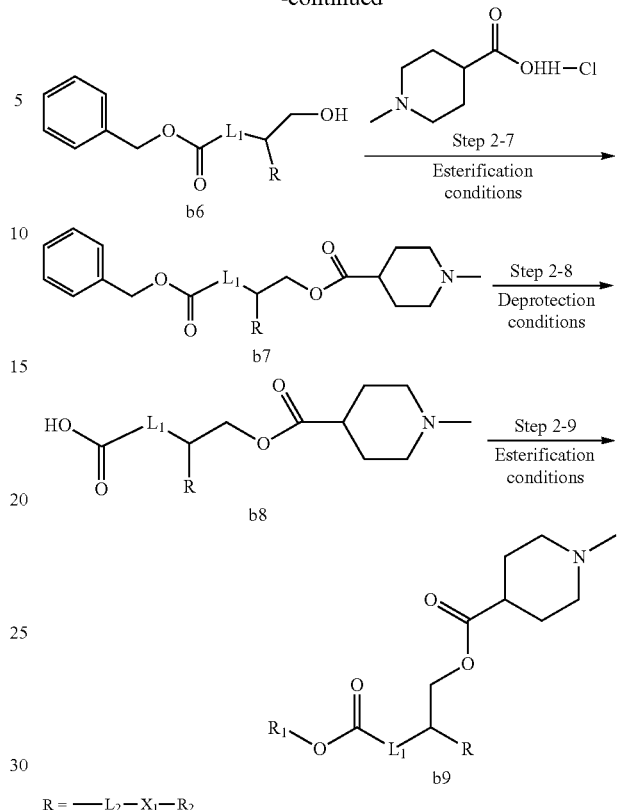

R = —$L_2$—$X_1$—$R_2$

In the formula, $L_1$ and $R_1$ respectively are defined as above; R is -$L_2$-$X_1$—$R_2$ ($L_2$, $X_1$ and $R_2$ respectively are defined as above) in formula (1).

Scheme 2 above illustrates another method for synthesizing the cationic lipid of formula (1) (compound wherein $X_1$ is a single bond) used by a person skilled in the art.

(Step 2-1: Esterification)

First, benzyl alcohol and a halogenated alkylcarboxylic acid are condensed to obtain halogenated ester (b1). The esterification conditions are the same as in step 1-1.

(Step 2-2: Introduction of Alkyl Chain)

Next, similar to step 1-2, halogenated ester (b1) and di-tert-butyl malonate are reacted in the presence of a base to obtain compound (b2).

(Step 2-3: Introduction of Alkyl Chain)

Next, similar to step 1-3, compound (b2) and an alkyl halide are reacted in the presence of a base to obtain compound (b3).

(Step 2-4: Deprotection)

Next, similar to step 1-4, the tert-butoxycarbonyl group of compound (b3) is deprotected under acid hydrolysis conditions to obtain compound (b4).

(Step 2-5: Decarbonation)

Next, similar to step 1-5, carboxylic acid (b5) is obtained.

(Step 2-6: Reduction Step)

Further, similar to step 1-6, the product of the previous step is reduced in the presence of a reducing agent to obtain compound (b6).

(Step 2-7: Esterification)

The obtained compound (b6) and 1-methyl-piperidine-4-carboxylic acid or a derivative thereof (hydrogen halide and the like) are esterified in the presence of a condensation agent and a base to obtain compound (b7).

(Step 2-8: Deprotection)

Next, under reducing conditions, the benzyl protecting group is deprotected to obtain compound (b8). Deprotection may be conducted, for example, by catalytic hydrogenation reaction in the presence of a metal catalyst such as palladium/carbon.

(Step 2-9: Esterification)

Finally, compound (b8) may be reacted with an alcohol ($R_1OH$) to obtain compound (b9) ($R=L_2-X_1—R_2$) (compound corresponding to the cationic lipid of formula (1)).

When the compound wherein $X_1$ is —CO—O— is synthesized, a compound of which carboxyl group is protected according to step 2-1 may be reacted with compound (b2) in step 2-3 of scheme 2 above, and the product may be deprotected in step 2-8.

The compound of formula (1a) above may also be synthesized according to scheme 1 or 2 above. Specifically, when the ring P has a structure of formula (P-1), (P-4) or (P-5), a carboxylic acid corresponding to the structure of formula (P-1), (P-4) or (P-5) may be used for esterification reaction in, for example, step 1-7 or step 2-7 instead of 1-methyl-piperidine-4-carboxylic acid. When the ring P has a structure of formula (P-2) or (P-3), the compound represented by formula (1a) may be obtained by reacting, instead of step 1-7, compound a7 obtained in step 1-6, a carbonylation reagent (for example, a chloroformate ester such as 4-nitrophenyl chloroformate), and N-alkylpiperazine or N-alkylhomopiperazine (compound having the structure of formula (P-2) or (P-3)) in the presence of a base (see Example A-8 below).

In synthesis of the compound of the present invention, unless the production of starting materials is particularly recited, the compounds are known or may be prepared according to similar methods that are well known in the art or as described in Examples below. A person skilled in the art understands that the above schemes are merely typical preparation methods of the compound of the present invention and can apply other well-known methods.

In preparation of the compound of the present invention, protection of a functional group of a molecule may be necessary and/or desirable. This may be carried out with a conventional protecting group that is well known to a person skilled in the art. The protecting group may be eliminated according to a well-known method in the art at any following appropriate stage. The protecting groups (such as a tert-butyl protecting group and a benzyl protecting group) indicated in the above schemes may be replaced by other protecting groups that are well known to a person skilled in the art.

(Lipid Complex)

The present invention provides a lipid complex containing (I) the cationic lipid described above and (II) at least one lipid selected from the group consisting of a neutral lipid, a polyethylene glycol-modified lipid and a sterol. The lipid complex according to one embodiment of the present invention contains (I) the cationic lipid described above, (II) at least one lipid selected from the group consisting of a neutral lipid, a polyethylene glycol-modified lipid and a sterol and (III) a nucleic acid. Thus, the lipid complex of the present invention may or may not contain a nucleic acid. The lipid complex of the present embodiment allows effective release of a nucleic acid into the cytoplasm. The lipid complex of the present embodiment is prevented from an increase in the particle diameter after the storage over a certain period of time (for example 1 month or 3 months) and may exhibit excellent physical stability.

Examples of the form of the complex formed from the lipid containing the cationic lipid and a nucleic acid include a complex of a nucleic acid and a membrane (reverse micelle) formed from a lipid monolayer (single molecular layer), a complex of a nucleic acid and a liposome, a complex of a nucleic acid and a micelle and the like. In the lipid complex according to one embodiment of the present invention, a nucleic acid is encapsulated in a fine particle formed with a lipid containing the cationic lipid.

The lipid complex of the present embodiment contains, based on the total lipid content of the lipid complex, the cationic lipid at, for example, 10% to 100% by mole, such as 20% to 90% by mole, such as 40% to 80% by mole. The cationic lipid used may be used alone or as a mixture of two or more.

Examples of the nucleic acid include siRNA, miRNA, shRNA expression vector, antisense oligonucleotide, mRNA, ribozyme and the like. In one embodiment, the nucleic acid may be siRNA, miRNA or mRNA.

The lipid complex of the present embodiment contains, relative to the total weight of the lipid complex, the nucleic acid at, for example, 0.01% to 50% by weight, such as 0.1% to 30% by weight, such as 1% to 10% by weight.

The lipid complex of the present embodiment contains, as lipid components, (I) the cationic lipid and (II) at least one lipid selected from the group consisting of a neutral lipid, a polyethylene glycol-modified lipid and a sterol. The lipid complex of the present embodiment contains, relative to the total weight of the lipid complex, the lipid components at, for example, 50% to 100% by weight, such as 70% to 99.99—by weight, such as 90% to 99% by weight.

"Neutral lipid" means a lipid that exists in uncharged form or in neutral amphoteric ion at a physiological pH. Examples of the neutral lipid include dioleoyl phosphatidylethanolamine (DOPE), palmitoyl oleoyl phosphatidylcholine (POPC), egg phosphatidylcholine (EPC), dimyristoyl phosphatidylcholine (DMPC), dipalmitoyl phosphatidylcholine (DPPC), distearoyl phosphatidylcholine (DSPC), diarachidoyl phosphatidylcholine (DAPC), dibehenoyl phosphatidylcholine (DBPC), dilignoceroyl phosphatidylcholine (DLPC), dioleoyl phosphatidylcholine (DOPC), sphingomyelin, ceramide, dioleoyl phosphatidylglycerol (DOPG), dipalmitoyl phosphatidylglycerol (DPPG), phosphatidylethanolamine (POPE), dioleoyl-phosphatidylethanolamine 4-(N-maleimidomethyl)-cyclohexane-1-carboxylate (DOPE-mal) and the like. The neutral lipid may be used alone or as a mixture of two or more.

The lipid complex of the present embodiment may contain, based on the total lipid content in the lipid complex, the neutral lipid at, for example, 0% to 50% by mole, such as 0% to 40% by mole, such as 0% to 30% by mole.

Examples of the polyethylene glycol-modified lipid include PEG2000-DMG (PEG2000-dimyristyl glycerol), PEG2000-DPG (PEG2000-dipalmitoyl glycerol), PEG2000-DSG (PEG2000-distearoyl glycerol), PEG5000-DMG (PEG5000-dimyristyl glycerol), PEG5000-DPG (PEG5000-dipalmitoyl glycerol), PEG5000-DSG (PEG5000-distearoyl glycerol), PEG-cDMA (N-[(methoxy-poly(ethylene glycol)2000) carbamyl]-1,2-dimyristyloxyl-propyl-3-amine), PEG-C-DOMG (R-3-[(ω-methoxy-poly(ethylene glycol)2000)carbamoyl]-1,2-dimyristyloxylpropyl-3-amine), polyethylene glycol (PEG)-diacyl glycerol (DAG), PEG-dialkyloxypropyl (DAA), PEG-phospholipid, PEG-ceramide (Cer) and the like.

Examples of the PEG-dialkyloxypropyl include PEG-dilauryloxypropyl, PEG-dimyristyloxypropyl, PEG-dipalmityloxypropyl, PEG-distearyloxypropyl and the like.

The polyethylene glycol-modified lipid may be used alone or as a mixture of two or more.

The lipid complex of the present embodiment may contain, based on the total lipid content in the lipid complex, the polyethylene glycol-modified lipid at, for example, 0% to 30% by mole, such as 0% to 20% by mole, such as 0% to 10% by mole.

The sterol is an alcohol having a steroid back bone. Examples of the sterol include cholesterol, dihydrocholesterol, lanosterol, β-sitosterol, campesterol, stigmasterol, brassicasterol, ergocasterol, fucosterol, 3β-[N—(N',N'-dimethylaminoethyl)carbamoyl]cholesterol (DC-Chol) and the like. The sterol may be used alone or as a mixture of two or more.

The lipid complex of the present embodiment may contain, based on the total lipid content in the lipid complex, the sterol at, for example, 0% to 90% by mole, such as 10% to 80% by mole, such as 20% to 50% by mole.

The lipid components in the lipid complex of the present embodiment may be combined without any limitation, and examples of the combination include a combination of the cationic lipid, the neutral lipid and the sterol described above, a combination of the cationic lipid, the neutral lipid, the polyethylene glycol-modified lipid and the sterol described above and the like.

(Composition)

In one embodiment, the present invention provides a composition containing (I) the cationic lipid, (II) at least one lipid selected from the group consisting of a neutral lipid described above, a polyethylene glycol-modified lipid and a sterol and (III) a nucleic acid. The composition of the present embodiment allows efficient release of a nucleic acid into the cytoplasm. The composition of the present embodiment may contain the lipid complex described above, a pharmaceutically acceptable medium and optionally other additives. The pharmaceutically acceptable medium and other additives are described hereinafter.

The composition of the present embodiment contains, based on the total lipid content in the composition, the cationic lipid at, for example, 10% to 100% by mole, such as 20% to 90% by mole, such as 40% to 70% by mole. The cationic lipid may be used alone or as a mixture of two or more.

Examples of the nucleic acid include those described above. The composition of the present embodiment contains, relative to the total weight of the composition, the nucleic acid at, for example, 0.01% to 50% by weight, such as 0.1% to 30% by weight, such as 1% to 10% by weight.

The composition of the present embodiment contains, as lipid components, (I) the cationic lipid described above and (II) at least one lipid selected from the group consisting of a neutral lipid, a polyethylene glycol-modified lipid and a sterol.

Examples of the neutral lipid include those described above. The composition of the present embodiment may contain, based on the total lipid content in the composition, the neutral lipid at, for example, 0% to 50% by mole, such as 0% to 40% by mole, such as 0% to 30% by mole.

Examples of the polyethylene glycol-modified lipid includes those described above. The composition of the present embodiment may contain, based on the total lipid content in the composition, the polyethylene glycol-modified lipid at, for example, 0% to 30% by mole, such as 0% to 20% by mole, such as 0% to 10% by mole.

Examples of the sterol include those described above. The composition of the present embodiment may contain, based on the total lipid content in the composition, the sterol at, for example, 0% to 90% by mole, such as 10% to 80% by mole, such as 20% to 50% by mole.

The lipid components in the composition of the present embodiment may be combined without any limitation, and examples thereof include a combination of the cationic lipid, the neutral lipid and the sterol described above, a combination of the cationic lipid, the neutral lipid, the polyethylene glycol-modified lipid and the sterol described above and the like.

The composition of the present embodiment may contain, as other additives, saccharides such as sucrose, glucose, sorbitol and lactose; amino acids such as glutamine, glutamic acid, sodium glutamate and histidine; salts of acids such as citric acid, phosphoric acid, acetic acid, lactic acid, carbonic acid and tartaric acid and the like.

The composition of the present embodiment may be formulated as a pharmaceutical composition. Examples of the dosage form of the pharmaceutical composition include an injectable.

The composition of the present embodiment may be, for example, in a powder state obtained by removing a solvent by freeze-drying or the like or in a liquid state. The composition according to one embodiment of the present invention is a powder composition containing the lipid complex according to the embodiment described above. The powder composition may be prepared from a composition in a liquid state (dispersion) by removing a solvent by, for example, filtration or centrifugation, or prepared by freeze-drying the dispersion. When the composition is in a powder state, the composition may be suspended or dissolved in a pharmaceutically acceptable medium before using the same as an injectable. The composition according to one embodiment of the present invention is a liquid composition containing the lipid complex according to the embodiment described above and a pharmaceutically acceptable medium. When the composition is in a liquid state, the composition may be used directly or as an injectable after dissolving the composition in a pharmaceutically acceptable medium.

Examples of the pharmaceutically acceptable medium include sterile water, saline; isotonic solutions containing an adjuvant such as glucose, D-sorbitol, D-mannose, D-mannitol and sodium chloride; buffers such as phosphate buffer, citrate buffer and acetate buffer, and the like. The composition of the present embodiment may further contain additives including a dissolution adjuvant such as alcohols including ethanol, propylene glycol and polyethylene glycol, a stabilizing agent, an antioxidant, an antiseptic, a vehicle that is generally used in production of drugs, a filler, a bulking agent, a binding agent, a humectant, a disintegrating agent, a lubricant, a surfactant, a dispersant, a preservative, a flavoring agent, a soothing agent and the like.

The composition may be administered to a patient by parenteral manners such as an intra-arterial injection, an intravenous injection and a hypodermic injection. The dose of the composition may vary according to the subject to be administered, the target organ, the symptom or the mode of administration. The subject to which the composition is administered is not limited and the composition may be applied to various animals. Particularly, the composition may be administered to a mammal, preferably a human and an experimental animal in clinical tests, screening and laboratory experiments.

The composition of the present embodiment forms a lipid complex containing a nucleic acid encapsulated in fine particles formed with lipids containing the cationic lipid. The "average particle diameter" of the lipid complex may be calculated according to any of the volume average, the number average and the Z-average. In the composition of the present embodiment, the lipid complex may have an average particle diameter (Z-average) of, for example, 10 to 1000 nm, such as 30 to 500 nm, such as 30 to 200 nm.

The composition of the present embodiment is preferably such that the particle diameter of the lipid complex hardly increases during a storage period compared to that before the storage. For example, it is preferable that the average particle diameter (Z-average) after a storage at 4° C. for 3 months is preferably 1.3 times or less, more preferably 1.2 times or less and particularly preferably 1.1 times or less of the particle diameter before the storage.

From the viewpoint of suppressing nonspecific adsorption and immune reaction, the composition of the present embodiment preferably has almost no surface charge in an environment of pH of about 7.4 such as in blood. From the viewpoint of improving the fusion efficiency with an endosomal membrane during incorporation into cells by endocytosis, it is preferable that the composition is positively charged in an environment of low pH (for example 3.5 to 7.0).

(Production Method of Composition)

In one embodiment, the present invention provides a method for producing a composition, the method including: the step (a) of mixing a polar organic solvent-containing aqueous solution containing (I) the cationic lipid described above, (II) at least one lipid selected from the group consisting of a neutral lipid, a polyethylene glycol-modified lipid and a sterol with an aqueous solution containing (III) a nucleic acid to obtain a mixed solution; and the step (b) of reducing a content percentage of the polar organic solvent in the mixed solution. The production method according to the present embodiment allows production of the composition that can effectively release a nucleic acid into the cytoplasm.

The lipid complex containing nucleic acids encapsulated in fine particles formed with the lipids may be formed by the electrostatic interaction between water-soluble nucleic acids and the cationic lipid and the hydrophobic interaction between lipids. For example, by reducing the content percentage of the polar organic solvent in the mixed solution, the solubility of lipid components including (I) the cationic lipid described above and (II) at least one lipid selected from the group consisting of a neutral lipid, a polyethylene glycol-modified lipid and a sterol in the polar organic solvent-containing aqueous solution may be changed, thereby forming the lipid complex. Examples of the polar organic solvent include alcohols such as ethanol.

First, in the step (a), a polar organic solvent-containing aqueous solution containing (I) the cationic lipid and (II) at least one lipid selected from the group consisting of a neutral lipid, a polyethylene glycol-modified lipid and a sterol dissolved therein and an aqueous solution containing (III) a nucleic acid are mixed to obtain a mixed solution. The concentration of the polar organic solvent in the polar organic solvent-containing aqueous solution is not particularly limited as long as lipid molecules can be solubilized even after being mixed with the aqueous solution of the nucleic acid. For example, the concentration of the polar organic solvent in the polar organic solvent-containing aqueous solution in the step (a) may be 0% to 60% by weight.

Next, in the step (b), water or the like is added to the mixed solution to reduce the content percentage of the polar organic solvent. As a result, the lipid complex may be formed. In order to form the lipid complex effectively, it is preferable that the content percentage of the polar organic solvent is rapidly reduced. For example, the concentration of the polar organic solvent in the final polar organic solvent-containing aqueous solution in the step (b) may be 0% to 5% by weight.

Alternatively, the mixed solution obtained in the step (a) may be subjected to dialysis to remove the polar organic solvent and replace the solvent by a pharmaceutically acceptable medium. Because the content percentage of the polar organic solvent in the solution decreases during the dialysis process, the lipid complex may be formed as a result.

According to the method for producing the composition of the present embodiment, the lipid complex containing a nucleic acid efficiently encapsulated in fine particles can be obtained. The lipid complex may have excellent physical stability. For example, after the storage over a certain period of time (for example 1 month or 3 months), an increase of the particle diameter may be suppressed.

When the nucleic acid encapsulated in the composition is an oligonucleotide therapeutic, the composition may be used as a pharmaceutical composition. For example, the composition of the present invention may be used in the therapy (such as gene therapy) for introducing a desired nucleic acid to the target cytoplasm (such as cytoplasm causing a disease) in vivo or in vitro. Thus, the present invention according to one embodiment provides a method (particularly a gene therapy method) of therapy of various diseases by using the pharmaceutical composition containing the lipid complex. The subject to be administered, the method and condition of administration are the same as above.

The present invention according to one embodiment may be a kit for delivering an oligonucleotide therapeutic, containing the above anionic lipid. The kit may also be preferably used in the therapy (such as gene therapy) of various target cells. In the kit of the present embodiment, the state of storage of the anionic lipid is not particularly limited, and may be any state such as solution or powder by taking the stability (storage property), convenience of use and the like into account. The kit of the present embodiment may contain, in addition to the above anionic lipid, for example various nucleic acids, various media (pharmaceutically acceptable media, buffers), an instruction (instruction manual) and the like. The kit of the present embodiment is used for preparing a composition or a lipid complex containing a desired nucleic acid to be introduced into target cells and lipids containing the above anionic lipid. The prepared composition or lipid complex may be effectively used for delivery of the nucleic acid to the target cells. Further, the present invention according to one embodiment may be a kit for delivering an oligonucleotide therapeutic, containing a pharmaceutical composition that contains the anionic lipid. The kit of the present embodiment may contain, in addition to the pharmaceutical composition, for example, various media (pharmaceutically acceptable media), an instruction (instruction manual) and the like.

EXAMPLES

The present invention is more specifically described hereinafter by way of Examples, Production Examples and Test Examples. However, the present invention is not limited to Examples. In Examples and Production Examples, the nomenclature of the compounds is obtained on the software (product name "ChemDraw Ultra ver. 12.0", produced by PerkinElmer Co., Ltd.).

All starting materials, reagents, acids, bases, dehydrating agents, solvents and catalysts that are used for synthesis of the compounds of the present invention are commercially available or may be produced according to the organic synthesis methods that are well known to a person skilled in the art. Further, the compounds of the present invention may be, as demonstrated in Examples below, produced according to the organic synthesis methods that are well known to a person skilled in the art.

The abbreviations used in Examples are conventional and well known to a person skilled in the art. Some of the abbreviations are indicated below.
DIPEA: N,N-Diisopropylethylamine
DMAP: 4-(Dimethylamino)pyridine
DMF: N,N-Dimethylformamide
EDC: 1-Ethyl-3-(3-dimethylaminopropyl)carbodiimide hydrochloride
n-: Normal
tert-: Tertiary
EtOAc: Ethyl acetate
TFA: Trifluoroacetic acid
THF: Tetrahydrofuran
$^1$H-NMR: Proton nuclear magnetic resonance spectrometry In Examples and Production Examples below, "room temperature" indicates generally from about 10*C to about 35° C. % indicates percent by weight unless otherwise stated.

The chemical shifts of proton nuclear magnetic resonance spectrometry are recorded in δ unit (ppm) from tetramethylsilane. The abbreviations in the patterns are as indicated below:

s: singlet, d: doublet, t: triplet, q: quartet, quin: quintet, m: multiplet, br: broad.

For chromatography, Parallel Prep produced by YAMAZEN Corporation {column: produced by YAMAZEN Corporation, Hi-Flash™ Column (Silica gel), size; S (16×60 mm), M (20×75 mm), L (26×100 mm), 2 L (26×150 mm)}, or flash automatic purification system Isolera™ produced by Biotage {column: SNAP Cartridge KP-Sil (10 g, 25 g, 50 g, 100 g, 340 g)} was used.

A. Synthesis of Cationic Lipid

Production Example 1

Synthesis of 2-butyloctyl 9-bromononanoate

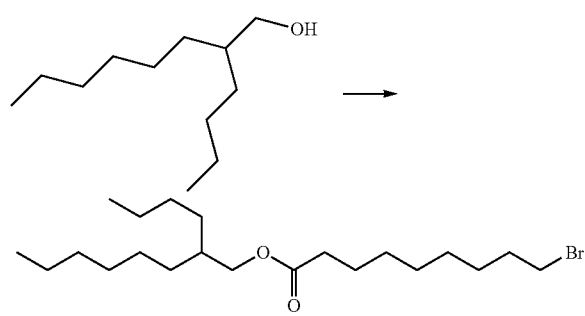

9-Bromononanoic acid (1.1 g, 4.7 mmol), DIPEA (0.91 mL, 5.3 mmol) and DMAP (76 mg, 0.63 mmol) were dissolved in methylene chloride (13 mL) and under ice cooling, EDC (1.0 g, 5.3 mmol) was added. 2-Butyl-1-octanol (0.58 g, 3.1 mmol) was added and the mixture was stirred at room temperature for 2 hours. The reaction mixture was added with a saturated sodium hydrogen carbonate aqueous solution and extracted with ethyl acetate. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (1.2 g, 2.96 mmol).

$^1$H-NMR (400 MHz, CDCl$_3$) δ(ppm): 0.82-0.95 (m, 6H), 1.17-1.49 (m, 24H), 1.52-1.70 (m, 3H), 1.75-1.93 (m, 2H), 2.23-2.36 (m, 2H), 3.34-3.47 (m, 2H), 3.91-4.02 (m, 2H).

Production Example 2

Synthesis of benzyl 9-bromononanoate

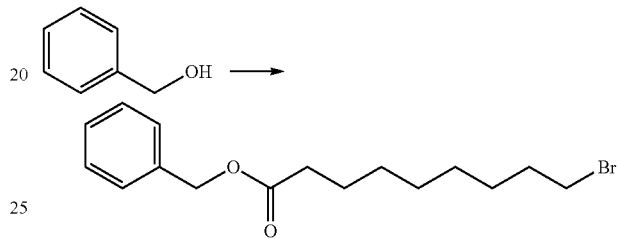

Benzyl alcohol (0.50 mL, 4.84 mmol), 9-bromononanoic acid (1.38 g, 5.80 mmol) and DMAP (59 mg, 0.48 mmol) were dissolved in methylene chloride (9.6 mL), and under ice cooling, EDC (1.16 g, 6.05 mmol) was added and the mixture was stirred at room temperature for 2 hours. The reaction mixture was added with a saturated sodium hydrogen carbonate aqueous solution and extracted with diethyl ether. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (1.49 g, 4.55 mmol).

$^1$H-NMR (400 MHz, CDCl$_3$) δ(ppm): 1.22-1.48 (m, 8H), 1.58-1.71 (m, 2H), 1.78-1.90 (m, 2H), 2.30-2.40 (m, 2H), 3.35-3.44 (m, 2H), 5.12 (s, 2H), 7.26-7.45 (m, 5H).

Production Example 3

Synthesis of benzyl 8-bromooctanoate

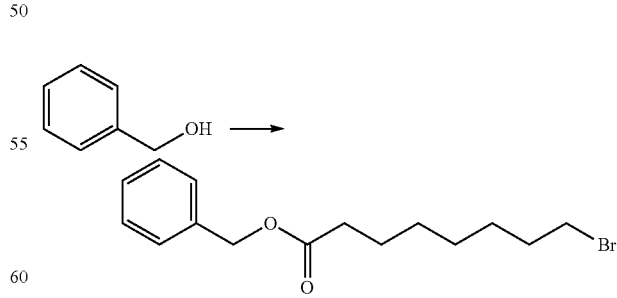

According to the method in Production Example 2, the titled compound (4.8 g, 15.3 mmol) was obtained from benzyl alcohol (1.85 mL, 17.9 mmol), 8-bromooctanoic acid (4.0 g, 17.9 mmol), EDC (3.78 g, 19.7 mmol), DMAP (0.22 g, 1.79 mmol) and methylene chloride (36 mL).

$^1$H-NMR (400 MHz, CDCl$_3$) δ(ppm): 1.22-1.48 (m, 6H), 1.58-1.71 (m, 2H), 1.78-1.90 (m, 2H), 2.30-2.38 (m, 2H), 3.33-3.45 (m, 2H), 5.12 (s, 2H), 7.28-7.44 (m, 5H).

Production Example 4

Synthesis of 8-pentyltridecan-1-ol

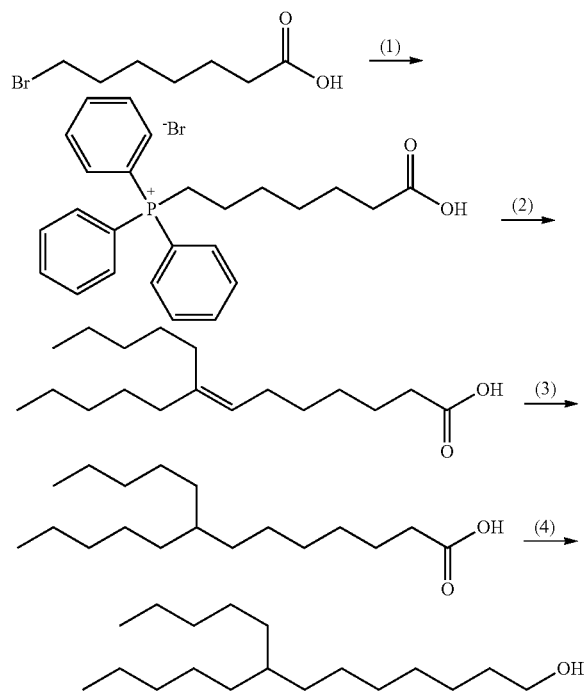

(1) Synthesis of (6-carboxyhexyl)triphenylphosphonium bromide

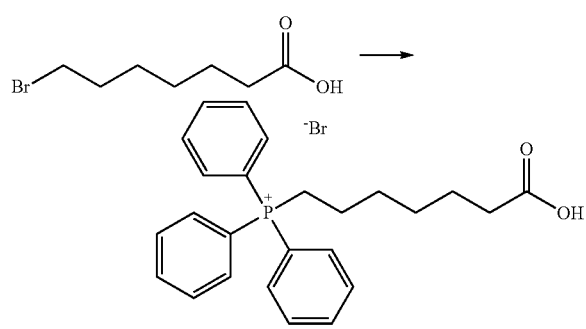

7-Bromoheptanoic acid (2.0 g, 9.57 mmol) and triphenylphosphine (2.5 g, 9.57 mmol) were suspended in acetonitrile (20 mL) and refluxed under heating for 18 hours. After cooled to room temperature, the reaction mixture was concentrated under reduced pressure to obtain the titled compound (4.1 g, 8.66 mmol).

$^1$H-NMR (600 MHz, DMSO-d6) δ(ppm): 1.22-1.59 (m, 8H), 2.12-2.25 (m, 2H), 3.47-3.62 (m, 2H), 7.19-7.28 (m, 2H), 7.34-7.44 (m, 2H), 7.71-7.85 (m, 10H), 7.85-7.94 (m, 3H), 11.97 (br s, 1H).

(2) Synthesis of 8-pentyl-7-tridecenoic acid

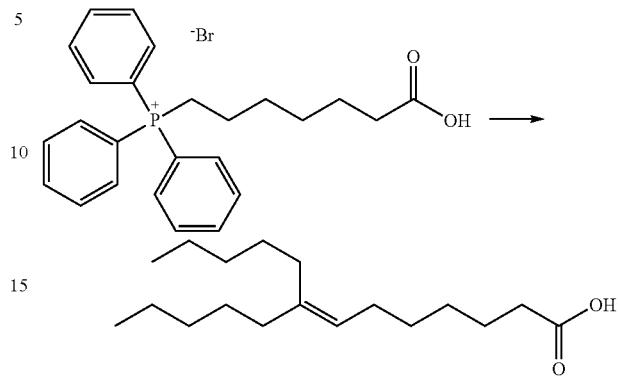

The compound (4.65 g, 9.87 mmol) obtained in Production Example 4-(1) was dissolved in THF (15 mL) and sodium bis(trimethylsilyl)amide/THF solution (1 M, 19.7 mL, 19.7 mmol) was added at room temperature in a nitrogen atmosphere. The reaction solution was heated to 45° C. and then stirred for 30 minutes. A solution of undecan-6-one (1.7 mL, 8.22 mmol) in THF (5 mL) was added dropwise followed by reflux by heating. The reaction mixture was stirred for 22 hours, and then hydrochloric acid (2 M) was carefully added until pH 2. After addition of water (100 mL) and extraction with diethyl ether, the organic layer was dried over anhydrous magnesium sulphate. Following filtration, the solvent was removed by distillation under reduced pressure. The residue was purified by silica gel column chromatography (ethyl acetate/cyclohexane) to obtain a 1:1 mixture (1.36 g) of the titled compound and undecan-6-one.

$^1$H-NMR (600 MHz, DMSO-d6) δ(ppm): 0.80-0.89 (m, 6H), 1.16-1.38 (m, 18H), 1.43-1.53 (m, 2H), 1.89-1.99 (m, 4H), 2.17 (t, J=7.43 Hz, 2H), 5.07 (t, J=6.90 Hz, 1H), 11.83 (br s, 1H).

(3) Synthesis of 8-pentyltridecylic acid

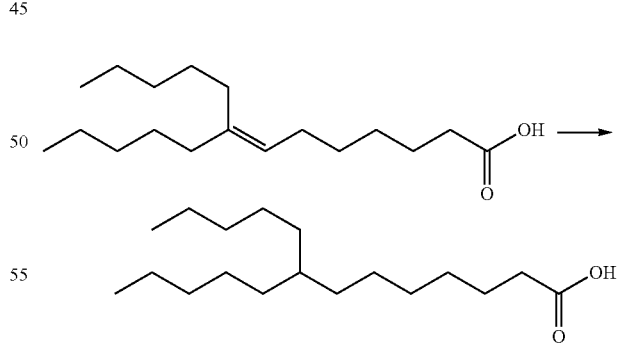

The compound (1.36 g) obtained in Production Example 4-(2) and 10% palladium-carbon (0.06 g, 0.060 mmol) were suspended in ethanol (5 mL), and the suspension was stirred for 18 hours in a hydrogen atmosphere at room temperature under normal pressure. The reaction mixture was filtered through Celite and washed with ethanol. The filtrate was concentrated under reduced pressure to obtain the titled compound (0.60 g, 2.18 mmol).

¹H-NMR (600 MHz, DMSO-d6) δ(ppm): 0.85 (t, J=7.1 Hz, 6H), 1.14-1.32 (m, 25H), 1.42-1.52 (m, 2H), 2.18 (t, J=7.43 Hz, 2H).

(4) Synthesis of 8-pentyltridecan-1-ol

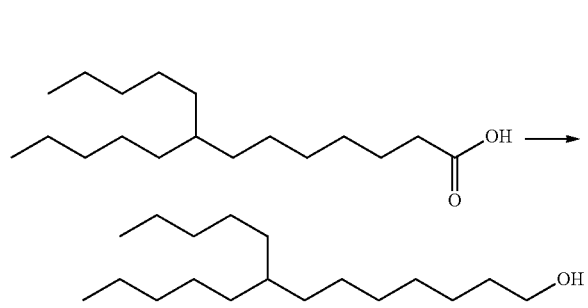

To a lithium aluminium hydride/THF solution (2.4 M, 1.3 mL, 3.15 mmol), in a nitrogen atmosphere, a solution of the compound (1.36 g) obtained in Production Example 4-(3) in THF (5 mL) was added dropwise under ice cooling. After stirring at room temperature for 2 hours, hydrochloric acid (1 M, 8 mL) was added dropwise and the mixture was stirred for 1 hour. The organic layer was extracted with diethyl ether and then washed sequentially with a saturated sodium hydrogen carbonate aqueous solution and a saturated sodium chloride solution and dried over anhydrous magnesium sulphate. Following filtration, the solvent was removed by distillation under reduced pressure. The residue was purified by silica gel column chromatography (ethyl acetate/cyclohexane) to obtain the titled compound (0.28 g, 1.02 mmol).

¹H-NMR (600 MHz, CDCl₃) δ(ppm): 0.88 (t, J=7.24 Hz, 6H), 1.13-1.41 (m, 28H), 1.54-1.60 (m, 2H), 3.59-3.68 (m, 2H).

Production Example 5

Synthesis of 4-nonyltridecan-1-ol

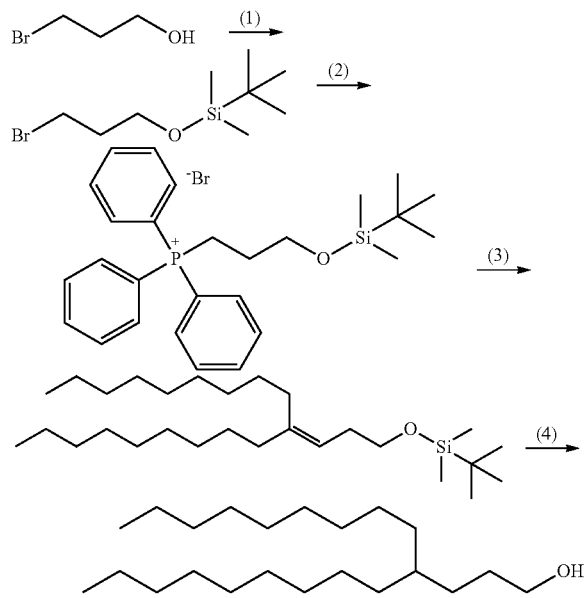

(1) Synthesis of (3-bromopropoxy)(tert-butyl)dimethylsilane

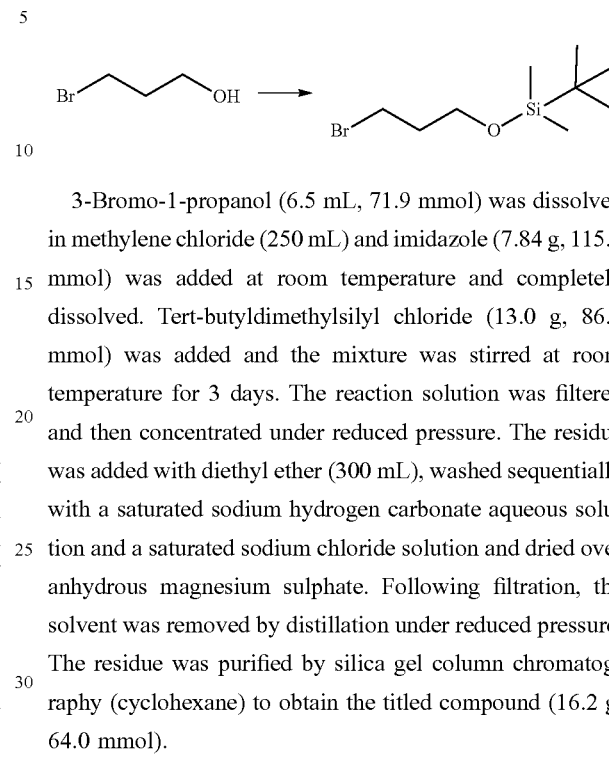

3-Bromo-1-propanol (6.5 mL, 71.9 mmol) was dissolved in methylene chloride (250 mL) and imidazole (7.84 g, 115.0 mmol) was added at room temperature and completely dissolved. Tert-butyldimethylsilyl chloride (13.0 g, 86.3 mmol) was added and the mixture was stirred at room temperature for 3 days. The reaction solution was filtered and then concentrated under reduced pressure. The residue was added with diethyl ether (300 mL), washed sequentially with a saturated sodium hydrogen carbonate aqueous solution and a saturated sodium chloride solution and dried over anhydrous magnesium sulphate. Following filtration, the solvent was removed by distillation under reduced pressure. The residue was purified by silica gel column chromatography (cyclohexane) to obtain the titled compound (16.2 g, 64.0 mmol).

¹H-NMR (600 MHz, CDCl₃) δ(ppm): 0.08 (s, 6H), 0.91 (s, 9H), 2.05 (quin, J=6.05 Hz, 2H), 3.53 (t, J=6.42 Hz, 2H), 3.75 (t, J=5.69 Hz, 2H).

(2) Synthesis of {3-[(tert-butyldimethylsilyl)oxy]propyl}triphenylphosphonium bromide

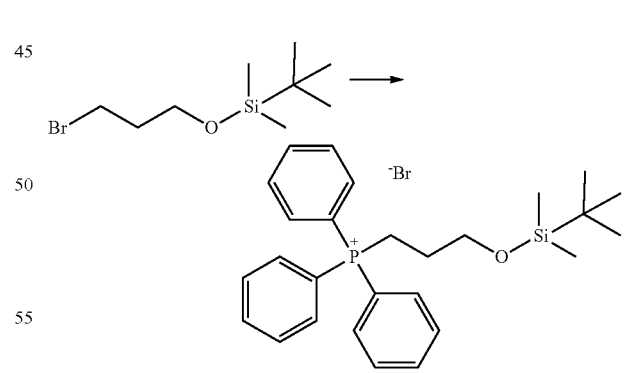

According to the method in Production Example 4-(1), the titled compound (21.2 g, 41.1 mmol) was obtained from the compound (16.2 g, 63.9 mmol) obtained in Production Example 5-(1), triphenylphosphine (16.8 g, 63.9 mmol) and acetonitrile (125 mL).

¹H-NMR (600 MHz, DMSO-d6) δ(ppm): 0.01 (s, 6H), 0.84 (s, 9H), 1.65-1.75 (m, 2H), 3.48-3.57 (m, 2H), 3.69 (t, J=6.14 Hz, 2H), 7.73-7.84 (m, 12H), 7.87-7.93 (m, 3H).

(3) Synthesis of tert-butyldimethyl[(4-nonyl-3-tridecen-1-yl)oxy]silane

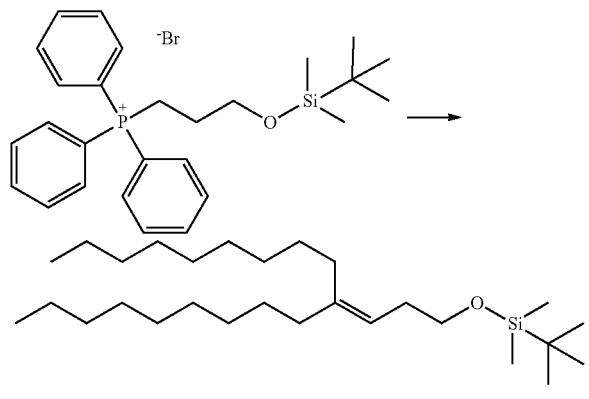

The compound (4.38 g, 8.50 mmol) obtained in Production Example 5-(2) was dissolved in THF (15 mL) and in a nitrogen atmosphere, a sodium bis(trimethylsilyl)amide/THF solution (1 M, 8.5 mL, 8.5 mmol) was added at room temperature. The reaction solution was heated to 45° C. and then stirred for 30 minutes. A solution of nonadecan-10-one (2.0 g, 7.08 mmol) in THF (10 mL) was added dropwise and refluxed under heating for 21 hours. The reaction mixture was cooled to room temperature, then added with diethyl ether and washed sequentially with water and a saturated sodium chloride solution and the organic layer was dried over anhydrous magnesium sulphate. Following filtration, the solvent was removed by distillation under reduced pressure. The residue was purified by silica gel column chromatography (cyclohexane) to obtain the titled compound (1.16 g).

$^1$H-NMR (600 MHz, CDCl$_3$) δ(ppm): 0.07 (s, 6H), 0.90 (m, 15H), 1.21-1.41 (m, 28H), 1.92-2.04 (m, 4H), 2.24 (q, J=7.34 Hz, 2H), 3.58 (t, J=7.24 Hz, 2H), 5.09 (t, J=7.15 Hz, 1H).

(4) Synthesis of 4-nonyltridecan-1-ol

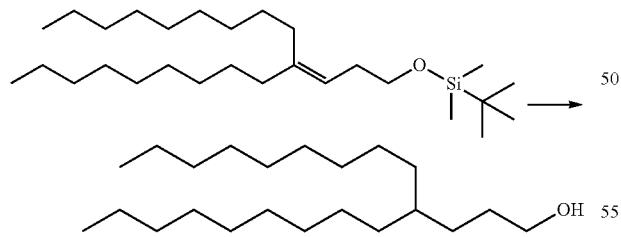

The compound (1.16 g, 2.64 mmol) obtained in Production Example 5-(3) and 10% palladium-carbon (0.28 g, 0.26 mmol) were suspended in ethyl acetate (10 mL) and acetic acid (0.15 mL, 2.64 mmol) and the suspension was stirred in a hydrogen atmosphere at room temperature for 18 hours. The reaction mixture was filtered through Celite and washed with ethanol, and the filtrate was then concentrated under reduced pressure. The residue was purified by silica gel column chromatography (ethyl acetate/cyclohexane) to obtain the titled compound (0.35 g, 1.08 mmol).

$^1$H-NMR (600 MHz, DMSO-d6) δ(ppm): 0.80-0.90 (m, 6H), 1.13-1.30 (m, 35H), 1.32-1.39 (m, 2H), 3.32-3.38 (m, 2H), 4.30 (t, J=5.23 Hz, 1H).

Production Example 6

Synthesis of 4-heptylundecan-1-ol

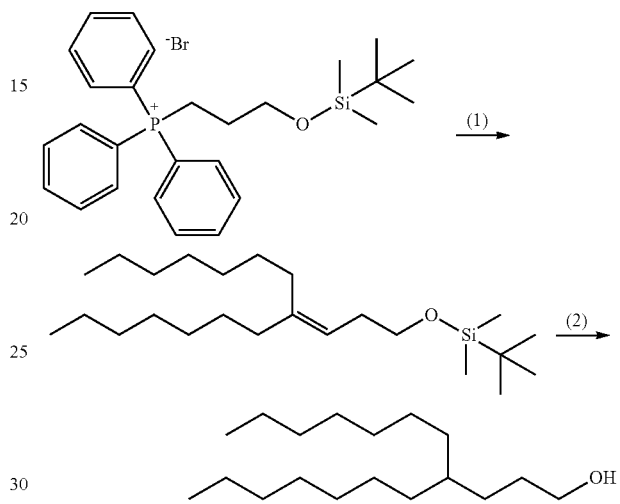

(1) Synthesis of tert-butyl[(4-heptyl-3-undecen-1-yl)oxy]dimethylsilane

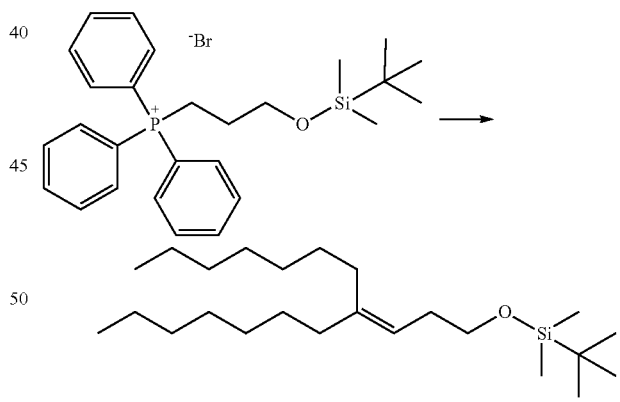

According to the method in Production Example 5-(3), the titled compound (0.83 g, 2.17 mmol) was obtained from {3-[(tert-butyldimethylsilyl)oxy]propyl}triphenylphosphonium bromide (3.0 g, 5.83 mmol), THF (10 mL), sodium bis(trimethylsilyl)amide/THF solution (1 M, 5.8 mL, 5.8 mmol) and pentadecan-8-one (1.1 g, 4.86 mmol).

$^1$H-NMR (600 Hz, CDCl$_3$) δ(ppm): 0.07 (s, 6H), 0.84-0.95 (m, 15H), 0.89 (s, 1H), 1.21-1.41 (m, 20H), 1.92-2.05 (m, 4H), 2.24 (q, J=7.34 Hz, 2H), 3.58 (t, J=7.24 Hz, 2H), 5.09 (t, J=7.24 Hz, 1H).

(2) Synthesis of 4-heptylundecan-1-ol

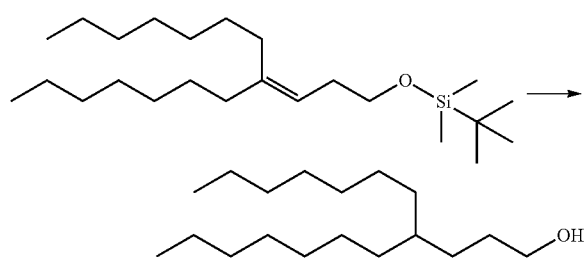

According to the method in Production Example 5-(4), the titled compound (0.42 g, 1.56 mmol) was obtained from the compound (0.83 g, 2.17 mmol) obtained in Production Example 6-(1), 10% palladium-carbon (0.23 g, 0.22 mmol), ethyl acetate (10 mL) and acetic acid (0.25 mL, 4.35 mmol).

$^1$H-NMR (600 MHz, DMSO-d6) δ(ppm): 0.82-0.89 (m, 6H), 1.14-1.31 (m, 27H), 1.33-1.39 (m, 2H), 3.32-3.38 (m, 2H), 4.30 (t, J=5.14 Hz, 1H).

Production Example 7

Synthesis of 4-pentylnonan-1-ol

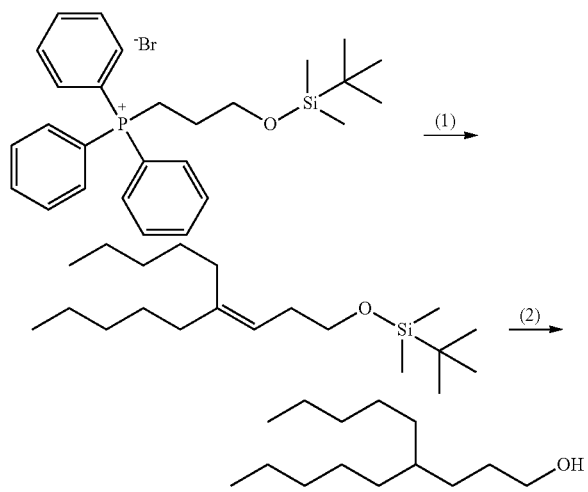

(1) Synthesis of tert-butyldimethylsilyl[(4-pentyl-3-nonen-1-yl)oxy]silane

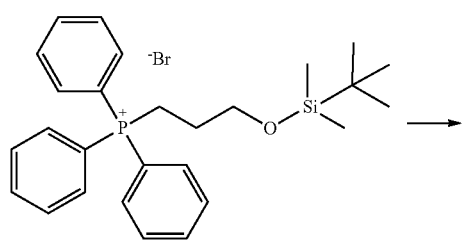

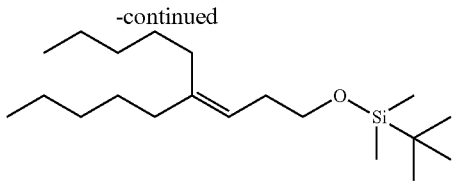

According to the method in Production Example 5-(3), the titled compound (1.16 g) was obtained from {3-[(tert-butyldimethylsilyl)oxy]propyl}triphenylphosphonium bromide (5.0 g, 9.72 mmol), THF (4 mL), sodium bis(trimethylsilyl)amide/THF solution (1 M, 9.7 mL, 9.7 mmol) and undecan-6-one (1.7 mL, 8.10 mmol).

$^1$H-NMR (600 Hz, CDCl$_3$) δ(ppm): 0.07 (s, 6H), 0.90 (m, 15H), 1.19-1.43 (m, 13H), 1.92-2.05 (m, 4H), 2.21-2.29 (m, 2H), 3.58 (t, J=7.24 Hz, 2H), 5.10 (t, J=7.15 Hz, 1H).

(2) Synthesis of 4-pentylnonan-1-ol

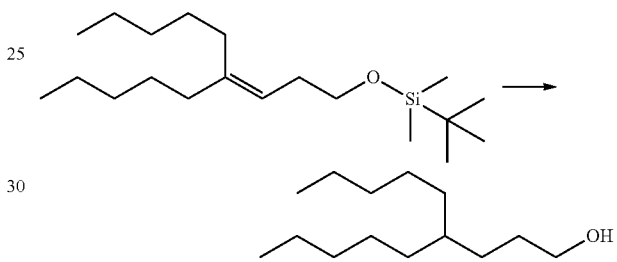

According to the method in Production Example 5-(4), the titled compound (0.22 g, 1.02 mmol) was obtained from the compound (1.12 g, 3.43 mmol) obtained in Production Example 7-(1), 10% palladium-carbon (0.37 g, 0.34 mmol), ethyl acetate (15 mL) and acetic acid (0.39 mL, 6.86 mmol).

$^1$H-NMR (600 MHz, DMSO-d6) δ(ppm): 0.87-0.93 (m, 6H), 1.18-1.36 (m, 19H), 1.37-1.45 (m, 2H), 3.36-3.42 (m, 2H), 4.35 (t, J=5.23 Hz, 1H).

Production Example 8

Synthesis of benzyl 4-bromobutanoate

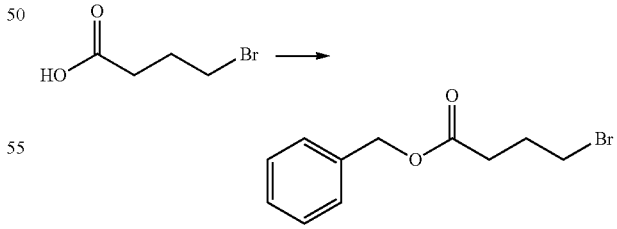

Benzyl alcohol (2.84 mL, 27.3 mmol), 4-bromobutanoic acid (5.01 g, 30.0 mmol) and DMAP (0.33 g, 2.73 mmol) were dissolved in methylene chloride (50 mL), added with EDC (6.5 g, 34.1 mmol) under ice cooling and stirred at room temperature for 2.5 hours. The reaction mixture was concentrated under reduced pressure and then dissolved in diethyl ether. The solution was washed sequentially with a saturated sodium hydrogen carbonate aqueous solution, water and a 10% citric acid aqueous solution and dried over anhydrous magnesium sulphate. Following filtration, the solvent was removed by distillation under reduced pressure to obtain the titled compound (6.41 g, 24.9 mmol).

$^1$H-NMR (600 MHz, CDCl$_3$) δ(ppm): 2.20 (quin, J=6.83 Hz, 2H), 2.56 (t, J=7.15 Hz, 2H), 3.46 (t, J=6.51 Hz, 2H), 5.13 (s, 2H), 7.28-7.42 (m, 5H).

Production Example 9

Synthesis of benzyl 6-bromohexanoate

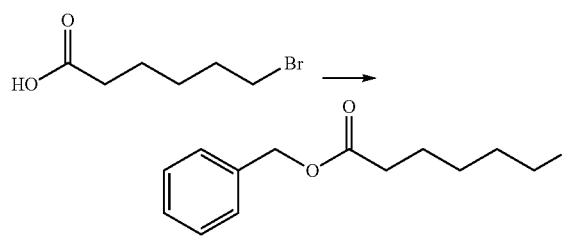

According to the method in Production Example 8, the titled compound (5.43 g, 19.0 mmol) was obtained from benzyl alcohol (1.93 mL, 18.5 mmol), 6-bromohexanoic acid (4.33 g, 22.2 mmol), DMAP (0.23 g, 1.85 mmol), EDC (4.43 g, 23.1 mmol) and methylene chloride (35 mL).

$^1$H-NMR (600 MHz, CDCl$_3$) δ(ppm): 1.44-1.51 (m, 2H), 1.64-1.72 (m, 2H), 1.83-1.90 (m, 2H), 2.38 (t, J=7.43 Hz, 2H), 3.39 (t, J=6.69 Hz, 2H), 5.12 (s, 2H), 7.30-7.40 (m, 5H).

Production Example 10

Synthesis of (1R,5S,6r)-3-methyl-3-azabicyclo[3.1.0]hexane-6-carboxylic acid hydrochloride

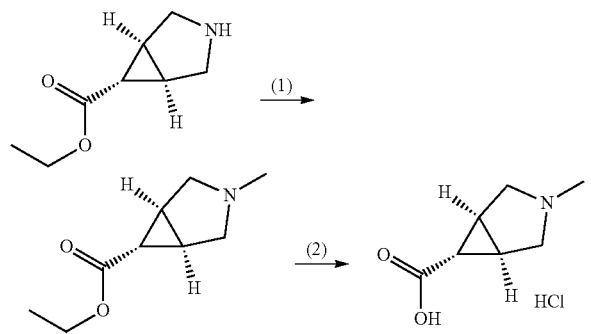

(1) Synthesis of (1R,5S,6r)-ethyl 3-methyl-3-azabicyclo[3.1.0]hexane-6-carboxylate (1R,5S,6r)-Ethyl 3-azabicyclo[3.1.0]hexane-6-carboxylate (CAS 174456-77-0) (0.89 g, 5.74 mmol) was dissolved in THF (20 mL), to which acetic acid (0.49 mL, 8.6 mmol) and a formaldehyde solution (11.7 mL, 161.5 mol) were sequentially added at room temperature, and the mixture was stirred for 30 minutes. Sodium tri(acetoxy)borohydride (2.43 g, 11.5 mmol) was added and the mixture was stirred at room temperature for 3 hours. The reaction mixture was concentrated under reduced pressure, then added with a saturated sodium hydrogen carbonate aqueous solution and extracted with methylene chloride. The mixture was dried over anhydrous sodium sulphate. Following filtration, the solvent was removed by distillation under reduced pressure. The residue was purified by silica gel column chromatography (methylene chloride/methanol) to obtain the titled compound (0.70 g, 4.14 mmol).

$^1$H-NMR (400 MHz, CDCl$_3$) δ(ppm): 1.25 (t, J=7.2 Hz, 3H), 1.94 (br s, 2H), 2.01 (br s, 1H), 2.29 (s, 3H), 2.35 (d, J=9.2 Hz, 2H), 3.05 (d, J=9.2 Hz, 2H), 4.09 (q, J=7.2 Hz, 2H).

(2) Synthesis of (1R,5S,6r)-3-methyl-3-azabicyclo[3.1.0]hexane-6-carboxylic acid hydrochloride Concentrated hydrochloric acid (10 mL) was added to the compound (0.60 g, 3.55 mmol) obtained in Production Example 10-(1) and stirred at 70° C. for 12 hours. The reaction mixture was concentrated under reduced pressure to obtain the titled compound (0.52 g, 3.05 mmol).

$^1$H-NMR (400 MHz, DMSO-d6) δ(ppm): 2.14 (br s, 2H), 2.25 (br s, 1H), 2.74 (br s, 3H), 3.25-3.37 (m, 2H), 3.56-3.67 (m, 2H), 10.91 (br s, 1H), 12.49 (br s, 1H).

Production Example 11

Synthesis of (1R,5S,6s)-3-methyl-3-azabicyclo[3.1.0]hexane-6-carboxylic acid hydrochloride

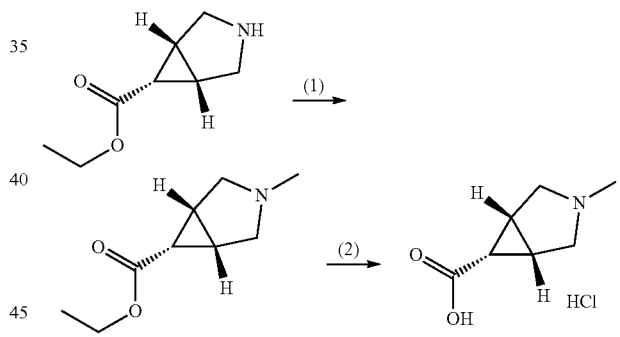

(1) Synthesis of (1R,5S,6s)-ethyl 3-methyl-3-azabicyclo[3.1.0]hexane-6-carboxylate According to the method in Production Example 10-(1), the titled compound (2.5 g, 14.8 mmol) was obtained from (1R,5S,6s)-ethyl 3-azabicyclo[3.1.0]hexane-6-carboxylate (CAS 1144099-54-6) (2.5 g, 16.1 mmol), acetic acid (1.4 mL, 24.2 mmol), a formaldehyde solution (10.0 mL, 134.3 mmol), sodium tri(acetoxy)borohydride (6.8 g, 32.2 mmol) and THF (50 mL).

$^1$H-NMR (400 MHz, CDCl$_3$) δ(ppm): 1.23 (t, J=7.1 Hz, 3H), 1.48-1.68 (m, 3H), 2.22 (s, 3H), 2.33 (br d, J=8.8 Hz, 2H), 3.02 (d, J=8.8 Hz, 2H), 4.10 (q, J=7.1 Hz, 2H).

(2) Synthesis of (1R,5S,6s)-3-methyl-3-azabicyclo[3.1.0]hexane-6-carboxylic acid hydrochloride According to the method in Production Example 10-(2), the titled compound (350 mg, 1.97 mmol) was obtained from the compound (500 mg, 2.96 mmol) obtained in Production Example 10-(2) and concentrated hydrochloric acid (10 mL).

$^1$H-NMR (400 MHz, DMSO-d6) δ(ppm): 1.88-1.94 (m, 0.45H), 1.94-2.00 (m, 0.55H), 2.35-2.45 (m, 2H), 2.68 (br s, 1.65H), 2.67 (br s, 1.35H), 3.08-3.18 (m, 1.1H), 3.45-3.57 (m, 0.9H), 3.73-3.88 (m, 2H), 9.16 (br s, 1H), 11.52 (br s, 1H).

Synthesis of Cationic Lipid (1)

Example A-1

2-{9-[(2-Butyloctyl)oxy]-9-oxononyl}dodecyl 1-methylpiperidine-4-carboxylate (Cationic Lipid 1)

compound (573 mg, 1.41 mmol) obtained in Production Example 1 was added with 1,4-dioxane (1 mL) and the mixture was stirred at 70° C. for 3 hours and 95° C. for 15 hours. The reaction mixture was cooled in an ice water bath, added with a saturated ammonium chloride aqueous solution and extracted with n-heptane. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (490 mg, 0.91 mmol).

$^1$H-NMR (400 MHz, CDCl$_3$) δ(ppm): 0.80-0.98 (m, 6H), 1.18-1.38 (m, 24H), 1.39-1.54 (m, 2H), 1.46 (s, 18H),

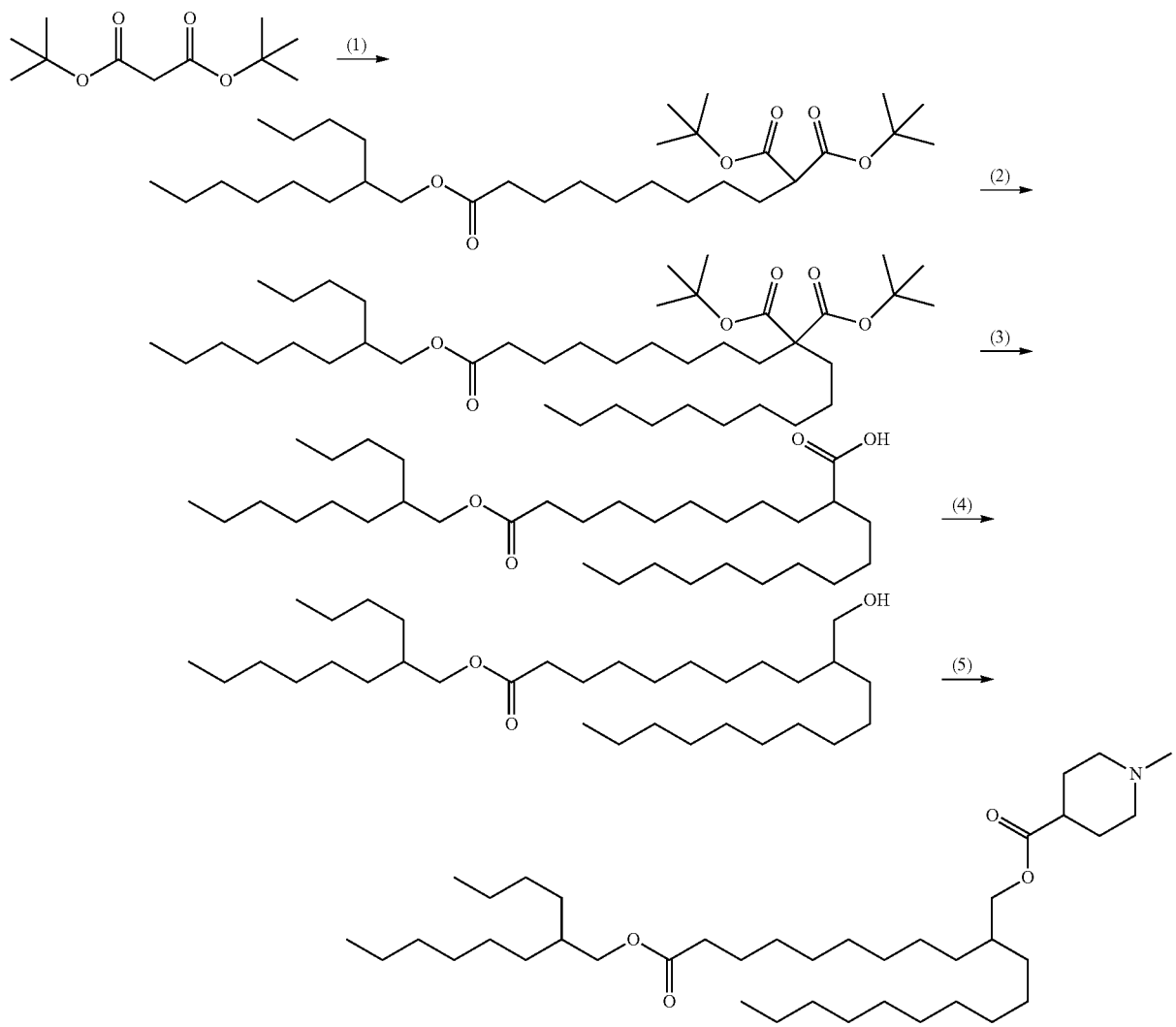

(1) Synthesis of 1,1-di-tert-butyl 9-(2-butyloctyl) nonane-1,1,9-tricarboxylate

60% Sodium hydride (59 mg, 1.48 mmol) was suspended in 1,4-dioxane (6.5 mL), to which di-tert-butyl malonate (0.30 mL, 1.35 mmol) was gradually added at room temperature, and the mixture was stirred for 20 minutes. The 1.55-1.69 (m, 3H), 1.71-1.87 (m, 2H), 2.24-2.35 (m, 2H), 3.06-3.15 (m, 1H), 3.91-4.02 (m, 2H).

(2) Synthesis of 9,9-di-tert-butyl 1-(2-butyloctyl) nonadecane-1,9,9-tricarboxylate The compound (490 mg, 0.91 mmol) obtained in Example A-1-(1) was dissolved in 1,4-dioxane (4 mL), to which 60% sodium hydride (47 mg, 1.18 mmol) was added under water cooling, and the mixture was stirred at room temperature for 5 minutes. 1-Iododecane (0.39 mL, 1.81 mmol) was added and the mixture was stirred at 80° C. for 15 hours. The reaction mixture was cooled in an ice water bath, added with a saturated ammonium chloride aqueous solution and extracted with n-heptane. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (450 mg, 0.66 mmol).

$^1$H-NMR (400 MHz, CDCl$_3$) δ(ppm): 0.80-0.96 (m, 9H), 1.05-1.36 (m, 40H), 1.39-1.49 (m, 2H), 1.44 (s, 18H), 1.53-1.68 (m, 3H), 1.70-1.82 (m, 4H), 2.23-2.34 (m, 2H), 3.92-4.01 (m, 2H).

(3) Synthesis of 2-{9-[(2-butyloctyl)oxy]-9-oxononyl}dodecanoic acid

The compound (450 mg, 0.66 mmol) obtained in Example A-1-(2) was dissolved in methylene chloride (2 mL), to which TFA (1 mL) was added under ice cooling and the mixture was stirred at room temperature for 1.5 hours. To the reaction mixture was added toluene and the solvent was distilled off under reduced pressure. Addition and distillation of toluene was repeated twice to dry the reaction, thereby obtaining a crude product of 2-{9-[(2-butyloctyl)oxy]-9-oxononyl}-2-decylmalonic acid. The obtained crude product was dissolved in xylene (5 mL) and the solution was stirred at 150° C. for 8 hours. The reaction mixture was cooled to room temperature and concentrated under reduced pressure. The obtained residue was purified by column chromatography (n-heptane/ethyl acetate) to obtain the titled compound (240 mg, 0.46 mmol).

$^1$H-NMR (400 MHz, CDCl$_3$) δ(ppm): 0.80-0.97 (m, 9H), 1.16-1.70 (m, 49H), 2.22-2.41 (m, 3H), 3.92-4.02 (m, 2H).

(4) Synthesis of 2-butyloctyl 10-(hydroxymethyl)icosanoate

The compound (240 mg, 0.46 mmol) obtained in Example A-1-(3) was dissolved in THF (4 mL), to which 0.92M borane-THF complex (0.75 mL, 0.69 mmol) was added dropwise at −15° C., and the mixture was stirred at 0° C. for 2 hours. A saturated sodium hydrogen carbonate aqueous solution was added and the mixture was stirred at room temperature for 5 minutes and extracted with ethyl acetate. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (197 mg, 0.39 mmol).

$^1$H-NMR (400 MHz, CDCl$_3$) δ(ppm): 0.80-0.98 (m, 9H), 1.10-1.39 (m, 46H), 1.39-1.50 (m, 1H), 1.54-1.69 (m, 4H), 2.23-2.36 (m, 2H), 3.48-3.59 (m, 2H), 3.92-4.02 (m, 2H).

(5) Synthesis of 2-({9-[(2-butyloctyl)oxy]-9-oxononyl}dodecyl 1-methylpiperidine-4-carboxylate The compound (38 mg, 0.074 mmol) obtained in Example A-1-(4), DIPEA (0.054 mL, 0.31 mmol), 1-methyl-piperidine-4-carboxylic acid hydrochloride (27 mg, 0.15 mmol) and DMAP (1.8 mg, 0.015 mmol) were dissolved in methylene chloride (0.8 mL), to which EDC (31 mg, 0.16 mmol) was added under ice cooling, and the mixture was stirred at room temperature for 15 hours. The reaction mixture was added with a saturated sodium hydrogen carbonate aqueous solution and extracted with chloroform. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate/methanol) to obtain the titled compound (38 mg, 0.060 mmol).

$^1$H-NMR (400 MHz, CDCl$_3$) δ(ppm): 0.77-0.97 (m, 9H), 1.13-1.41 (m, 46H), 1.50-1.69 (m, 4H), 1.69-1.85 (m, 2H), 1.85-2.09 (m, 4H), 2.18-2.35 (m, 3H), 2.27 (s, 3H), 2.72-2.88 (m, 2H), 3.90-4.03 (m, 4H).

Synthesis of Cationic Lipid (2)

Example A-2

2-{9-Oxo-9-[(3-pentyloctyl)oxy]nonyl}dodecyl 1-methylpiperidine-4-carboxylate (Cationic Lipid 2)

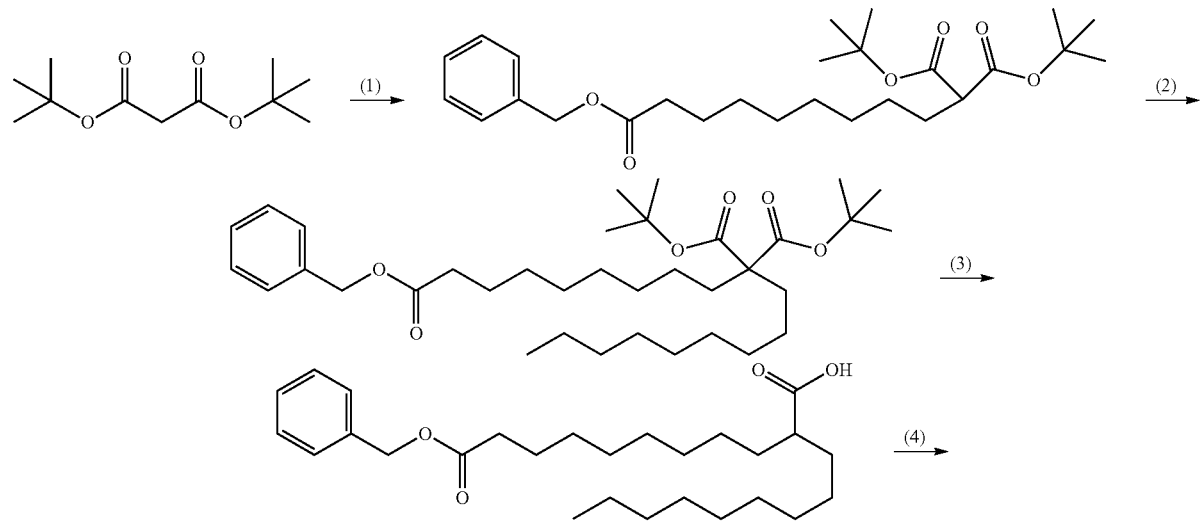

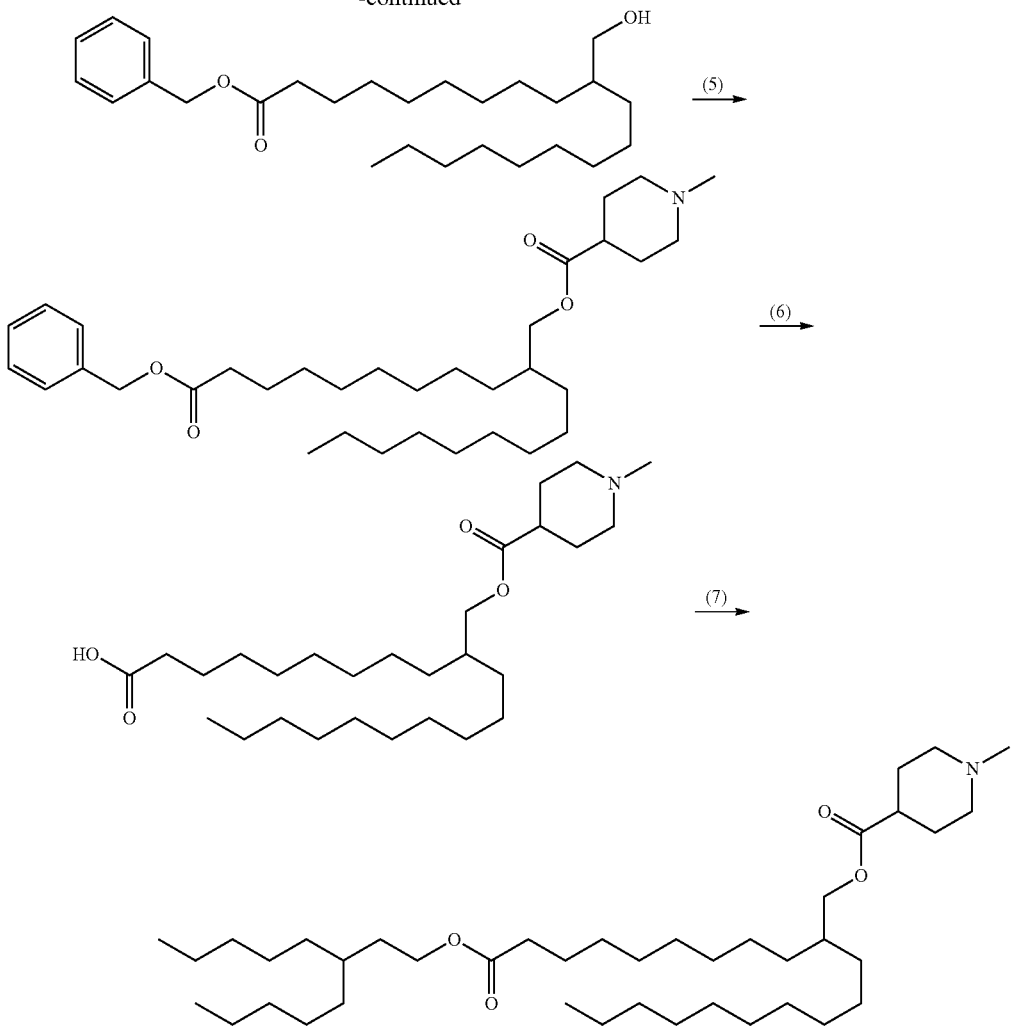

(1) Synthesis of 9-benzyl 1,1-di-tert-butyl nonane-1,1,9-tricarboxylate

60% Sodium hydride (83 mg, 2.07 mmol) was suspended in 1,4-dioxane (9.4 mL), to which di-tert-butyl malonate (0.42 mL, 1.88 mmol) was gradually added at room temperature, and the mixture was stirred for 10 minutes. The compound (650 mg, 1.99 mmol) obtained in Production Example 2 was added and the mixture was stirred at 95° C. for 13 hours. The reaction mixture was cooled in an ice water bath, added with a saturated ammonium chloride aqueous solution and extracted with n-heptane. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (536 mg, 1.16 mmol).

(2) Synthesis of 1-benzyl 9,9-di-tert-butyl nonadecane-1,9,9-tricarboxylate

According to the method in Example A-1-(2), the titled compound (470 mg, 0.78 mmol) was obtained from the compound (590 mg, 1.28 mmol) obtained in Example A-2-(1), 1-iododecane (0.54 mL, 2.55 mmol), 65% sodium hydride (71 mg, 1.91 mmol) and 1,4-dioxane (5 mL).

$^1$H-NMR (400 MHz, CDCl$_3$) δ(ppm): 0.83-0.93 (m, 3H), 1.05-1.36 (m, 26H), 1.44 (s, 18H), 1.57-1.68 (m, 2H), 1.71-1.82 (m, 4H), 2.29-2.39 (m, 2H), 5.11 (s, 2H), 7.28-7.42 (m, 5H).

(3) Synthesis of 2-[9-(benzyloxy)-9-oxononyl]dodecanoic acid

According to the method in Example A-1-(3), the titled compound (286 mg, 0.64 mmol) was obtained from the compound (470 mg, 0.78 mmol) obtained in Example A-2-(2), methylene chloride (2 mL), TFA (1 mL) and xylene (2 mL).

$^1$H-NMR (400 MHz, CDCl$_3$) δ(ppm): 0.81-0.95 (m, 3H), 1.18-1.37 (m, 26H), 1.39-1.52 (m, 2H), 1.54-1.69 (m, 4H), 2.28-2.41 (m, 3H), 5.11 (s, 2H), 7.28-7.40 (m, 5H).

(4) Synthesis of benzyl 10-(hydroxymethyl)icosanoate

According to the method in Example A-1-(4), the titled compound (223 mg, 0.52 mmol) was obtained from the compound (285 mg, 0.64 mmol) obtained in Example A-2-(3), 0.92M borane-THF complex (1.0 mL, 0.96 mmol) and THF (3.2 mL).

$^1$H-NMR (400 MHz, CDCl$_3$) δ(ppm): 0.81-0.95 (m, 3H), 1.12-1.38 (m, 31H), 1.39-1.50 (m, 1H), 1.58-1.72 (m, 2H), 2.23-2.36 (m, 2H), 3.48-3.59 (m, 2H), 5.11 (s, 2H), 7.28-7.41 (m, 5H).

(5) Synthesis of 2-[9-(benzyloxy)-9-oxononyl]dodecyl 1-methylpiperidine-4-carboxylate According to the method in Example A-1-(5), the titled compound (128 mg, 0.23 mmol) was obtained from the compound (114 mg, 0.26 mmol) obtained in Example A-2-(4), 1-methyl-piperidine-4-carboxylic acid hydrochloride (95 mg, 0.53 mmol), EDC (111 mg, 0.58 mmol), DIPEA (0.090 mL, 0.53 mmol), DMAP (6.4 mg, 0.053 mmol) and methylene chloride (1.3 mL).

$^1$H-NMR (400 MHz, CDCl$_3$) δ(ppm): 0.81-0.96 (m, 3H), 1.15-1.41 (m, 31H), 1.52-1.70 (m, 2H), 1.70-1.84 (m, 2H), 1.85-2.06 (m, 4H), 2.18-2.40 (m, 3H), 2.27 (s, 3H), 2.73-2.89 (m, 2H), 3.92-4.03 (m, 2H), 5.12 (s, 2H), 7.28-7.44 (m, 5H).

(6) Synthesis of 10-{[(1-methylpiperidine-4-carbonyl)oxy]methyl}icosanoic acid

The compound (127 mg, 0.23 mmol) obtained in Example A-2-(5) was dissolved in ethyl acetate (2 mL), to which 10% palladium-carbon (24 mg, containing 50% water) was added at room temperature, and the mixture was stirred in a hydrogen atmosphere under normal pressure for 3 hours. The reaction solution was filtered and washed with ethyl acetate. The filtrate was concentrated under reduced pressure, the obtained residue was purified by column chromatography (chloroform/methanol) to obtain the titled compound (94 mg, 0.20 mmol).

$^1$H-NMR (400 MHz, CDCl$_3$) δ(ppm): 0.81-0.95 (m, 3H), 1.12-1.44 (m, 31H), 1.53-1.71 (m, 2H), 1.74-1.95 (m, 2H), 1.97-2.10 (m, 2H), 2.11-2.37 (m, 5H), 2.40 (s, 3H), 3.11-3.28 (m, 2H), 3.79-3.92 (m, 1H), 4.14-4.25 (m, 1H).

(7) Synthesis of 2-{9-oxo-9-[(3-pentyloctyl)oxy]nonyl}dodecyl 1-methylpiperidine-4-carboxylate According to the method in Production Example 2, the titled compound (103 mg, 0.16 mmol) was obtained from the compound (93 mg, 0.20 mmol) obtained in Example A-2-(6), 3-pentyloctan-1-ol (CAS 1443519-63-8) (60 mg, 0.30 mmol), EDC (42 mg, 0.22 mmol), DMAP (4.9 mg, 0.040 mmol) and methylene chloride (1.5 mL).

$^1$H-NMR (400 MHz, CDCl$_3$) δ(ppm): 0.82-0.95 (m, 9H), 1.14-1.46 (m, 46H), 1.50-1.68 (m, 6H), 1.70-1.84 (m, 2H), 1.85-2.06 (m, 4H), 2.19-2.33 (m, 3H), 2.27 (s, 3H), 2.74-2.87 (m, 2H), 3.93-4.02 (m, 2H), 4.03-4.14 (m, 2H).

Synthesis of Cationic Lipid (3)

Example A-3

2-Nonyl-11-oxo-11-[(3-pentyloctyl)oxy]undecyl 1-methylpiperidine-4-carboxylate (Cationic Lipid 3)

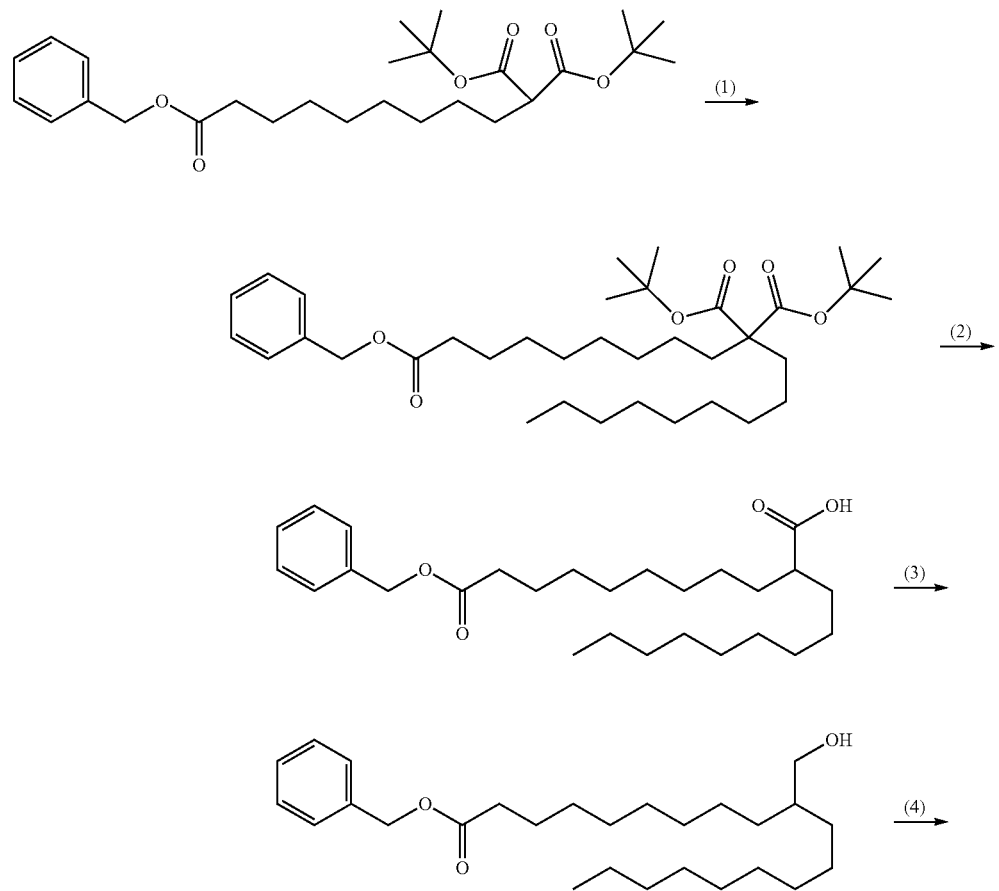

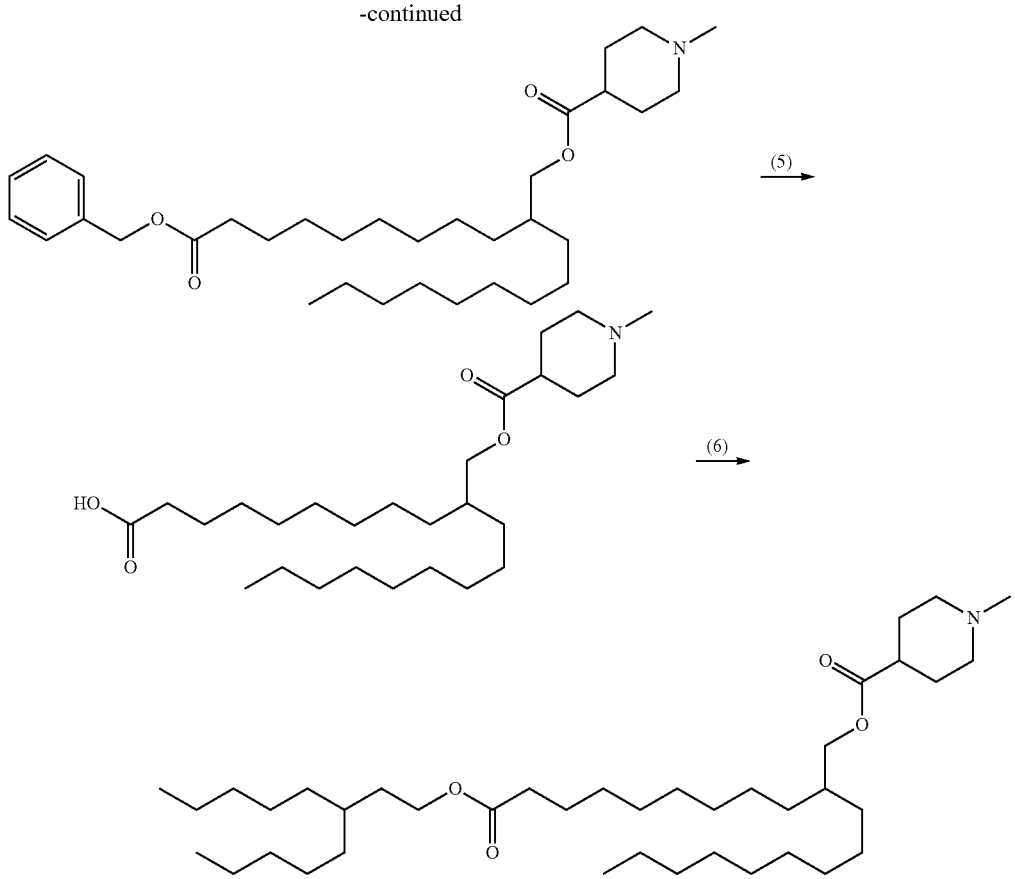

(1) Synthesis of 1-benzyl 9,9-di-tert-butyl octadecane-1,9,9-tricarboxylate

The compound (536 mg, 1.16 mmol) obtained in Example A-2-(1) was dissolved in THF (6 mL), to which 60% sodium hydride (58 mg, 1.45 mmol) was added under water cooling, and the mixture was stirred at room temperature for 5 minutes. 1-Iodononane (0.23 mL, 1.16 mmol) was added and the mixture was stirred at 80° C. for 20 hours. The reaction mixture was cooled in an ice water bath, added with a saturated ammonium chloride aqueous solution and extracted with n-heptane. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (340 mg, 0.577 mmol).

$^1$H-NMR (400 MHz, CDCl$_3$) δ(ppm): 0.82-0.92 (m, 3H), 1.03-1.36 (m, 24H), 1.44 (s, 18H), 1.57-1.68 (m, 2H), 1.71-1.81 (m, 4H), 2.28-2.40 (m, 2H), 5.11 (s, 2H), 7.28-7.41 (m, 5H).

(2) Synthesis of 1-(benzyloxy)-2-nonyl-11-oxoundecanoic acid

According to the method in Example A-1-(3), the titled compound (96 mg, 0.22 mmol) was obtained from the compound (340 mg, 0.58 mmol) obtained in Example A-3-(1), methylene chloride (2 mL), TFA (1 mL) and xylene (2 mL).

$^1$H-NMR (400 MHz, CDCl$_3$) δ(ppm): 0.80-0.95 (m, 3H), 1.12-1.74 (m, 30H), 2.28-2.41 (m, 3H), 5.11 (s, 2H), 7.28-7.40 (m, 5H).

(3) Synthesis of benzyl 10-(hydroxymethyl)nonadecanoate

According to the method in Example A-1-(4), the titled compound (80 mg, 0.19 mmol) was obtained from the compound (96 mg, 0.22 mmol) obtained in Example A-3-(2), 0.92M borane-THF complex (0.36 mL, 0.33 mmol) and THF (1.1 mL).

$^1$H-NMR (400 MHz, CDCl$_3$) δ(ppm): 0.81-0.94 (m, 3H), 1.09-1.38 (m, 29H), 1.38-1.50 (m, 1H), 1.58-1.71 (m, 2H), 2.30-2.40 (m, 2H), 3.48-3.58 (m, 2H), 5.11 (s, 2H), 7.29-7.42 (m, 5H).

(4) Synthesis of 11-(benzyloxy)-2-nonyl-11-oxoundecyl 1-methylpiperidine-4-carboxylate According to the method in Example A-1-(5), the titled compound (97 mg, 0.18 mmol) was obtained from the compound (80 mg, 0.19 mmol) obtained in Example A-3-(3), 1-methyl-piperidine-4-carboxylic acid hydrochloride (69 mg, 0.38 mmol), EDC (81 mg, 0.42 mmol), DIPEA (0.066 mL, 0.38 mmol), DMAP (4.7 mg, 0.038 mmol) and methylene chloride (1.0 mL).

$^1$H-NMR (400 MHz, CDCl$_3$) δ(ppm): 0.83-0.94 (m, 3H), 1.15-1.39 (m, 29H), 1.52-1.70 (m, 2H), 1.70-1.85 (m, 2H), 1.85-2.07 (m, 4H), 2.19-2.40 (m, 3H), 2.27 (s, 3H), 2.73-2.88 (m, 2H), 3.94-4.02 (m, 2H), 5.12 (s, 2H), 7.28-7.43 (m, 5H).

(5) Synthesis of 10-{[(1-methylpiperidine-4-carbonyl)oxy]methyl}nonadecanoic acid According to the method in Example A-2-(6), the compound (96 mg, 0.18 mmol) obtained in Example A-3-(4) was dissolved in ethyl acetate (2 mL), to which 10% palladium-carbon (19 mg, containing 50% water) was added at room temperature, and the mixture was stirred in a hydrogen atmosphere under normal pressure for 3 hours. The reaction solution was filtered and washed with ethyl acetate. The filtrate was concentrated under reduced pressure, the obtained residue was purified by column chromatography (chloroform/methanol) to obtain the titled compound (74 mg, 0.163 mmol).

$^1$H-NMR (400 MHz, CDCl$_3$) δ(ppm): 0.81-0.95 (m, 3H), 1.12-1.44 (m, 29H), 1.53-1.71 (m, 2H), 1.74-1.94 (m, 2H), 1.98-2.08 (m, 2H), 2.08-2.38 (m, 5H), 2.39 (s, 3H), 3.10-3.30 (m, 2H), 3.80-3.91 (m, 1H), 4.14-4.25 (m, 1H).

(6) Synthesis of 2-nonyl-11-oxo-11-[(3-pentyloctyl)oxy]undecyl 1-methylpiperidine-4-carboxylate According to the method in Production Example 2, the titled compound (81 mg, 0.13 mmol) was obtained from the compound (74 mg, 0.16 mmol) obtained in Example A-3-(5), 3-pentyloctan-1-ol (CAS 1443519-63-8) (49 mg, 0.25 mmol), EDC (38 mg, 0.20 mmol), DMAP (4.0 mg, 0.033 mmol) and methylene chloride (1.2 mL).

$^1$H-NMR (400 MHz, CDCl$_3$) δ(ppm): 0.81-0.95 (m, 9H), 1.15-1.47 (m, 44H), 1.50-1.68 (m, 6H), 1.70-1.84 (m, 2H), 1.84-2.06 (m, 4H), 2.18-2.33 (m, 3H), 2.27 (s, 3H), 2.73-2.87 (m, 2H), 3.94-4.01 (m, 2H), 4.04-4.12 (m, 2H).

Synthesis of Cationic Lipid (4)

Example A-4

Bis(3-pentyloctyl) 9-{[(1-methylpiperidine-4-carbonyl)oxy]methyl}heptadecanedioate (Cationic Lipid 4)

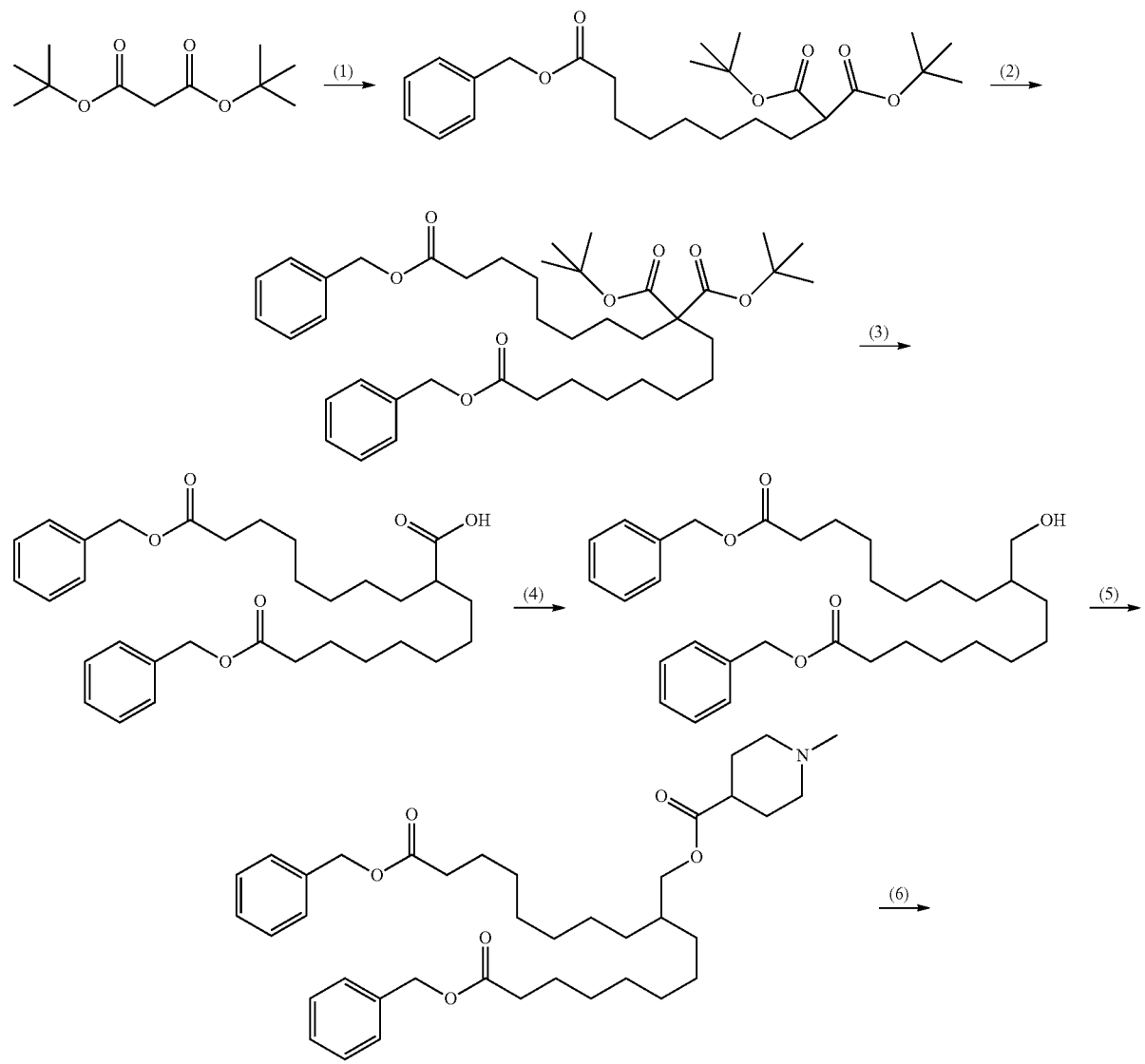

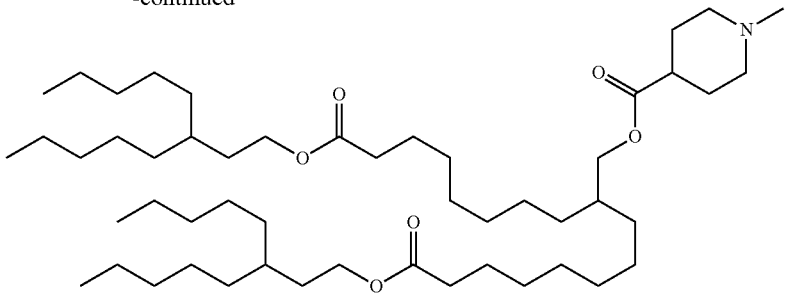

(1) Synthesis of 8-benzyl 1,1-di-tert-butyl octane-1,1,8-tricarboxylate

60% Sodium hydride (59 mg, 1.48 mmol) was suspended in DMF (5.4 mL), to which di-tert-butyl malonate (0.30 mL, 1.35 mmol) was gradually added under ice cooling, and the mixture was stirred at 0° C. for 5 minutes and then for 20 minutes after the bath was removed. Under ice cooling, sodium iodide (61 mg, 0.40 mmol) and the compound (443 mg, 1.41 mmol) obtained in Production Example 3 were added and the mixture was stirred at room temperature for 15 hours. The reaction mixture was cooled in an ice water bath, added with water and extracted with diethyl ether. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (456 mg, 1.02 mmol).

$^1$H-NMR (400 MHz, CDCl$_3$) δ(ppm): 1.23-1.36 (m, 8H), 1.45 (s, 18H), 1.58-1.69 (m, 2H), 1.72-1.84 (m, 2H), 2.30-2.40 (m, 2H), 3.05-3.15 (m, 1H), 5.11 (s, 2H), 7.28-7.41 (m, 5H).

(2) Synthesis of 1,15-dibenzyl 8,8-di-tert-butyl pentadecane-1,8,8,15-tetracarboxylate According to the method in Example A-4-(1), the titled compound (380 mg, 0.56 mmol) was obtained from the compound (456 mg, 1.02 mmol) obtained in Example A-4-(1), the compound (478 mg, 1.53 mmol) obtained in Production Example 3, sodium iodide (46 mg, 0.31 mmol), 60% sodium hydride (49 mg, 1.22 mmol) and DMF (3.3 mL).

$^1$H-NMR (400 MHz, CDCl$_3$) δ(ppm): 1.03-1.17 (m, 4H), 1.23-1.36 (m, 12H), 1.43 (s, 18H), 1.56-1.68 (m, 4H), 1.70-1.80 (m, 4H), 2.29-2.38 (m, 4H), 5.11 (s, 4H), 7.27-7.41 (m, 10H).

(3) Synthesis of 10-(benzyloxy)-2-[8-(benzyloxy)-8-oxooctyl]-10-oxodecanoic acid According to the method in Example A-1-(3), the titled compound (234 mg, 0.45 mmol) was obtained from the compound (380 mg, 0.56 mmol) obtained in Example A-4-(2), methylene chloride (2 mL), TFA (1 mL) and xylene (2 mL).

$^1$H-NMR (400 MHz, CDCl$_3$) δ(ppm): 1.18-1.37 (m, 16H), 1.38-1.71 (m, 8H), 2.26-2.41 (m, 5H), 5.11 (s, 4H), 7.28-7.43 (m, 10H).

(4) Synthesis of dibenzyl 9-(hydroxymethyl)heptadecanedioate

According to the method in Example A-1-(4), the titled compound (188 mg, 0.37 mmol) was obtained from the compound (234 mg, 0.45 mmol) obtained in Example A-4-(3), 0.92M borane-THF complex (0.73 mL, 0.67 mmol) and THF (1.8 mL).

$^1$H-NMR (400 MHz, CDCl$_3$) δ(ppm): 1.12-1.51 (m, 22H), 1.56-1.72 (m, 4H), 2.29-2.41 (m, 4H), 3.47-3.58 (m, 2H), 5.11 (s, 4H), 7.28-7.44 (m, 10H).

(5) Synthesis of dibenzyl 9-{[[(1-methylpiperidine-4-carbonyl)oxy]methyl}heptadecanedioate According to the method in Example A-1-(5), the titled compound (217 mg, 0.34 mmol) was obtained from the compound (188 mg, 0.37 mmol) obtained in Example A-4-(4), 1-methyl-piperidine-4-carboxylic acid hydrochloride (132 mg, 0.74 mmol), EDC (155 mg, 0.81 mmol), DIPEA (0.126 mL, 0.74 mmol), DMAP (9.0 mg, 0.074 mmol) and methylene chloride (1.9 mL).

$^1$H-NMR (400 MHz, CDCl$_3$) δ(ppm): 1.16-1.38 (m, 21H), 1.53-1.69 (m, 4H), 1.70-1.84 (m, 2H), 1.85-2.04 (m, 4H), 2.19-2.40 (m, 5H), 2.26 (s, 3H), 2.74-2.86 (m, 2H), 3.92-4.01 (m, 2H), 5.11 (s, 4H), 7.28-7.41 (m, 10H).

(6) Synthesis of bis(3-pentyloctyl) 9-{[(1-methylpiperidine-4-carbonyl)oxy]methyl}heptadecanedioate The compound (217 mg, 0.34 mmol) obtained in Example A-4-(5) was dissolved in THF (4 mL) and methanol (2 mL), to which 10% palladium-carbon (19 mg, containing 50% water) was added at room temperature, and the mixture was stirred in a hydrogen atmosphere under normal pressure for 2 hours. The reaction system was replaced with nitrogen and the reaction solution was filtered and washed with methanol. The filtrate was concentrated under reduced pressure to obtain a crude product of 9-{[(1-methylpiperidine-4-carbonyl)oxy]methyl}heptadecanedioic acid (160 mg).

According to the method in Production Example 2, the titled compound (34 mg, 0.041 mmol) was obtained from the obtained crude product (40 mg), 3-pentyloctan-1-ol (CAS 1443519-63-8) (44 mg, 0.22 mmol), EDC (37 mg, 0.19 mmol), DMAP (2.1 mg, 0.018 mmol) and THF (1 mL).

$^1$H-NMR (400 MHz, CDCl$_3$) δ(ppm): 0.83-0.94 (m, 12H), 1.14-1.48 (m, 53H), 1.51-1.67 (m, 10H), 0.70-1.84 (m, 2H), 1.85-2.07 (m, 4H), 2.18-2.34 (m, 5H), 2.27 (s, 3H), 2.74-2.88 (m, 2H), 3.93-4.01 (m, 2H), 4.03-4.12 (m, 4H).

Synthesis of Cationic Lipid (5)

Example A-5

Di[(Z)-2-nonen-1-yl] 9-{[[(1-methylpiperidine-4-carbonyl)oxy]methyl}heptadecanedioate (Cationic Lipid 5)

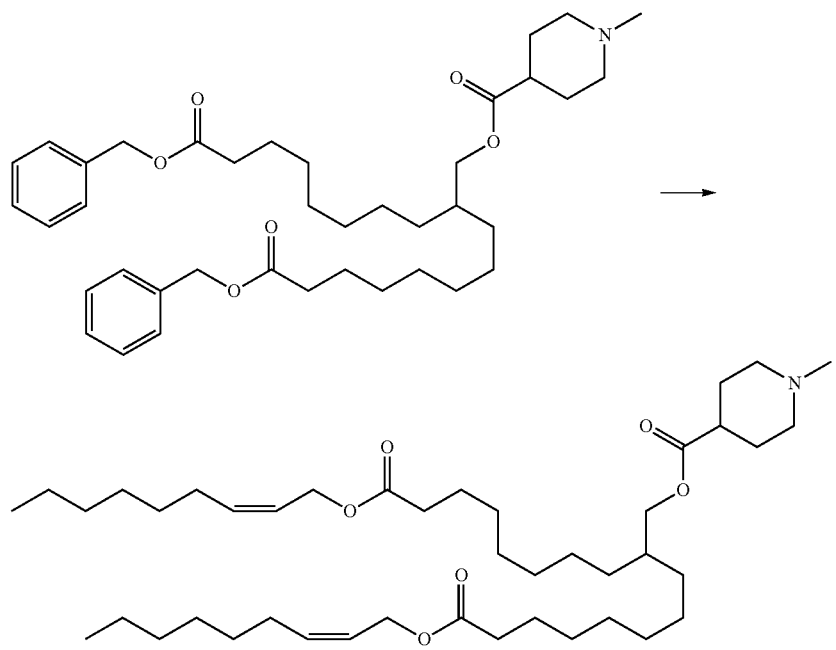

According to the method in Production Example 2, the titled compound (76 mg, 0.11 mmol) was obtained from the crude product (60 mg) of 9-{[(1-methylpiperidine-4-carbonyl)oxy]methyl}heptadecanedioic acid obtained in Example A-4-(6), cis-2-nonen-1-ol (0.066 mL, 0.40 mmol), EDC (56 mg, 0.29 mmol), DMAP (3.2 mg, 0.026 mmol) and THF (1.3 mL).

$^1$H-NMR (400 MHz, CDCl$_3$) δ(ppm): 0.81-0.96 (m, 6H), 1.15-1.44 (m, 35H), 1.52-1.68 (m, 6H), 1.70-1.84 (m, 2H), 1.85-2.05 (m, 4H), 2.05-2.15 (m, 4H), 2.21-2.35 (m, 5H), 2.27 (s, 3H), 2.74-2.88 (m, 2H), 3.93-4.01 (m, 2H), 4.57-4.67 (m, 4H), 5.47-5.58 (m, 2H), 5.59-5.70 (m, 2H).

Synthesis of Cationic Lipid (6)

Example A-6

(1R,5S,6r)-2-{9-[(2-Butyloctyl)oxy]-9-oxononyl}dodecyl 3-methyl-3-azabicyclo[3.1.0]hexane-6-carboxylate (Cationic Lipid 6)

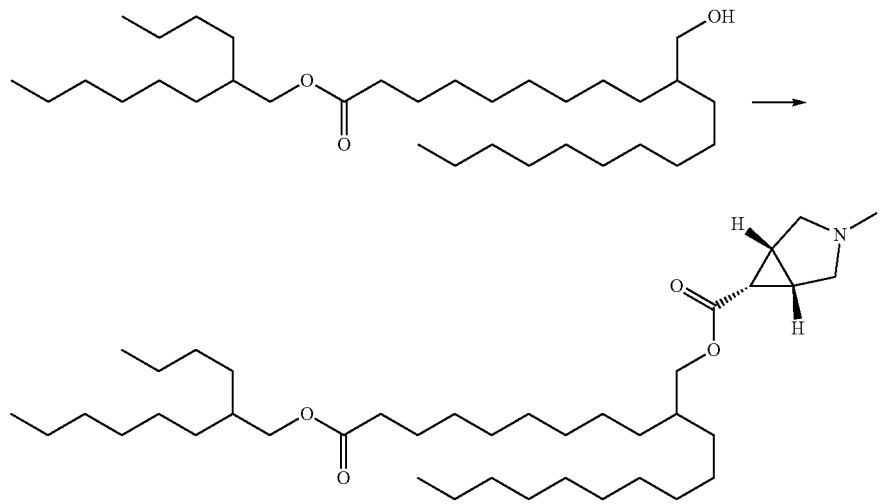

According to the method in Example A-1-(5), the titled compound (40 mg, 0.063 mmol) was obtained from the compound (40 mg, 0.078 mmol) obtained in Example A-1-(4), the compound (28 mg, 0.16 mmol) obtained in Production Example 10-(2), EDC (33 mg, 0.17 mmol), DIPEA (0.027 mL, 0.16 mmol), DMAP (1.9 mg, 0.016 mmol) and methylene chloride (1.0 mL).

$^1$H-NMR (400 MHz, CDCl$_3$) δ(ppm): 0.80-1.00 (m, 9H), 1.16-1.40 (m, 46H), 1.52-1.70 (m, 4H), 1.89-1.97 (m, 2H), 1.98-2.06 (m, 1H), 2.23-2.42 (m, 4H), 2.30 (s, 3H), 3.00-3.12 (m, 2H), 3.87-4.03 (m, 4H).

Synthesis of Cationic Lipid (7)

Example A-7

(1R,5S,6s)-2-{9-[(2-Butyloctyl)oxy]-9-oxononyl}dodecyl 3-methyl-3-azabicyclo[3.1.0]hexane-6-carboxylate (Cationic Lipid 7)

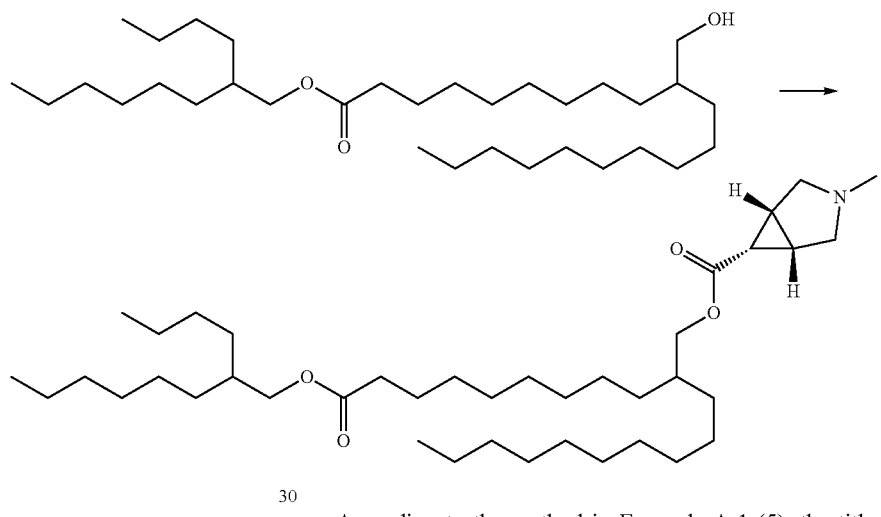

According to the method in Example A-1-(5), the titled compound (38 mg, 0.060 mmol) was obtained from the compound (40 mg, 0.078 mmol) obtained in Example A-1-(4), the compound (27.8 mg, 0.16 mmol) obtained in Production Example 11-(2), EDC (33 mg, 0.17 mmol), DIPEA (0.027 mL, 0.157 mmol), DMAP (1.9 mg, 0.016 mmol) and methylene chloride (1.0 mL).

$^1$H-NMR (400 MHz, CDCl$_3$) δ(ppm): 0.81-0.97 (m, 9H), 1.15-1.40 (m, 46H), 1.46-1.70 (m, 7H), 2.21 (s, 3H), 2.24-2.38 (m, 4H), 2.96-3.07 (m, 2H), 3.85-4.02 (m, 4H).

Synthesis of Cationic Lipid (8)

Example A-8

2-{9-[(2-Butyloctyl)oxy]-9-oxononyl}dodecyl 4-methylpiperazine-1-carboxylate (Cationic Lipid 8)

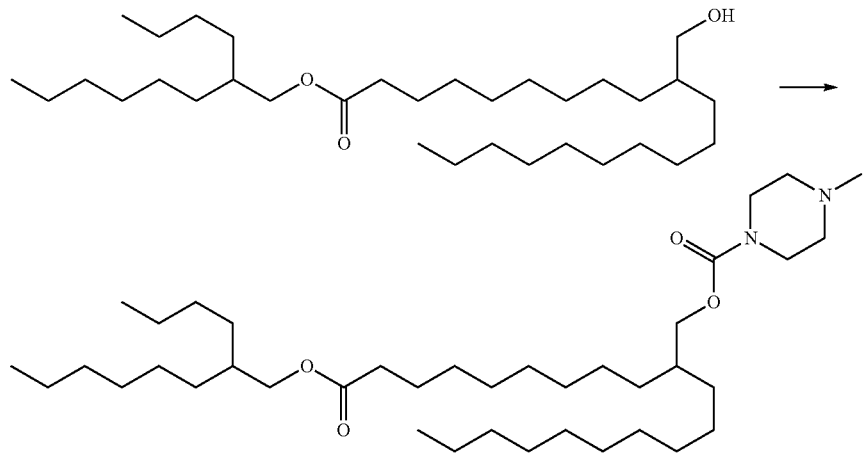

The compound (11 mg, 0.022 mmol) obtained in Example A-1-(4) and pyridine (0.0043 mL, 0.054 mmol) were dissolved in methylene chloride (0.8 mL), to which 4-nitrophenyl chloroformate (12 mg, 0.060 mmol) was added under ice cooling, and the mixture was stirred at the same temperature for 10 minutes and at room temperature for 1.5 hours. The reaction solution was added with 1-methylpiperazine (0.010 mL, 0.090 mmol) and stirred at room temperature for 3 hours. The reaction mixture was added with a saturated sodium hydrogen carbonate aqueous solution and extracted with ethyl acetate. The organic layer was washed with a saturated sodium chloride solution and dried over anhydrous magnesium sulphate. Following filtration, the solvent was removed by distillation under reduced pressure. The residue was purified by silica gel column chromatography (n-heptane/ethyl acetate) to obtain the titled compound (11 mg, 0.017 mmol).

$^1$H-NMR (400 MHz, CDCl$_3$) δ(ppm): 0.80-0.98 (m, 9H), 1.16-1.42 (m, 46H), 1.52-1.77 (m, 4H), 2.23-2.44 (m, 6H), 2.30 (s, 3H), 3.42-3.57 (m, 4H), 3.90-4.04 (m, 4H).

Synthesis of Cationic Lipid (9)

Example A-9

2-[9-(Hexyloxy)-9-oxononyl]dodecyl 1-methylpiperidine-4-carboxylate (Cationic Lipid 9)

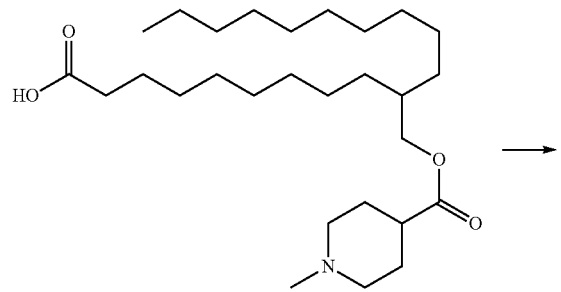

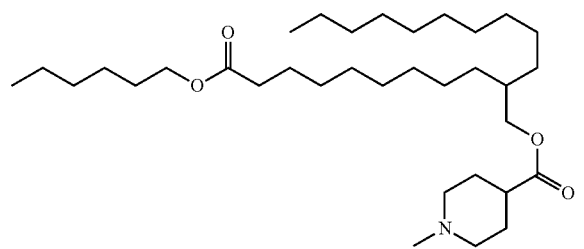

According to the method in Production Example 2, the titled compound (102 mg, 0.19 mmol) was obtained from the compound (100 mg, 0.21 mmol) obtained in Example A-2-(6), hexan-1-ol (32 μL, 0.26 mmol), EDC (49 mg, 0.26 mmol), DMAP (5.0 mg, 0.050 mmol) and methylene chloride (5.0 mL).

$^1$H-NMR (600 MHz, CDCl$_3$) δ(ppm): 0.85-0.92 (m, 6H), 1.19-1.39 (m, 37H), 1.57-1.66 (m, 5H), 1.73-1.84 (m, 2H), 1.87-1.94 (m, 2H), 1.96-2.07 (m, 2H), 2.22-2.32 (m, 6H), 2.73-2.87 (m, 2H), 3.98 (d, J=5.50 Hz, 2H), 4.06 (t, J=6.79 Hz, 2H).

Synthesis of Cationic Lipid (10)

Example A-10

2-[9-(Octyloxy)-9-oxononyl]dodecyl 1-methylpiperidine-4-carboxylate (Cationic Lipid 10)

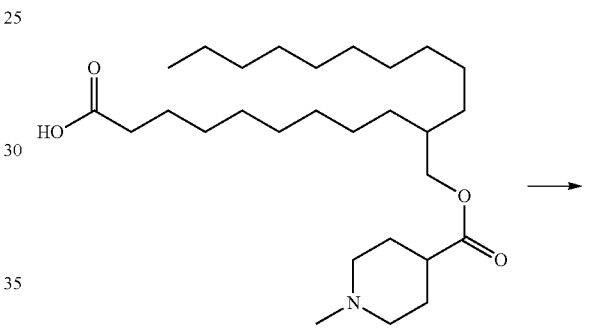

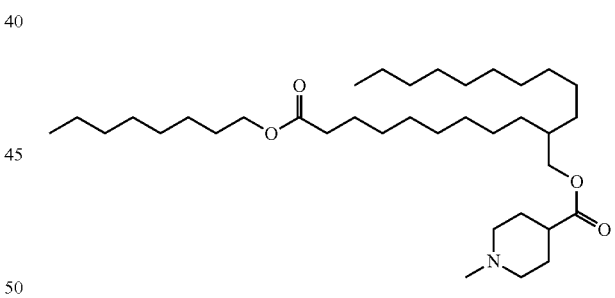

According to the method in Production Example 2, the titled compound (109 mg, 0.19 mmol) was obtained from the compound (200 mg, 0.42 mmol) obtained in Example A-2-(6), octan-1-ol (67 mg, 0.51 mmol), EDC (98 mg, 0.51 mmol), DMAP (10 mg, 0.09 mmol) and methylene chloride (10 mL).

$^1$H-NMR (600 MHz, CDCl$_3$) δ(ppm): 0.91 (t, J=6.97 Hz, 6H), 1.23-1.40 (m, 40H), 1.60-1.68 (m, 5H), 1.76-1.85 (m, 2H), 1.89-1.95 (m, 2H), 1.97-2.06 (m, 2H)2.25-2.33 (m, 6H), 2.78-2.86 (m, 2H), 4.00 (d, J=5.69 Hz, 2H), 4.08 (t, J=6.79 Hz, 2H).

Synthesis of Cationic Lipid (11)

Example A-11

2-[9-(Decyloxy)-9-oxononyl]dodecyl 1-methylpiperidine-4-carboxylate (Cationic Lipid 11)

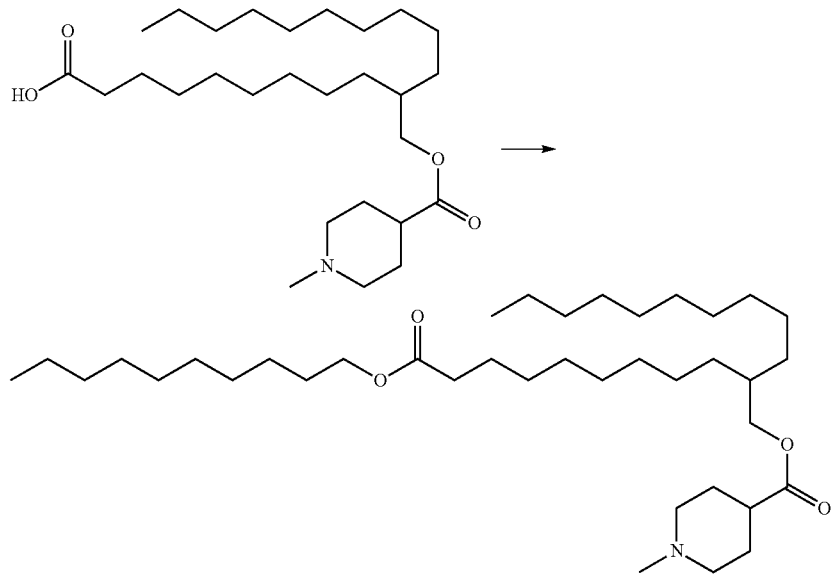

According to the method in Production Example 2, the titled compound (153 mg, 0.25 mmol) was obtained from the compound (200 mg, 0.42 mmol) obtained in Example A-2-(6), decan-1-ol (100 μL, 0.51 mmol), EDC (98 mg, 0.51 mmol), DMAP (10 mg, 0.09 mmol) and methylene chloride (10 mL).

$^1$H-NMR (600 MHz, CDCl$_3$) δ(ppm): 0.91 (t, J=7.06 Hz, 6H), 1.17-1.42 (m, 44H), 1.60-1.68 (m, 5H), 1.75-1.86 (m, 2H), 1.88-1.96 (m, 2H), 1.97-2.07 (m, 2H), 2.24-2.35 (m, 6H), 2.78-2.87 (m, 2H), 4.00 (d, J=5.50 Hz, 2H), 4.08 (t, J=6.79 Hz, 2H).

Synthesis of Cationic Lipid (12)

Example A-12

2-{9-Oxo-9-[(4-pentylnonyl)oxy]nonyl}dodecyl 1-methylpiperidine-4-carboxylate (Cationic Lipid 12)

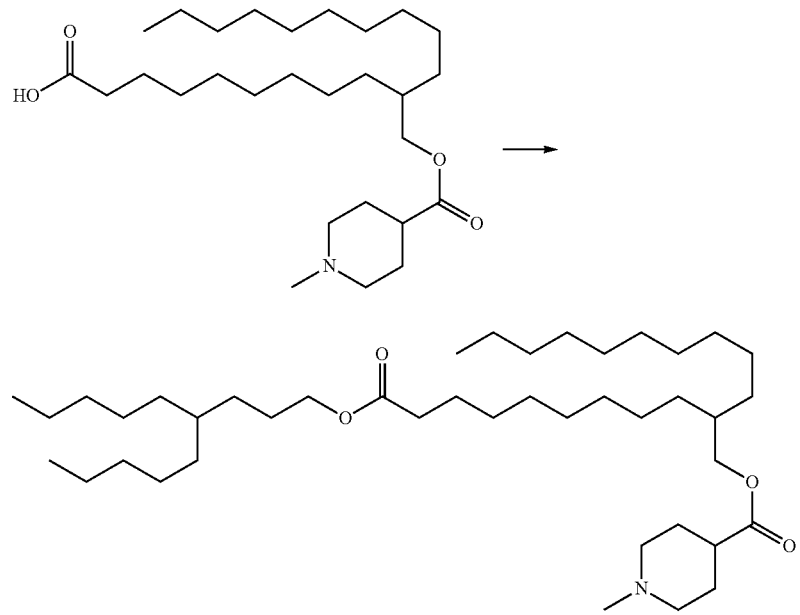

According to the method in Production Example 2, the titled compound (212 mg, 0.32 mmol) was obtained from the compound (200 mg, 0.42 mmol) obtained in Example A-2-(6), the compound (115 mg, 0.60 mmol) obtained in Production Example 7-(2), EDC (98 mg, 0.51 mmol), DMAP (10 mg, 0.09 mmol) and methylene chloride (10 mL).

$^1$H-NMR (600 MHz, CDCl$_3$) δ(ppm): 0.85-0.92 (m, 9H), 1.16-1.34 (m, 49H), 1.51-1.66 (m, 5H), 1.73-1.84 (m, 2H), 1.86-1.94 (m, 2H), 1.95-2.05 (m, 2H), 2.23-2.31 (m, 6H), 2.75-2.85 (m, 2H), 3.98 (d, J=5.50 Hz, 2H), 4.04 (t, J=6.79 Hz, 2H).

Synthesis of Cationic Lipid (13)

Example A-13

2-(4-Oxo-4-(tridecyloxy)butyl)dodecyl 1-methylpiperidine-4-carboxylate (Cationic Lipid 13)

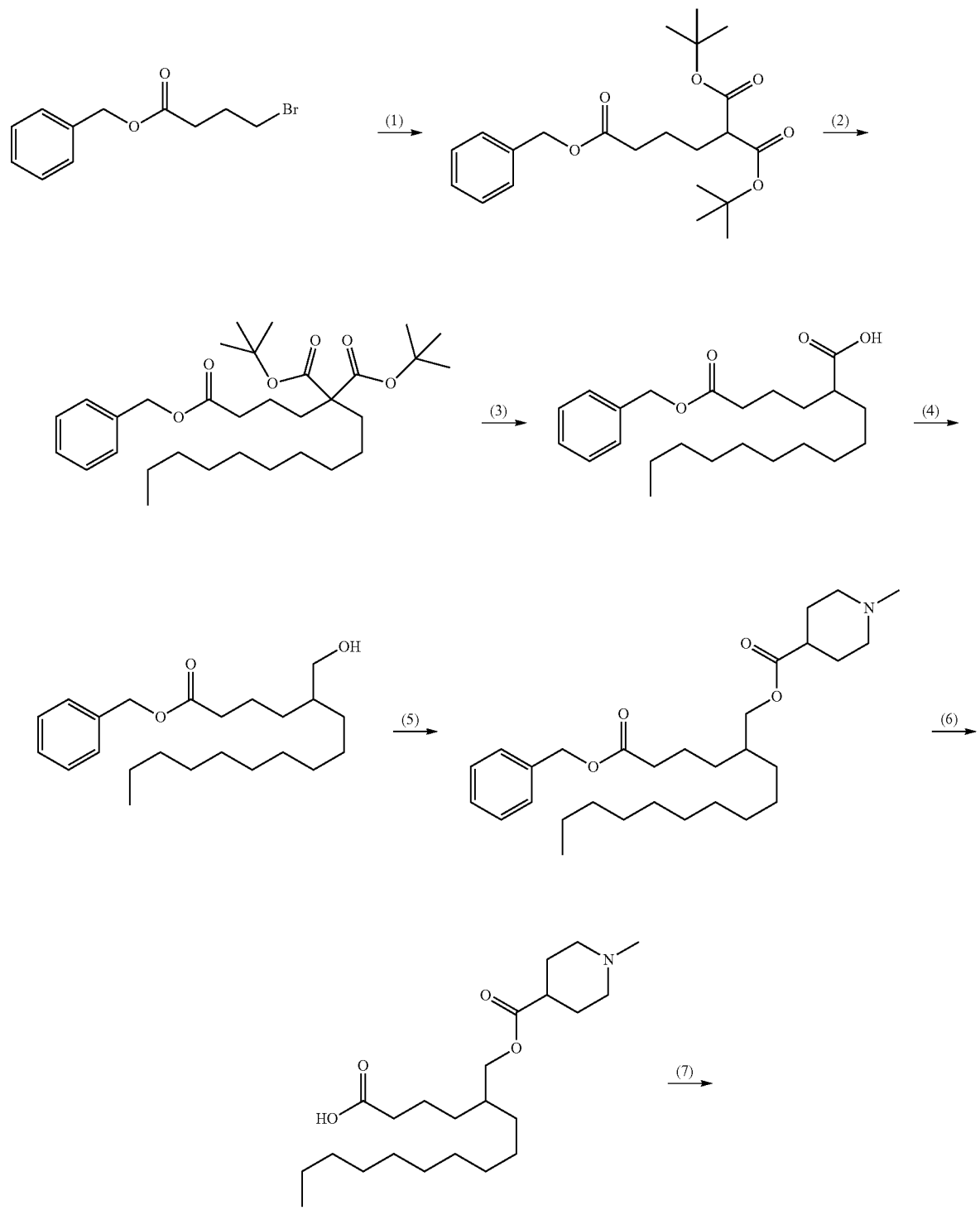

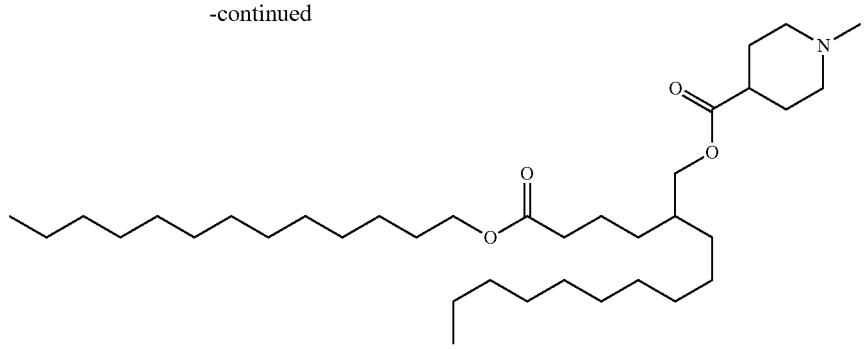

(1) Synthesis of 4-benzyl 1,1-di-tert-butyl butane-1,1,4-tricarboxylate

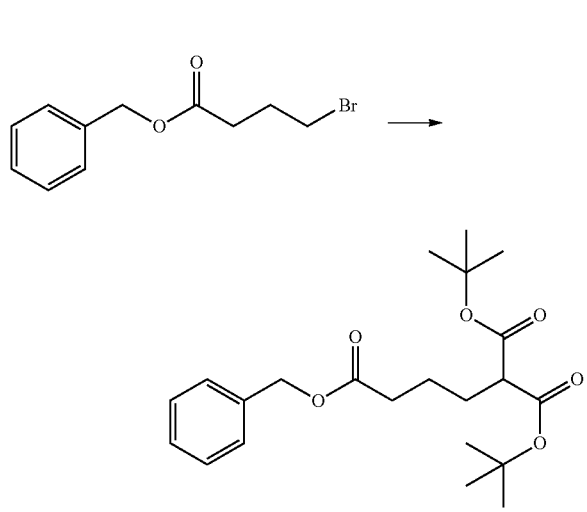

60% Sodium hydride (1.05 g, 26.2 mmol) was suspended in THF (50 mL), to which di-tert-butyl malonate (5.86 mL, 26.2 mmol) was added dropwise under ice cooling, and the mixture was stirred at room temperature for 20 minutes. Under ice cooling, sodium iodide (0.37 g, 2.49 mmol) was added, the compound (6.41 g, 24.9 mmol) obtained in Production Example 8 was then added dropwise and the mixture was stirred at room temperature for 18 hours. The reaction mixture was diluted with diethyl ether and washed with water, and the aqueous layer was then extracted with diethyl ether. The organic layers were combined, washed with a saturated sodium chloride solution and dried over anhydrous magnesium sulphate. Following filtration, the solvent was removed by distillation under reduced pressure to obtain the titled compound (9.88 g, 25.2 mmol).

$^1$H-NMR (600 MHz, CDCl$_3$) δ(ppm): 1.42-1.49 (m, 18H), 1.65-1.72 (m, 2H), 1.80-1.87 (m, 2H), 2.39 (t, J=7.52 Hz, 2H), 3.13 (t, J=7.52 Hz, 1H), 5.11 (s, 2H), 7.29-7.40 (m, 5H).

(2) Synthesis of 1-benzyl 4,4-di-tert-butyl tetradecane-1,4,4-tricarboxylate

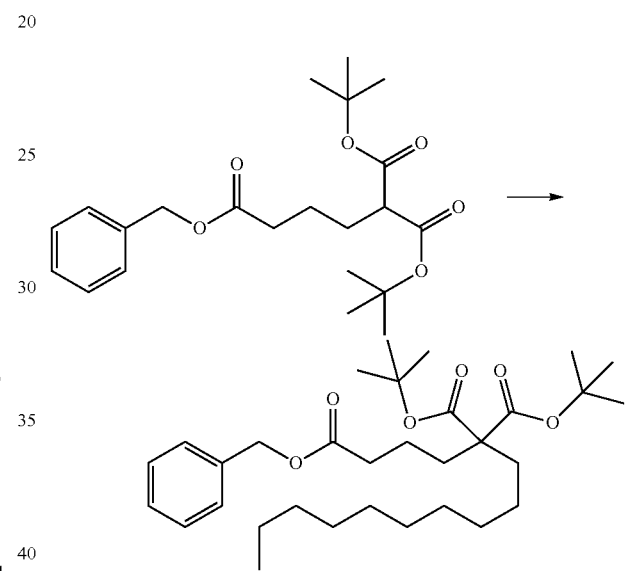

The compound (9.88 g, 25.2 mmol) obtained in Example A-13-(1) was dissolved in THF (100 mL), to which 60% sodium hydride (1.51 g, 37.8 mmol) was added underwater cooling, and the mixture was stirred at room temperature for 30 minutes. 1-Iododecane (10.7 mL, 50.4 mmol) was gradually added and the mixture was stirred at room temperature for 4 hours. The reaction mixture was added with a saturated ammonium chloride aqueous solution and extracted with n-pentane. The organic layer was washed with a saturated sodium chloride solution and dried over anhydrous magnesium sulphate. Following filtration, the solvent was removed by distillation under reduced pressure. The residue was purified by silica gel column chromatography (n-heptane/diethyl ether) to obtain the titled compound (4.31 g, 8.09 mmol).

$^1$H-NMR (600 MHz, CDCl$_3$) δ(ppm): 0.85-0.91 (m, 3H), 1.07-1.17 (m, 2H), 1.21-1.33 (m, 16H), 1.44 (s, 18H), 1.49-1.54 (m, 2H), 1.74-1.84 (m, 4H), 2.36 (t, J=7.34 Hz, 2H), 5.11 (s, 2H), 7.28-7.38 (m, 5H)

(3) Synthesis of 2-[4-(benzyloxy)-4-oxobutyl]dodecanoic acid

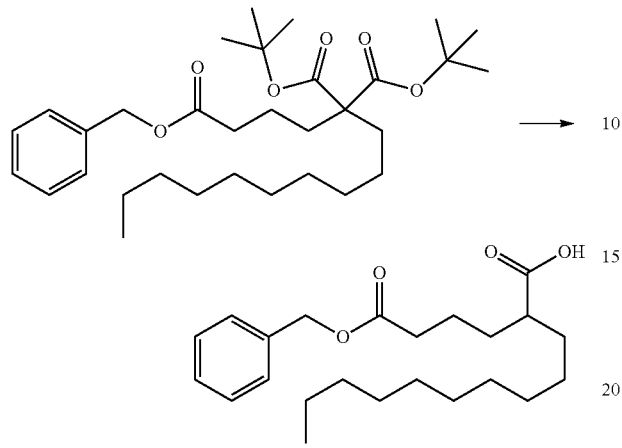

The compound (4.31 g, 8.09 mmol) obtained in Example A-13-(2) was dissolved in methylene chloride (20 mL), to which TFA (10 mL) was added dropwise under ice cooling, and the mixture was stirred at room temperature for 4 hours. The reaction mixture was concentrated under reduced pressure followed by addition of toluene and azeotropic distillation twice. The obtained crude product was dissolved in xylene (25 mL) and refluxed under heating for 8 hours. The reaction mixture was cooled to room temperature and concentrated under reduced pressure. The obtained residue was purified by column chromatography (cyclohexane/ethyl acetate) to obtain the titled compound (2.74 g, 7.28 mmol).

$^1$H-NMR (600 MHz, DMSO-d6) δ(ppm): 0.82-0.89 (m, 3H), 1.17-1.31 (m, 16H), 1.32-1.42 (m, 3H), 1.43-1.57 (m, 4H), 2.16-2.22 (m, 1H), 2.32-2.38 (m, 2H), 5.08 (s, 2H), 7.29-7.40 (m, 5H), 12.06 (br s, 1H).

(4) Synthesis of benzyl 5-(hydroxymethyl)pentadecanoate

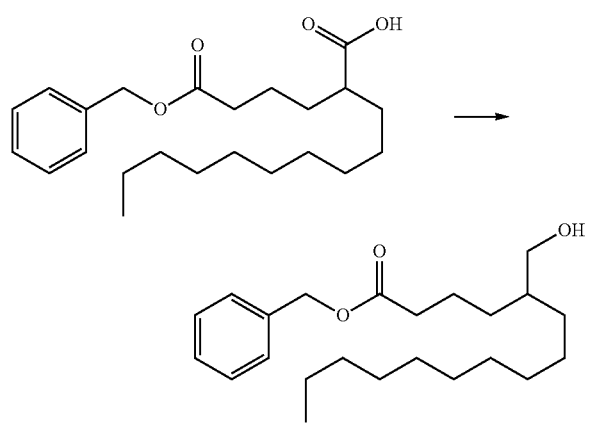

The compound (2.74 g, 7.28 mmol) obtained in Example A-13-(3) was dissolved in THF (30 mL), to which borane-THF complex (1 M, 16.9 mL, 16.9 mmol) was added dropwise at −78° C. The mixture was stirred at 0° C. for 8 hours and then at 15° C. for 22 hours. The mixture was added with a saturated sodium hydrogen carbonate aqueous solution and extracted with diethyl ether. The organic layer was washed with a saturated sodium chloride solution and dried over anhydrous magnesium sulphate. Following filtration, the solvent was removed by distillation under reduced pressure. The residue was purified by silica gel column chromatography (cyclohexane/ethyl acetate) to obtain the titled compound (2.30 g, 6.34 mmol).

$^1$H-NMR (600 MHz, DMSO-d6) δ(ppm): 0.85 (t, J=6.88 Hz, 3H), 1.08-1.37 (m, 18H), 1.49-1.58 (m, 2H), 2.27-2.36 (m, 2H), 3.21-3.29 (m, 2H), 4.28 (t, J=5.14 Hz, 1H), 5.01-5.12 (m, 2H), 7.30-7.40 (m, 5H)

(5) Synthesis of 2-(4-(benzyloxy)-4-oxobutyl)dodecyl 1-methylpiperidine-4-carboxylate

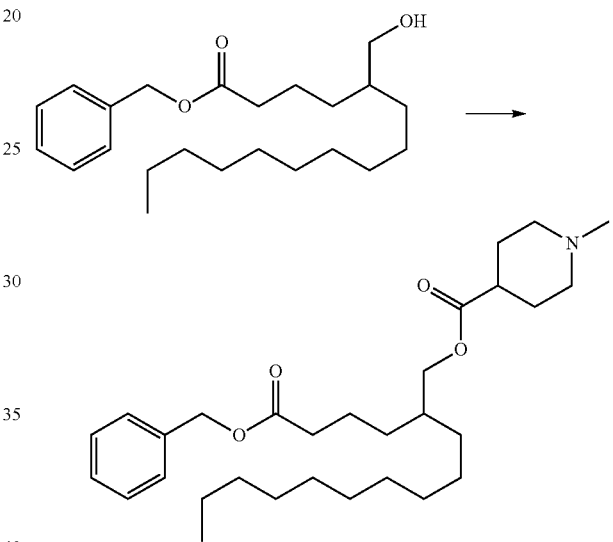

The compound (2.30 g, 6.34 mmol) obtained in Example A-13-(4), DIPEA (2.2 mL, 12.7 mmol), 1-methyl-piperidine-4-carboxylic acid hydrochloride (2.28 g, 12.7 mmol) and DMAP (0.16 g, 1.27 mmol) were dissolved in methylene chloride (30 mL), to which EDC (2.68 g, 13.9 mmol) was added under ice cooling, and the mixture was stirred at room temperature for 4 hours. The reaction mixture was concentrated under reduced pressure and dissolved in diethyl ether. The solution was serially washed with a saturated sodium hydrogen carbonate aqueous solution and water and dried over anhydrous magnesium sulphate. Following filtration, the solvent was removed by distillation under reduced pressure to obtain the titled compound (2.97 g, 6.09 mmol).

$^1$H-NMR (600 MHz, CDCl$_3$) δ(ppm): 0.88 (t, J=7.06 Hz, 3H), 1.17-1.38 (m, 21H), 1.60-1.70 (m, 3H), 1.77-1.87 (m, 2H), 1.89-1.99 (m, 2H), 2.23-2.38 (m, 6H), 2.74-2.91 (m, 2H), 3.94-4.02 (m, 2H), 5.09-5.13 (m, 2H), 7.30-7.41 (m, 5H).

(6) Synthesis of 5-{[(1-methylpiperidine-4-carbonyl)oxy]methyl}pentadecanoic acid

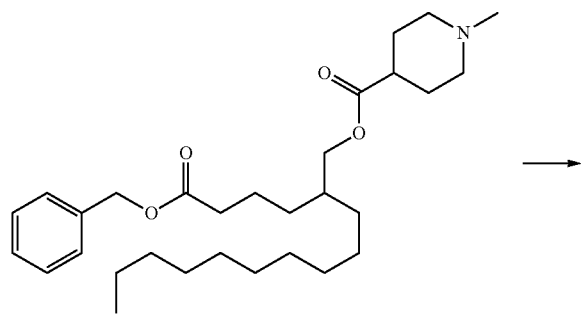

The compound (2.97 g, 6.09 mmol) obtained in Example A-13-(5) was dissolved in ethyl acetate (35 mL), to which 10% palladium-carbon (0.65 g, 0.61 mmol, containing 50% water) was added at room temperature, and the mixture was stirred in a hydrogen atmosphere under normal pressure for 3 hours. The reaction solution was filtered and washed with ethyl acetate. The filtrate was concentrated under reduced pressure to obtain the titled compound (2.31 g, 5.81 mmol).

$^1$H-NMR (600 MHz, DMSO-d6) δ(ppm): 0.85 (t, J=6.88 Hz, 3H), 1.21-1.32 (m, 20H), 1.44-1.66 (m, 5H), 1.75-1.83 (m, 2H), 1.95-1.98 (m, 1H), 1.99-2.06 (m, 1H), 2.13-2.23 (m, 5H), 2.23-2.30 (m, 1H), 2.64-2.77 (m, 2H), 3.88-3.97 (m, 2H).

(7) Synthesis of 2-(4-oxo-4-(tridecyloxy)butyl)dodecyl 1-methylpiperidine-4-carboxylate

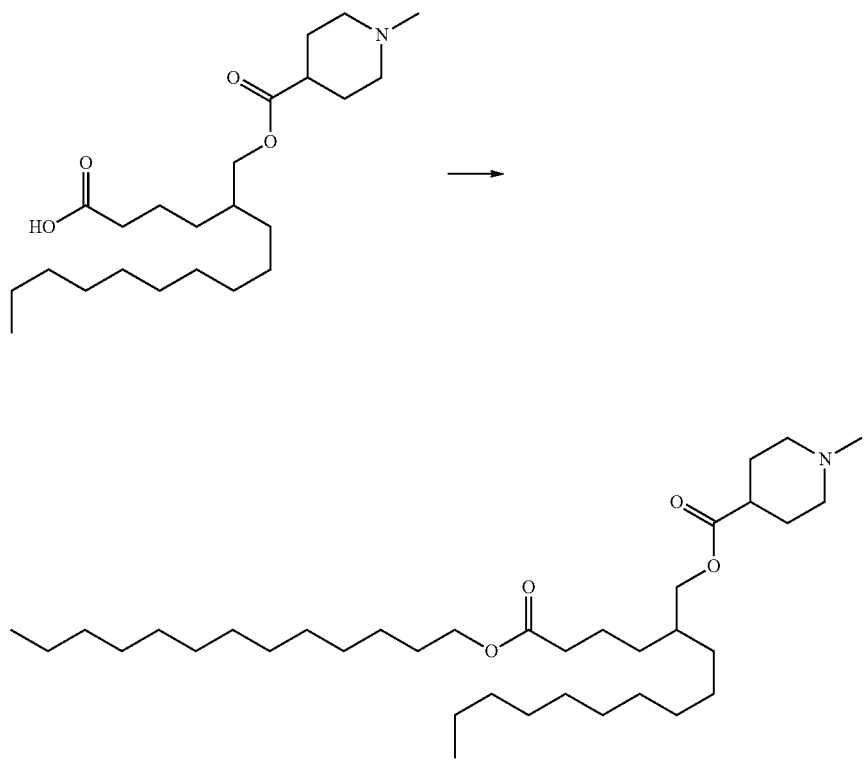

-continued

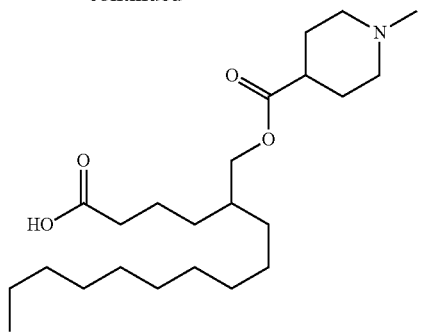

The compound (200 mg, 0.50 mmol) obtained in Example A-13-(6), tridecan-1-ol (121 mg, 0.60 mmol) and DMAP (12 mg, 0.10 mmol) were dissolved in methylene chloride (5 mL), to which EDC (116 mg, 0.60 mmol) was added at room temperature, and the mixture was stirred at room temperature for 4 hours. The reaction mixture was purified by silica gel column chromatography (methanol/ethyl acetate) to obtain the titled compound (170 mg, 0.29 mmol).

$^1$H-NMR (600 MHz, CDCl$_3$) δ(ppm): 0.88 (t, J=6.7 Hz, 6H), 1.26 (br s, 41H), 1.57-1.69 (m, 6H), 1.73-1.82 (m, 2H), 1.90 (br dd, J=13.5, 3.03 Hz, 2H), 1.94-2.04 (m, 2H), 2.22-2.34 (m, 6H), 2.67-2.90 (br d, J=9.8 Hz, 2H), 3.95-4.02 (m, 2H), 4.03-4.08 (t, J=6.8 Hz, 2H).

Synthesis of Cationic Lipid (14)

Example A-14

2-(4-Oxo-4-((8-pentyltridecyl)oxy)butyl)dodecyl 1-methylpiperidine-4-carboxylate (Cationic Lipid 14)

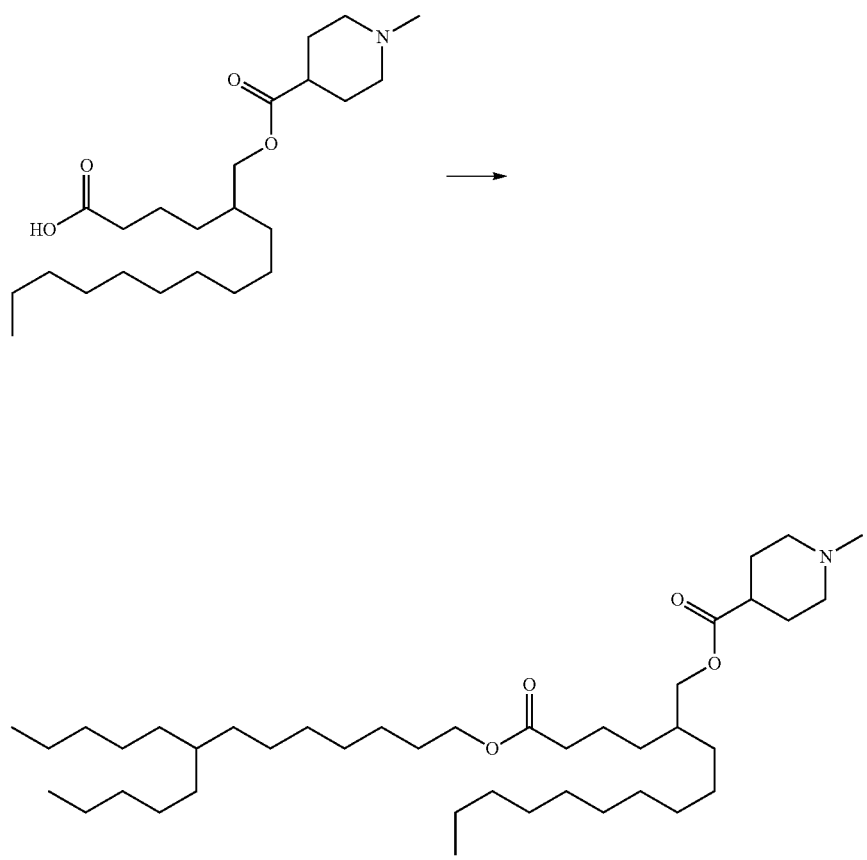

According to the method in Example A-13-(7), the titled compound (133 mg, 0.21 mmol) was obtained from the compound (120 mg, 0.30 mmol) obtained in Example A-13-(6), the compound (90 mg, 0.33 mmol) obtained in Production Example 4-(4), EDC (64 mg, 0.33 mmol), DMAP (4.0 mg, 0.033 mmol) and methylene chloride (1.5 mL).

$^1$H-NMR (600 MHz, CD$_3$OD) δ(ppm): 0.87-0.97 (m, 9H), 1.18-1.45 (m, 47H), 1.60-1.73 (m, 5H), 1.73-1.83 (m, 2H), 1.88-1.99 (m, 2H), 2.06-2.19 (m, 2H), 2.23-2.43 (m, 6H), 2.77-2.89 (m, 2H), 3.99-4.15 (m, 4H).

Synthesis of Cationic Lipid (15)

Example A-15

2-{4-[(4-Nonyltridecyl)oxy]-4-oxobutyl}dodecyl 1-methylpiperidine-4-carboxylate (Cationic Lipid 15)

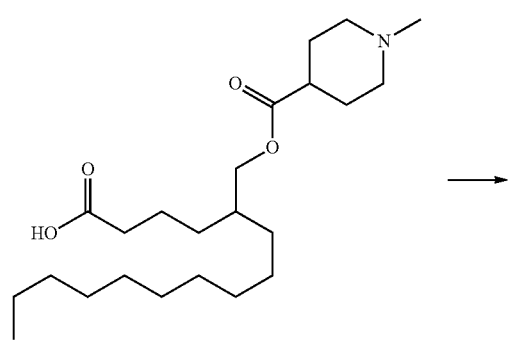

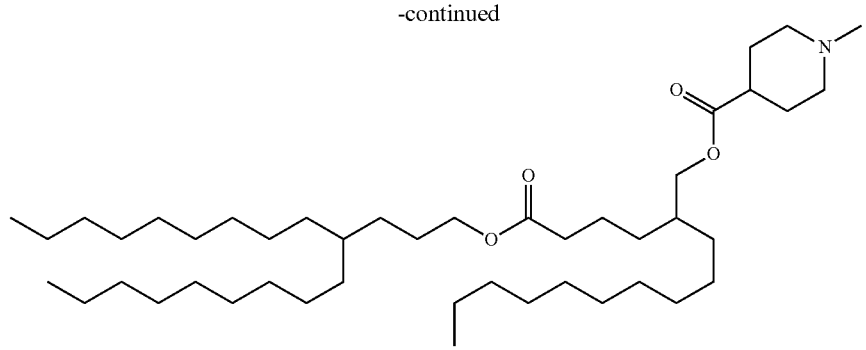

According to the method in Example A-13-(7), the titled compound (106 mg, 0.15 mmol) was obtained from the compound (110 mg, 0.28 mmol) obtained in Example A-13-(6), the compound (99 mg, 0.30 mmol) obtained in Production Example 5-(4), EDC (58 mg, 0.30 mmol), DMAP (4.0 mg, 0.033 mmol) and methylene chloride (1.3 mL).

$^1$H-NMR (600 MHz, CD$_3$OD) δ(ppm): 0.85-0.99 (m, 9H), 1.15-1.44 (m, 55H), 1.56-1.84 (m, 7H), 1.94 (m, J=13.2 Hz, 2H), 2.06-2.19 (m, 2H), 2.23-2.44 (m, 6H), 2.76-2.90 (m, 2H), 3.96-4.14 (m, 4H).

Synthesis of Cationic Lipid (16)

Example A-16

Dioctyl 9-{([(1-methylpiperidine-4-carbonyl)oxy]methyl}heptadecanedioate (Cationic Lipid 16)

(1) Synthesis of 9-{[(1-methylpiperidine-4-carbonyl)oxy]methyl}heptadecanedioic acid

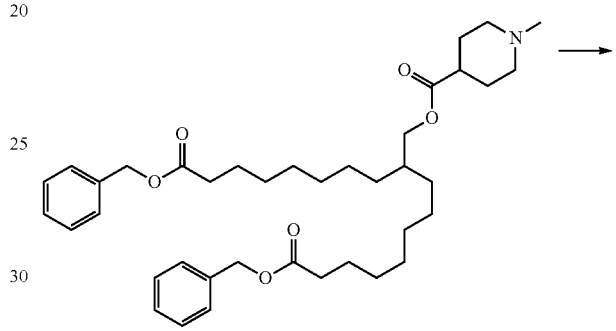

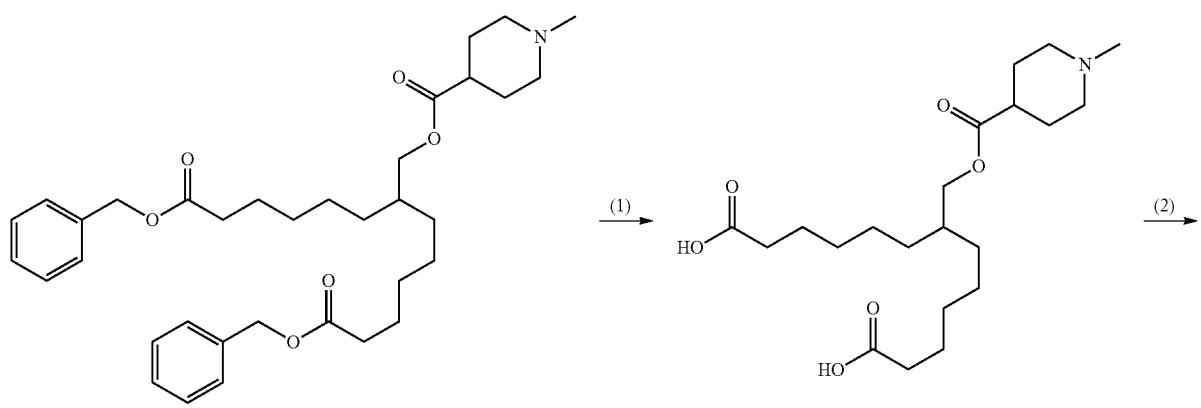

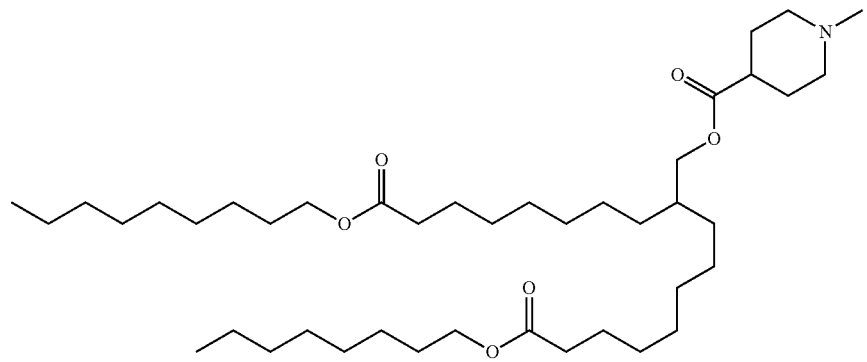

-continued

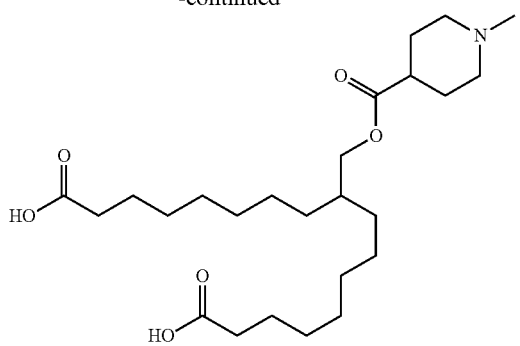

The compound (0.80 g, 1.25 mmol) obtained in Example A-4-(5) was dissolved in ethanol (5 mL), to which 10% palladium-carbon (0.13 g, 0.13 mmol, containing 50% water) was added at room temperature, and the mixture was stirred in a hydrogen atmosphere under normal pressure for 18 hours. The reaction solution was filtered through Celite and washed with ethanol. The filtrate was concentrated under reduced pressure to obtain the titled compound (0.58 g, 1.26 mmol).

$^1$H-NMR (600 MHz, DMSO-d6) δ(ppm): 1.17-1.30 (m, 20H), 1.43-1.52 (m, 4H), 1.52-1.62 (m, 3H), 1.77-1.82 (m, 2H), 1.92-2.03 (m, 2H), 2.12-2.22 (m, 7H), 2.23-2.33 (m, 1H), 2.66-2.75 (m, 2H), 3.93 (d, J=5.50 Hz, 2H).

(2) Synthesis of dioctyl 9-{[(1-methylpiperidine-4-carbonyl)oxy]methyl}heptadecanedioate

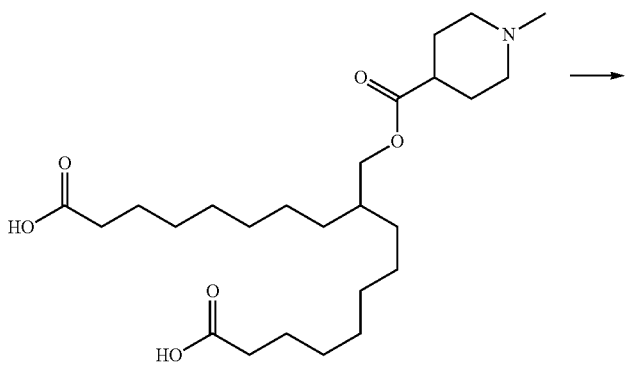

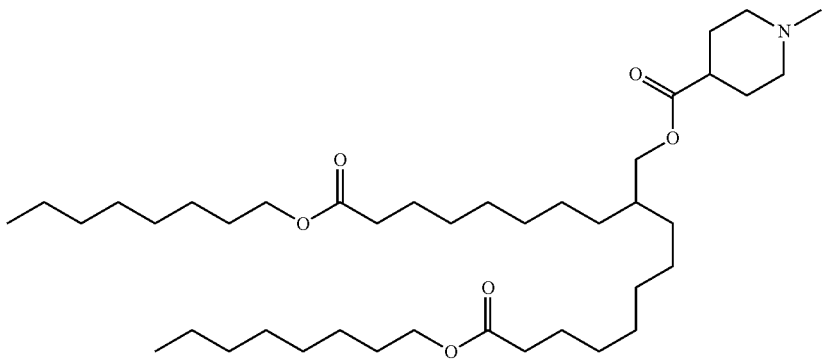

The compound (100 mg, 0.22 mmol) obtained in Example A-16-(1), octan-1-ol (83 µL, 0.53 mmol) and DMAP (11 mg, 0.09 mmol) were dissolved in methylene chloride (5 mL), to which EDC (101 mg, 0.53 mmol) was added at room temperature, and the mixture was stirred at room temperature for 18 hours. The reaction mixture was concentrated under reduced pressure and then purified by silica gel column chromatography (methanol/ethyl acetate) to obtain the titled compound (101 mg, 0.15 mmol).

$^1$H-NMR (600 MHz, CDCl$_3$) δ(ppm): 0.83-0.92 (m, 6H), 1.21-1.39 (m, 40H), 1.55-1.66 (m, 9H), 1.72-1.83 (m, 2H), 1.85-1.95 (m, 2H), 1.95-2.06 (m, 2H), 2.22-2.33 (m, 8H), 2.75-2.87 (m, 2H), 3.97 (d, J=5.69 Hz, 2H), 4.05 (t, J=6.69 Hz, 4H).

Synthesis of Cationic Lipid (17)

Example A-17

Bis(4-pentylnonyl) 9-{([(1-methylpiperidine-4-carbonyl)oxy]methyl}heptadecanedioate (Cationic Lipid 17)

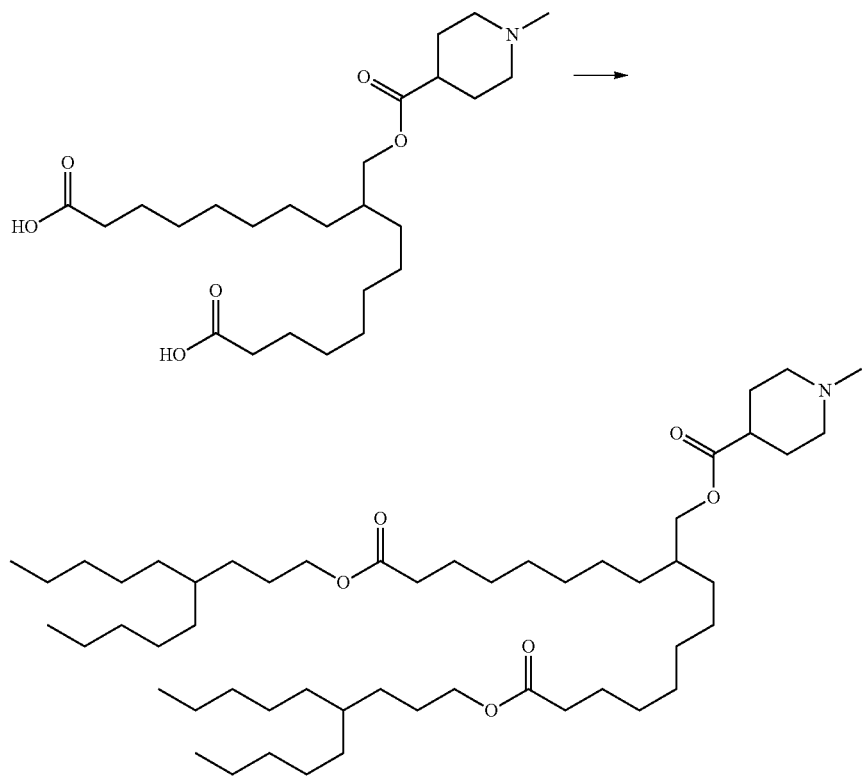

According to the method in Example A-16-(2), the titled compound (0.23 g, 0.27 mmol) was obtained from the compound (0.20 g, 0.44 mmol) obtained in Example A-16-(1), the compound (0.23 g, 1.05 mmol) obtained in Production Example 7-(2), EDC (0.20 g, 1.05 mmol), DMAP (11 mg, 0.09 mmol) and methylene chloride (5 mL).

$^1$H-NMR (600 MHz, CDCl$_3$) δ(ppm): 0.88 (t, J=7.24 Hz, 12H), 1.17-1.35 (m, 58H), 1.58-1.65 (m, 9H), 1.73-1.83 (m, 2H), 1.87-1.93 (m, 2H), 1.95-2.04 (m, 2H), 2.23-2.32 (m, 8H), 2.75-2.86 (m, 2H), 3.97 (d, J=5.50 Hz, 2H), 4.04 (t, J=6.79 Hz, 4H).

Synthesis of Cationic Lipid (18)
Example A-18
Ditridecyl 5-{[(1-methylpiperidine-4-carbonyl)oxy]methyl}nonanedioate (Cationic Lipid 18)
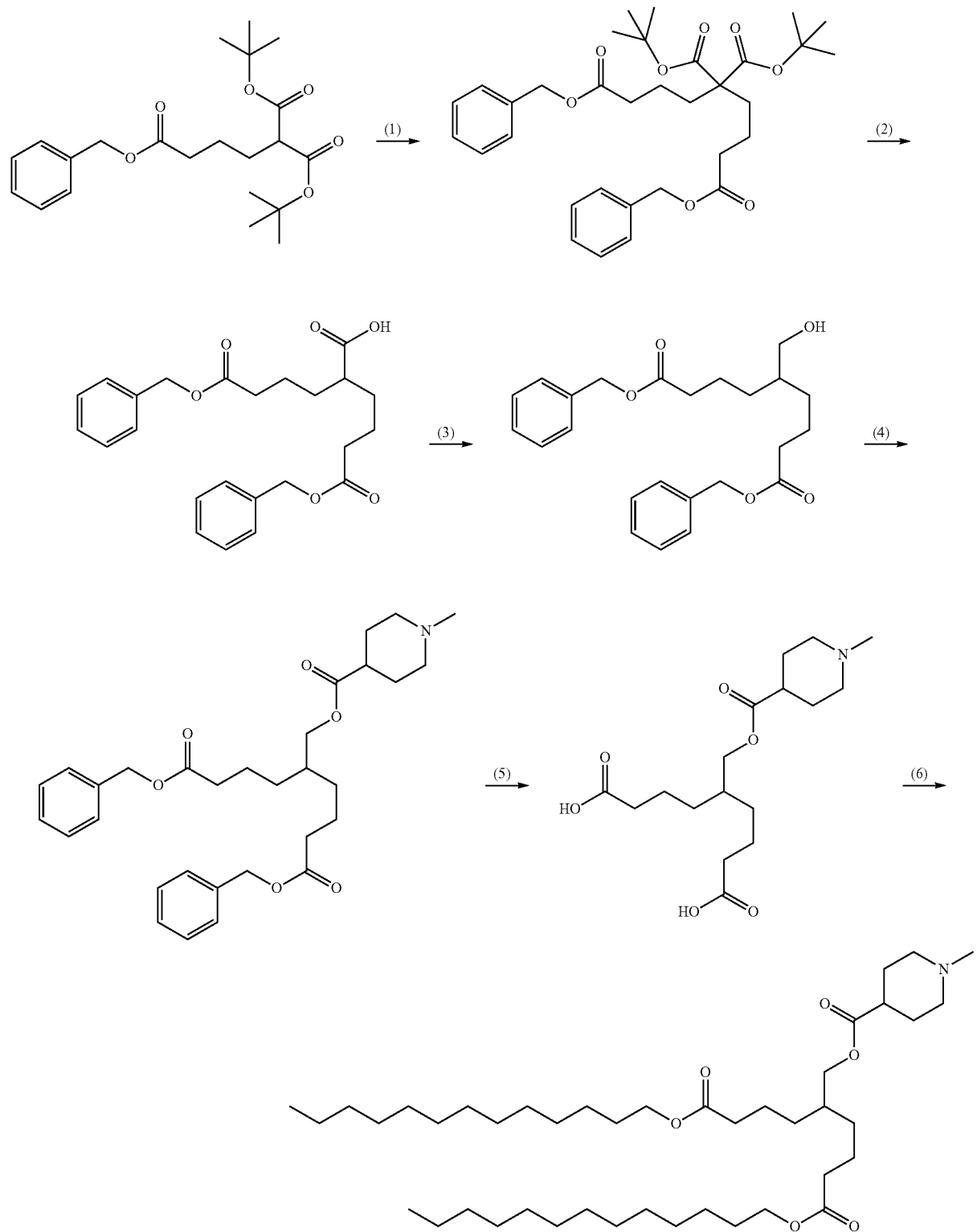

(1) Synthesis of 1,7-dibenzyl 4,4-di-tert-butyl heptane-1,4,4,7-tetracarboxylate

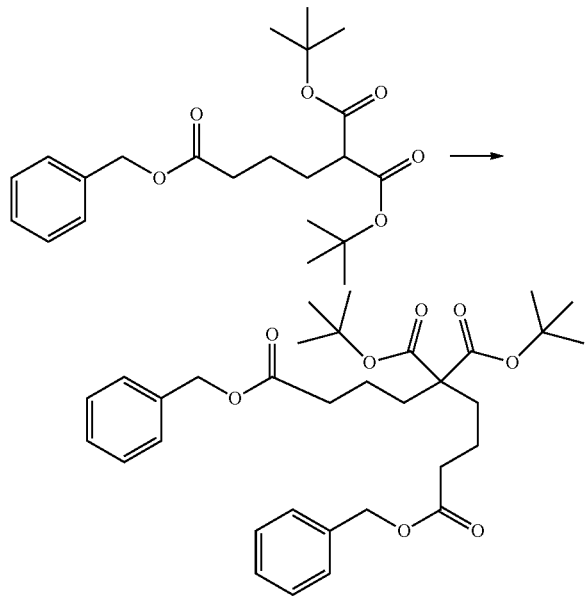

The compound (3.84 g, 9.78 mmol) obtained in Example A-13-(1) was dissolved in THF (30 mL), to which 60% sodium hydride (0.43 g, 10.8 mmol) was added under water cooling, and the mixture was stirred at room temperature for 30 minutes. A solution of benzyl 4-bromobutanoate (3.02 g, 11.7 mmol) in THF (10 mL) was added and refluxed under heating for 18 hours. The reaction solution was cooled to room temperature and diluted with diethyl ether. The organic layer was washed sequentially with water and a saturated sodium chloride solution and dried over anhydrous magnesium sulphate. Following filtration, the solvent was removed by distillation under reduced pressure. The residue was purified by silica gel column chromatography (ethyl acetate/cyclohexane) to obtain the titled compound (1.88 g, 3.31 mmol).

$^1$H-NMR (600 MHz, CDCl$_3$) δ(ppm): 1.43 (s, 18H), 1.47-1.54 (m, 4H), 1.78-1.85 (m, 4H), 2.36 (t, J=7.34 Hz, 4H), 5.10 (s, 4H), 7.27-7.40 (m, 10H).

(2) Synthesis of 6-(benzyloxy)-2-[4-(benzyloxy)-4-oxobutyl]-6-hexanoic acid

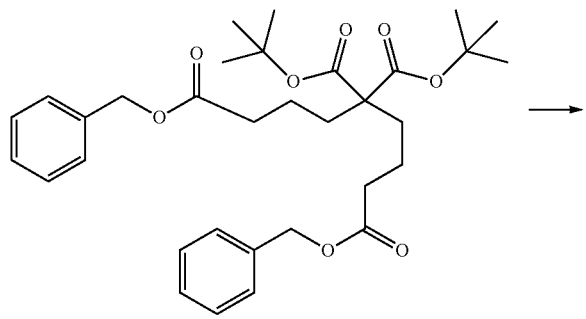

-continued

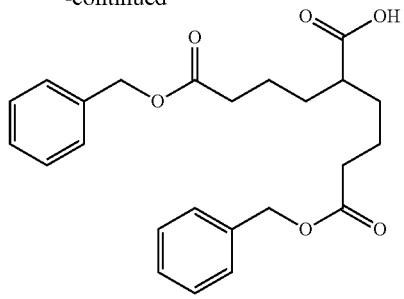

According to the method in Example A-13-(3), the titled compound (1.01 g, 2.45 mmol) was obtained from the compound (1.88 g, 3.31 mmol) obtained in Example A-18-(1), TFA (4 mL), methylene chloride (8 mL) and xylene (10 mL).

$^1$H-NMR (600 MHz, DMSO-d6) δ(ppm): 1.31-1.58 (m, 8H), 2.19-2.25 (m, 1H), 2.33-2.37 (m, 4H), 5.05-5.11 (m, 4H), 7.27-7.40 (m, 10H), 12.14 (br s, 1H).

(3) Synthesis of dibenzyl 5-(hydroxymethyl)nonanedioate

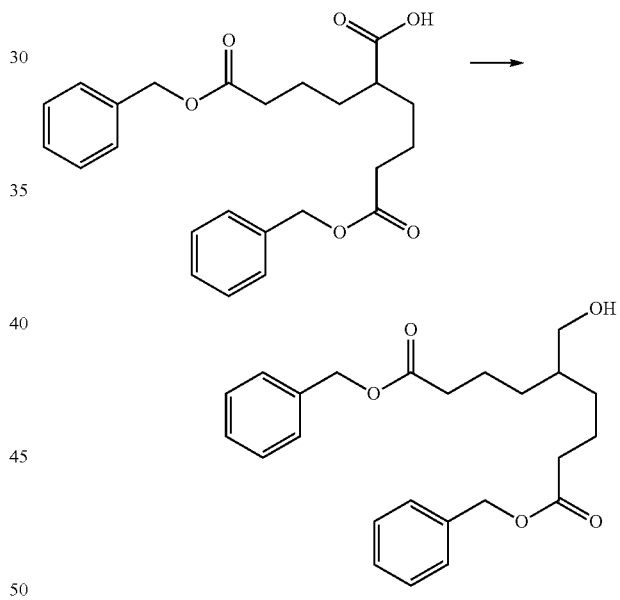

The compound (1.01 g, 2.45 mmol) obtained in Example A-18-(2) was dissolved in THF (10 mL), to which borane-THF complex (1 M, 4.9 mL, 4.9 mmol) was added dropwise at −78° C. The mixture was stirred at 0° C. for 16 hours, added with a saturated ammonium chloride aqueous solution and extracted with diethyl ether. The organic layer was washed with a saturated sodium chloride solution and dried over anhydrous magnesium sulphate. Following filtration, the solvent was removed by distillation under reduced pressure. The residue was purified by silica gel column chromatography (cyclohexane/ethyl acetate) to obtain the titled compound (0.59 g, 1.47 mmol).

$^1$H-NMR (600 MHz, DMSO-d6) δ(ppm): 1.09-1.37 (m, 6H), 1.48-1.56 (m, 4H), 2.32 (t, J=7.34 Hz, 4H), 3.26 (t, J=5.23 Hz, 2H), 4.32 (t, J=5.14 Hz, 1H), 5.08 (s, 4H), 7.28-7.41 (m, 10H).

(4) Synthesis of dibenzyl 5-{([(1-methylpiperidine-4-carbonyl)oxy]methyl}nonanedioate (5) Synthesis of 5-[{(1-methylpiperidine-4-carbonyl)oxy}methyl]nonanedioic acid

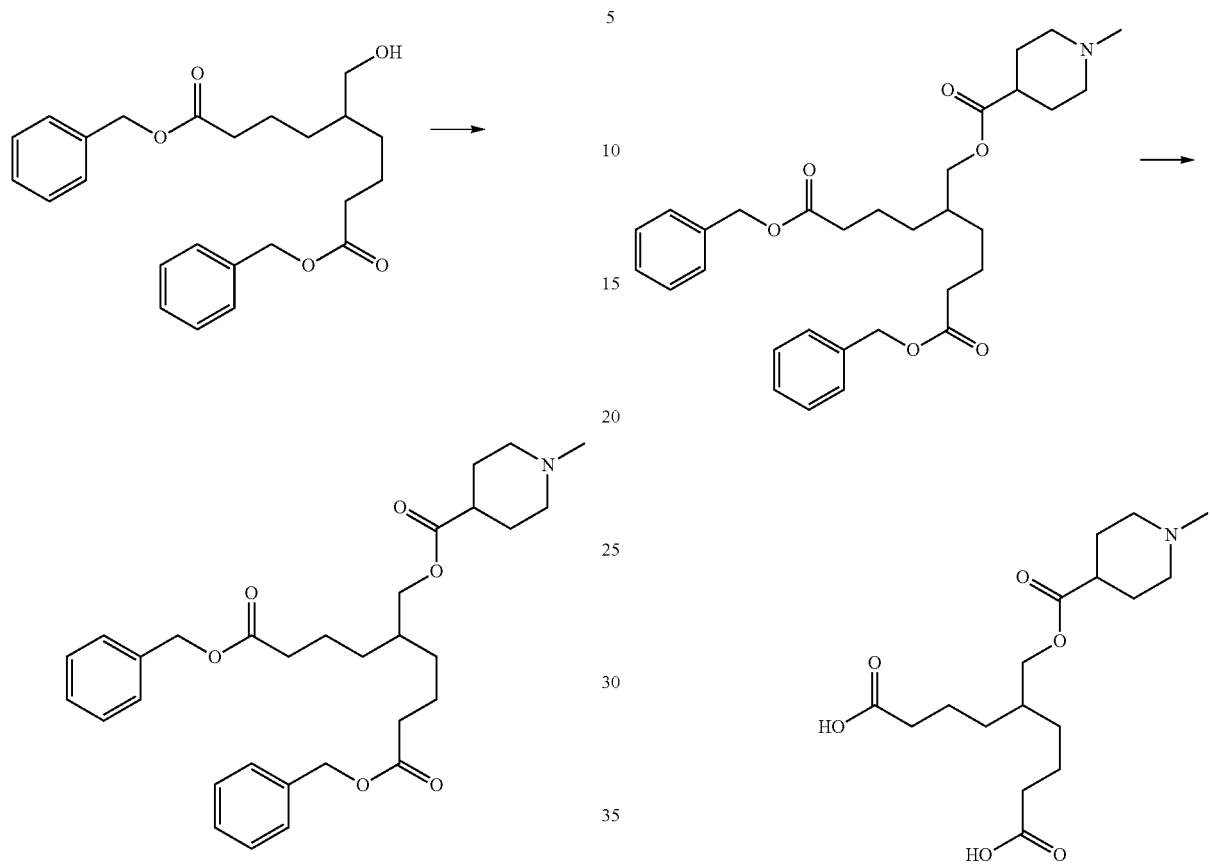

According to the method in Example A-13-(5), the titled compound (0.62 g, 1.19 mmol) was obtained from the compound (0.58 g, 1.47 mmol) obtained in Example A-18-(3), DIPEA (0.51 mL, 2.95 mmol), 1-methyl-piperidine-4-carboxylic acid hydrochloride (0.52 g, 2.95 mmol), DMAP (36 mg, 0.30 mmol), EDC (0.62 g, 3.24 mmol) and methylene chloride (7 mL).

$^1$H-NMR (600 MHz, CDCl$_3$) δ(ppm): 1.27-1.38 (m, 4H), 1.59-1.69 (m, 5H), 1.70-1.81 (m, 2H), 1.85-1.92 (m, 2H), 1.92-2.02 (m, 2H), 2.26 (s, 4H), 2.33 (t, J=7.34 Hz, 4H), 2.74-2.83 (m, 2H), 3.97 (d, J=5.69 Hz, 2H), 5.11 (s, 4H), 7.28-7.39 (m, 10H).

According to the method in Example A-16-(1), the titled compound (0.41 g, 1.19 mmol) was obtained from the compound (0.62 g, 1.19 mmol) obtained in Example A-18-(4), 10% palladium-carbon (62 mg, 0.06 mmol, containing 50% water) and ethanol (2 mL).

$^1$H-NMR (600 MHz, DMSO-d6) δ(ppm): 1.20-1.31 (m, 4H), 1.44-1.66 (m, 7H), 1.72-1.81 (m, 4H), 1.88-1.97 (m, 2H), 2.13 (s, 3H), 2.16-2.22 (m, 4H), 2.22-2.30 (m, 1H), 2.64-2.71 (m, 2H), 3.93 (d, J=5.32 Hz, 2H).

(6) Synthesis of ditridecyl 5-{[(1-methylpiperidine-4-carbonyl)oxy]methyl}nonanedioate

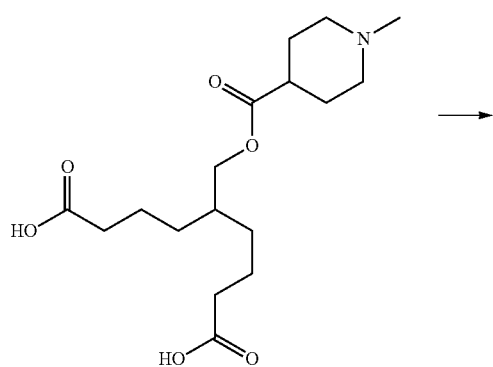

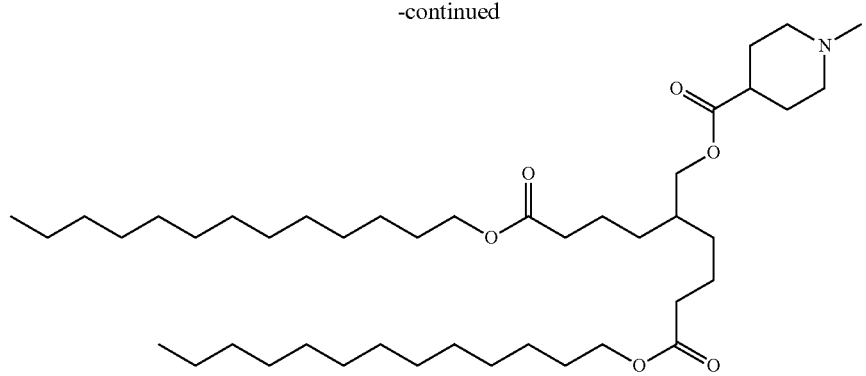

According to the method in Example A-13-(7), the titled compound (107 mg, 0.15 mmol) was obtained from the compound (135 mg, 0.39 mmol) obtained in Example A-18-(5), tridecan-1-ol (189 mg, 0.94 mmol), DMAP (9 mg, 0.08 mmol), EDC (166 mg, 0.87 mmol) and methylene chloride (5 mL).

$^1$H-NMR (600 MHz, CDCl$_3$) δ(ppm): 0.88 (t, J=7.06 Hz, 6H), 1.20-1.41 (m, 45H), 1.58-1.71 (m, 9H), 1.71-1.82 (m, 2H), 1.86-1.94 (m, 2H), 1.95-2.04 (m, 2H), 2.23-2.30 (m, 8H), 2.77-2.83 (m, 2H), 4.00 (d, J=5.5 Hz, 2H), 4.05 (t, J=6.88 Hz, 4H).

Synthesis of Cationic Lipid (19)

Example A-19

Bis(8-pentyltridecyl) 5-{[(1-methylpiperidine-4-carbonyl)oxy]methyl}nonanedioate (Cationic Lipid 19)

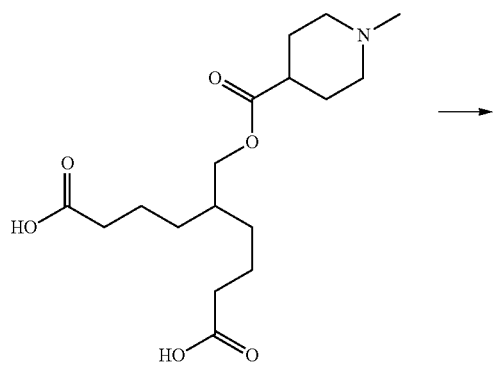

→

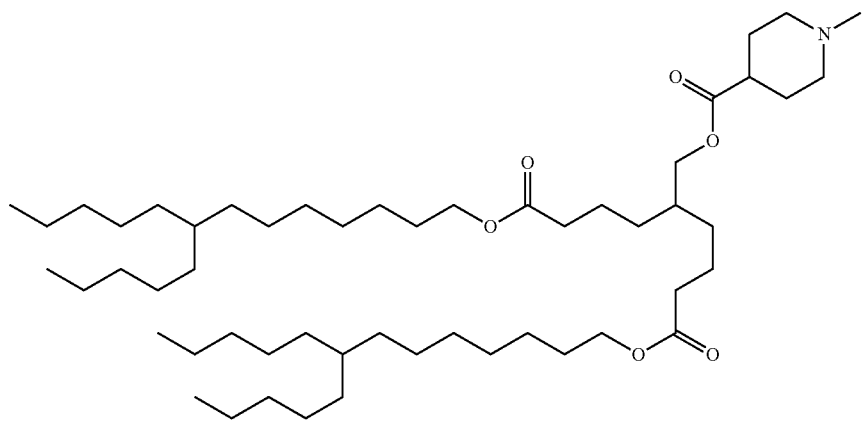

According to the method in Example A-13-(7), the titled compound (79 mg, 0.09 mmol) was obtained from the compound (80 mg, 0.23 mmol) obtained in Example A-18-(5), the compound (151 mg, 0.56 mmol) obtained in Production Example 4-(4), DMAP (6 mg, 0.05 mmol), EDC (98 mg, 0.51 mmol) and methylene chloride (5 mL).

$^1$H-NMR (600 MHz, CDCl$_3$) δ(ppm): 0.88 (t, J=7.24 Hz, 12H), 1.15-1.40 (m, 60H), 1.59-1.71 (m, 10H), 1.72-1.82 (m, 2H), 1.86-1.94 (m, 2H), 1.94-2.04 (m, 2H), 2.23-2.32 (m, 8H), 2.77-2.85 (m, 2H), 4.00 (d, J=5.5 Hz, 2H), 4.05 (t, J=6.88 Hz, 4H).

Synthesis of Cationic Lipid (20)

Example A-20

Bis(4-nonyltridecyl) 5-{([(1-methylpiperidine-4-carbonyl)oxy]methyl}nonanedioate (Cationic Lipid 20)

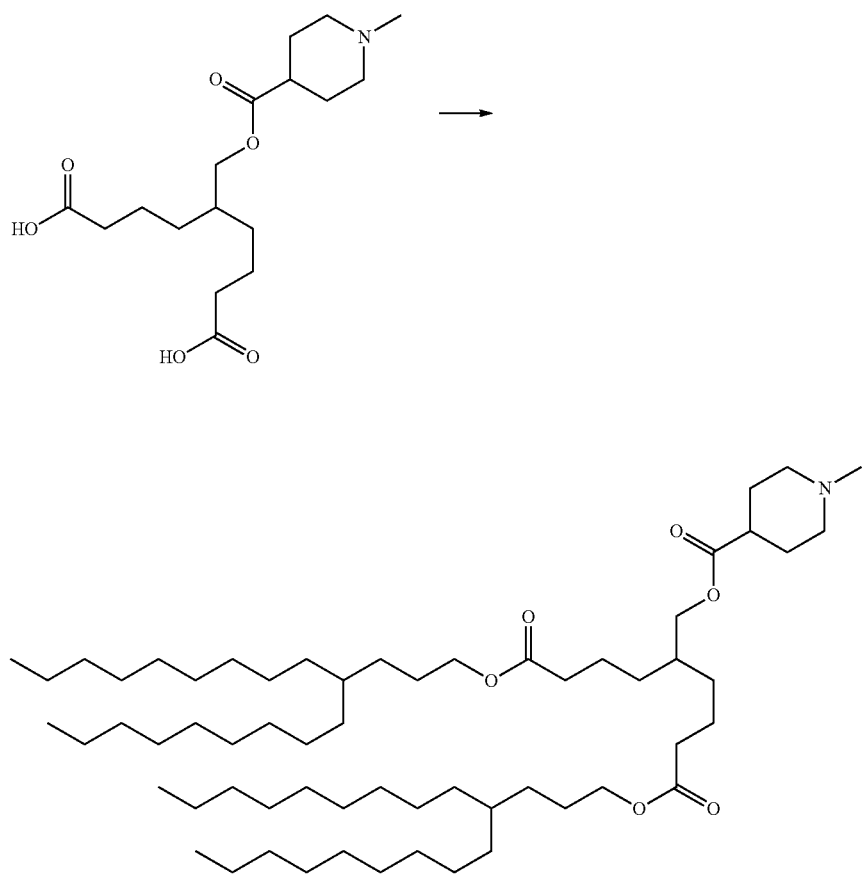

According to the method in Example A-13-(7), the titled compound (46 mg, 0.05 mmol) was obtained from the compound (80 mg, 0.23 mmol) obtained in Example A-18-(5), the compound (198 mg, 0.61 mmol) obtained in Production Example 5-(4), DMAP (6 mg, 0.05 mmol), EDC (98 mg, 0.51 mmol) and methylene chloride (5 mL).

$^1$H-NMR (600 MHz, CDCl$_3$) δ(ppm): 0.88 (t, J=6.97 Hz, 12H), 1.17-1.41 (m, 77H), 1.57-1.72 (m, 9H), 1.72-1.81 (m, 2H), 1.85-1.94 (m, 2H), 1.94-2.03 (m, 2H), 2.23-2.31 (m, 8H), 2.80 (m, J=10.5 Hz, 2H), 4.00 (d, J=5.50 Hz, 2H), 4.03 (t, J=6.88 Hz, 4H).

Synthesis of Cationic Lipid (21)
Example A-21
Diundecyl 7-{[(1-methylpiperidine-4-carbonyl)oxy]methyl}tridecanedioate (Cationic Lipid 21)
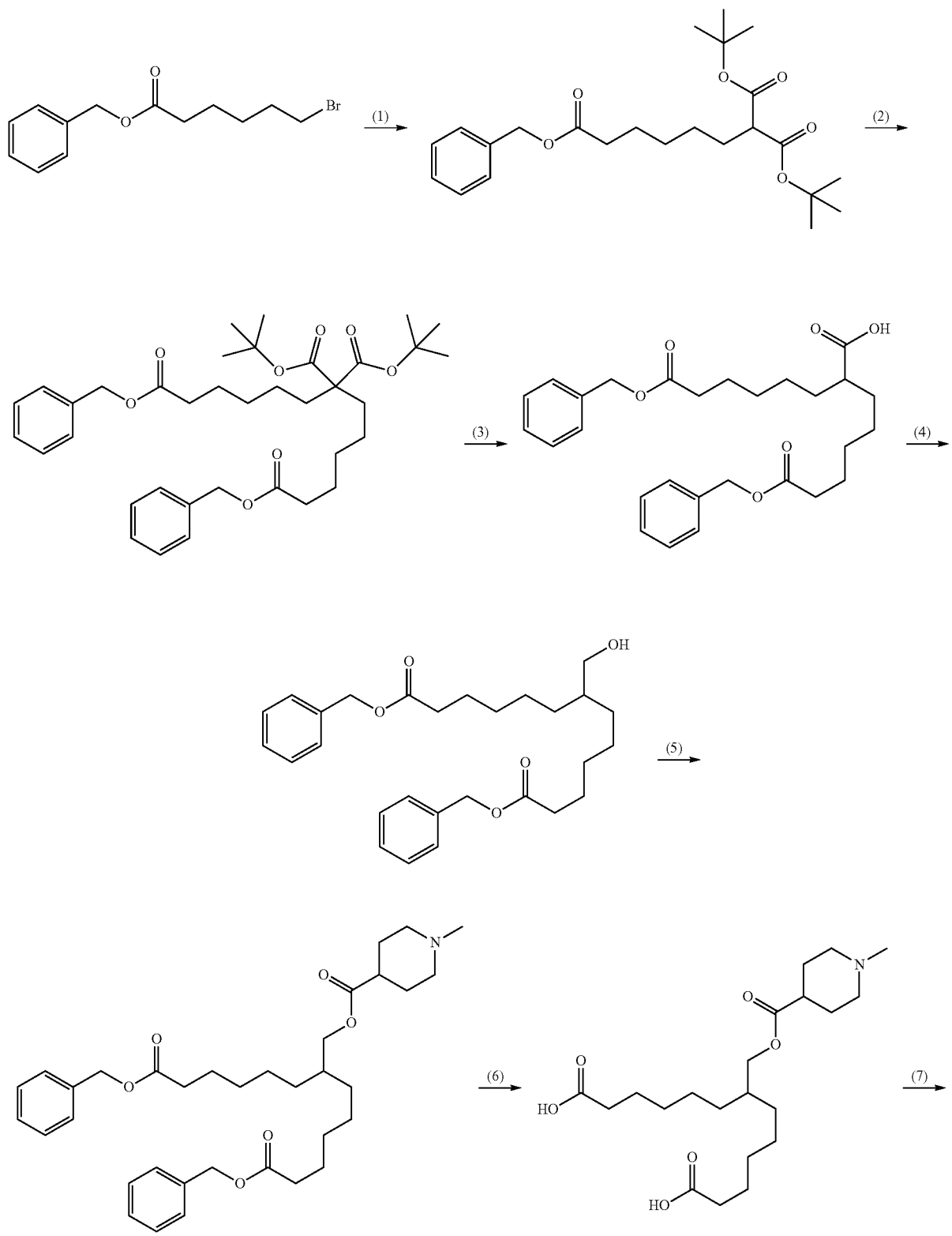

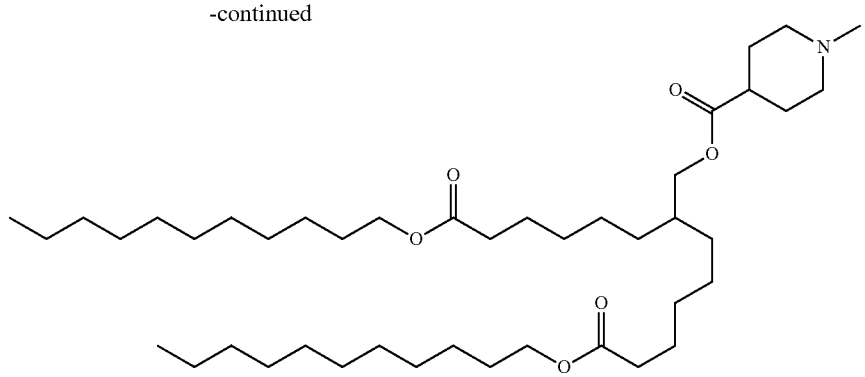

(1) Synthesis of 6-benzyl 1,1-di-tert-butyl hexane-1,1,6-tricarboxylate

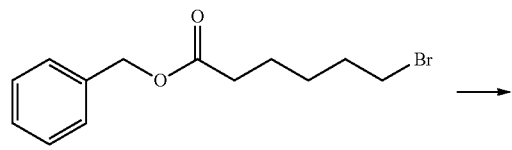

60% Sodium hydride (0.80 g, 20.0 mmol) was suspended in THF (35 mL), to which di-tert-butyl malonate (4.48 mL, 20.0 mmol) was added dropwise under ice cooling, and the mixture was stirred at room temperature for 15 minutes. Under ice cooling, sodium iodide (0.29 g, 1.90 mmol) was added and a solution of the compound (5.43 g, 19.0 mmol) obtained in Production Example 9 in THF (10 mL) was then added dropwise and the mixture was stirred at room temperature for 18 hours. The reaction mixture was extracted with diethyl ether and washed with water and the aqueous layer was diluted with diethyl ether. Organic layers were combined, washed with a saturated sodium chloride solution and dried over anhydrous magnesium sulphate. Following filtration, the solvent was removed by distillation under reduced pressure. The residue was purified by silica gel column chromatography (cyclohexane/ethyl acetate) to obtain the titled compound (6.01 g, 14.3 mmol).

$^1$H-NMR (600 MHz, CDCl$_3$) δ(ppm): 1.27-1.38 (m, 4H), 1.45 (s, 18H), 1.62-1.68 (m, 2H), 1.73-1.82 (m, 2H), 2.35 (t, J=7.52 Hz, 2H), 3.09 (t, J=7.61 Hz, 1H), 5.11 (s, 2H), 7.29-7.40 (m, 5H).

(2) Synthesis of 1,11-dibenzyl 6,6-di-tert-butyl undecane-1,6,6,11-tetracarboxylate

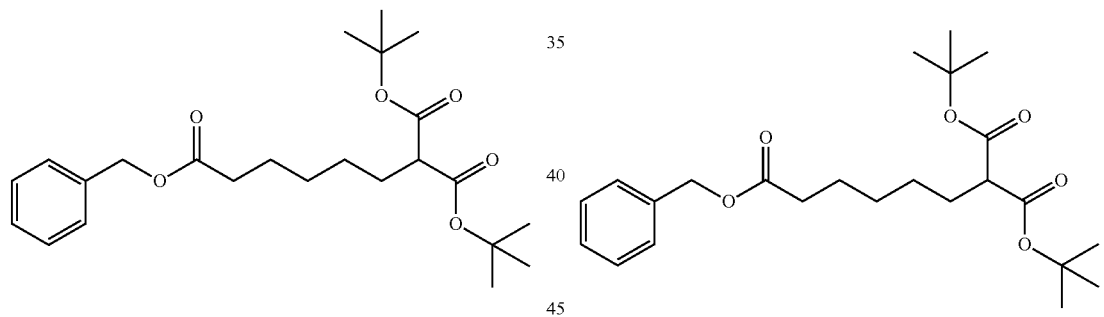

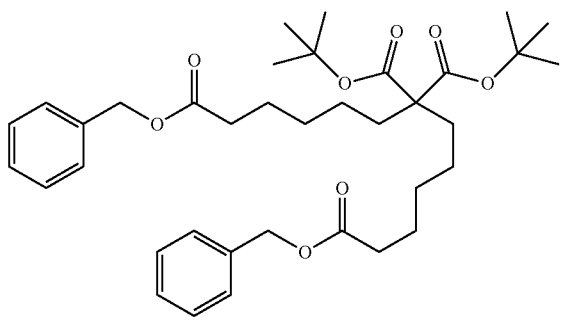

According to the method in Example A-18-(1), the titled compound (5.18 g, 8.29 mmol) was obtained from the compound (4.0 g, 9.51 mmol) obtained in Example A-21-(I), 60% sodium hydride (0.42 g, 10.5 mmol), the compound (3.25 g, 11.4 mmol) obtained in Production Example 9 and THF (30 mL).

¹H-NMR (600 MHz, CDCl₃) δ(ppm): 1.09-1.19 (m, 4H), 1.28-1.36 (m, 5H), 1.43 (s, 18H), 1.60-1.69(m, 4H), 1.72-1.80 (m, 4H), 2.34 (t, J=7.52 Hz, 4H), 5.05-5.15 (m, 4H), 7.28-7.41 (m, 9H).

(3) Synthesis of 8-(benzyloxy)-2-[6-(benzyloxy)-6-oxohexyl]-8-oxooctanoic acid

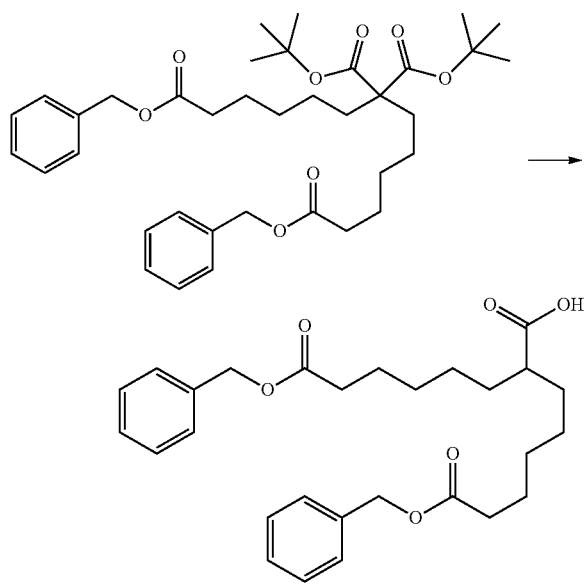

According to the method in Example A-13-(3), the titled compound (2.49 g, 5.31 mmol) was obtained from the compound (5.18 g, 8.29 mmol) obtained in Example A-21-(2), TFA (10 mL), methylene chloride (20 mL) and xylene (25 mL).

¹H-NMR (600 MHz, DMSO-d6) δ(ppm): 1.15-1.57 (m, 16H), 2.11-2.20 (m, 1H), 2.33 (t, J=7.34 Hz, 4H), 5.08 (s, 4H), 7.23-7.43 (m, 10H), 12.01 (br s, 1H).

(4) Synthesis of dibenzyl 7-(hydroxymethyl)tridecanedioate

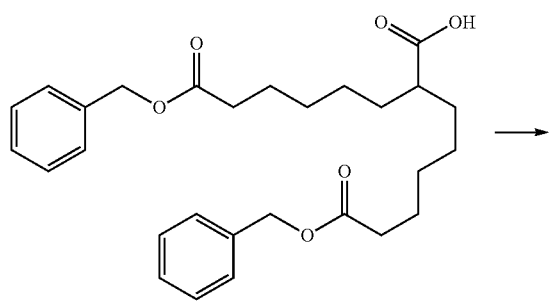

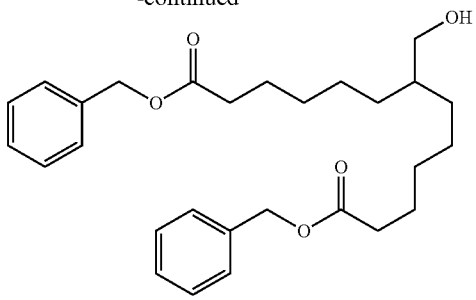

According to the method in Example A-18-(3), the titled compound (1.95 g, 4.29 mmol) was obtained from the compound (2.49 g, 5.31 mmol) obtained in Example A-21-(3), borane-THF complex (1 M, 13.2 mL, 13.2 mmol) and THF (20 mL).

¹H-NMR (600 MHz, CDCl₃) δ(ppm): 1.11-1.36 (m, 13H), 1.39-1.46 (m, 1H), 1.60-1.70 (m, 4H), 2.35 (t, J=7.52 Hz, 4H), 3.51 (d, J=5.32 Hz, 2H), 5.11 (s, 4H), 7.29-7.40 (m, 10H).

(5) Synthesis of dibenzyl 7-{[(1-methylpiperidine-4-carbonyl)oxy]methyl}tridecanedioate

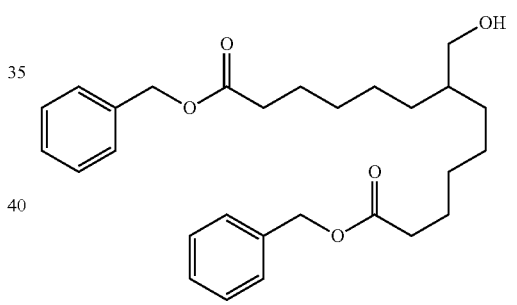

According to the method in Example A-13-(5), the titled compound (2.97 g, 6.09 mmol) was obtained from the compound (1.95 g, 4.29 mmol) obtained in Example A-21-(4), DIPEA (1.5 mL, 8.58 mmol), 1-methyl-piperidine-4- carboxylic acid hydrochloride (1.54 g, 8.58 mmol), DMAP (0.11 g, 0.86 mmol), EDC (1.81 g, 9.44 mmol) and methylene chloride (20 mL).

¹H-NMR (600 MHz, CDCl₃) δ(ppm): 1.22-1.35 (m, 12H), 1.61-1.68 (m, 4H), 1.70-1.84 (m, 3H), 1.85-1.93 (m, 2H), 1.95-2.06 (m, 2H), 2.21-2.30 (m, 4H), 2.35 (t, J=7.52 Hz, 4H), 2.74-2.85 (m, 2H), 3.96 (d, J=5.50 Hz, 2H), 5.11 (s, 4H), 7.29-7.39 (m, 10H).

(6) Synthesis of 7-{[(1-methylpiperidine-4-carbonyl)oxy]methyl}tridecanedioic acid

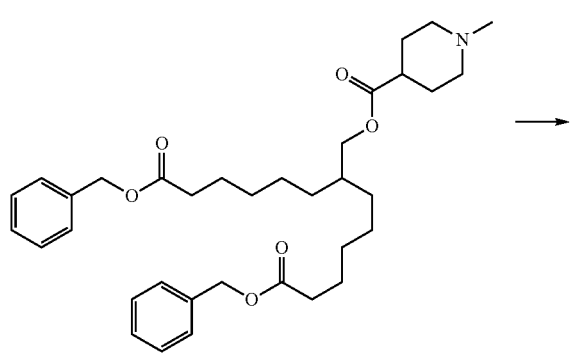

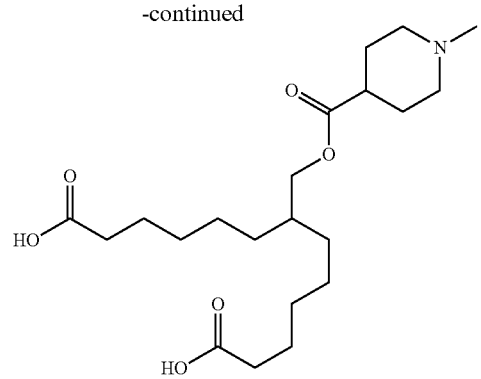

According to the method in Example A-16-(1), the titled compound (1.34 g, 3.35 mmol) was obtained from the compound (2.28 g, 3.93 mmol) obtained in Example A-21-(5), 10% palladium-carbon (0.42 g, 0.39 mmol, containing 50% water) and ethanol (20 mL).

¹H-NMR (600 MHz, DMSO-d6) δ(ppm): 1.19-1.30 (m, 12H), 1.44-1.53 (m, 4H), 1.53-1.63 (m, 3H), 1.72-1.81 (m, 2H), 1.90-1.98 (m, 2H), 2.14 (s, 3H), 2.18 (t, J=7.43 Hz, 4H), 2.23-2.31 (m, 1H), 2.64-2.73 (m, 2H), 3.93 (d, J=5.50 Hz, 2H).

(7) Synthesis of diundecyl 7-{[(1-methylpiperidine-4-carbonyl)oxy]methyl}tridecanedioate

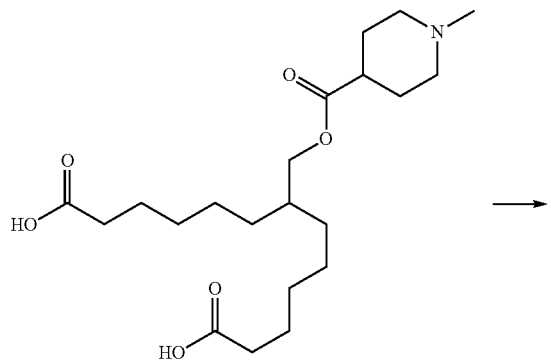

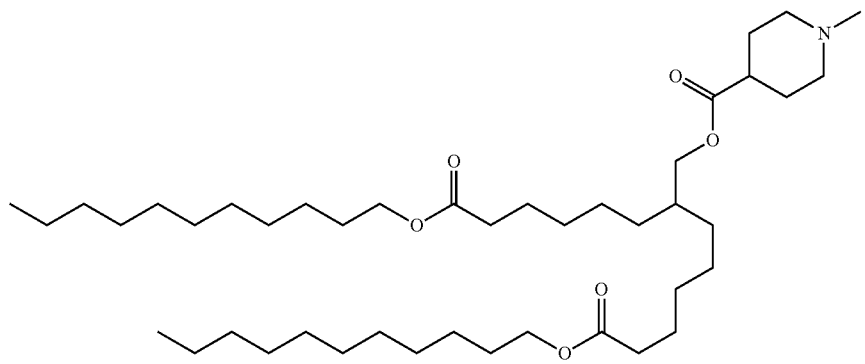

The compound (200 mg, 0.50 mmol) obtained in Example A-21-(6), undecan-1-ol (83 µL, 1.20 mmol) and DMAP (24 mg, 0.20 mmol) were dissolved in methylene chloride (10 mL), to which EDC (230 mg, 1.20 mmol) was added at room temperature, and the mixture was stirred at room temperature for 18 hours. The mixture was added with a saturated sodium hydrogen carbonate aqueous solution and extracted with methylene chloride, and the organic layer was then concentrated under reduced pressure. The residue was purified by silica gel column chromatography (ethyl acetate/cyclohexane/methanol) to obtain the titled compound (220 mg, 0.32 mmol).

$^1$H-NMR (600 MHz, CDCl$_3$) δ(ppm): 0.88 (t, J=7.06 Hz, 6H), 1.19-1.39 (m, 44H), 1.57-1.68 (m, 9H) 1.71-1.86 (m, 2H), 1.84-1.95 (m, 2H), 1.95-2.06 (m, 2H), 2.21-2.34 (m, 8H), 2.75-2.87 (m, 2H), 3.97 (d, J=5.69 Hz, 2H), 4.05 (t, J=6.79 Hz, 4H).

Synthesis of Cationic Lipid (22)

Example A-22

Bis(4-heptylundecyl) 7-{[(1-methylpiperidine-4-carbonyl)oxy]methyl}tridecanedioate (Cationic Lipid 22)

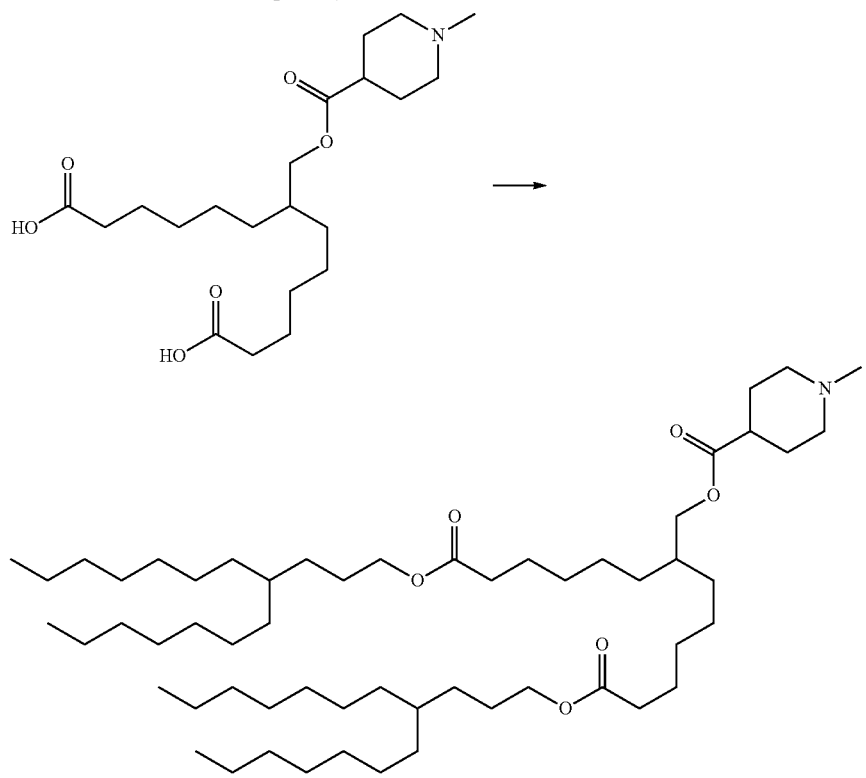

According to the method in Example A-16-(2), the titled compound (88 mg, 0.10 mmol) was obtained from the compound (200 mg, 0.25 mmol) obtained in Example A-21-(6), the compound (160 mg, 0.60 mmol) obtained in Production Example 6-(2), DMAP (12 mg, 0.10 mmol), EDC (120 mg, 0.60 mmol) and methylene chloride (5 mL).

$^1$H-NMR (600 MHz, CDCl$_3$) δ(ppm): 0.88 (t, J=6.97 Hz, 12H), 1.11-1.36 (m, 66H), 1.49-1.67 (m, 9H), 1.71-1.84 (m, 2H), 1.84-1.95 (m, 2H), 1.95-2.05 (m, 2H), 2.21-2.33 (m, 8H), 2.74-2.88 (m, 2H), 3.97 (d, J=5.50 Hz, 2H), 4.04 (t, J=6.88 Hz, 4H).

The synthesized cationic lipids 1 to 22 are indicated in Table A below.

TABLE A

Synthesized cationic lipids 1 to 22

Structure

Cationic lipid 1:
2-{9-[(2-butyloctyl)oxy]-9-oxononyl}
dodecyl 1-methylpiperidine-
4-carboxylate

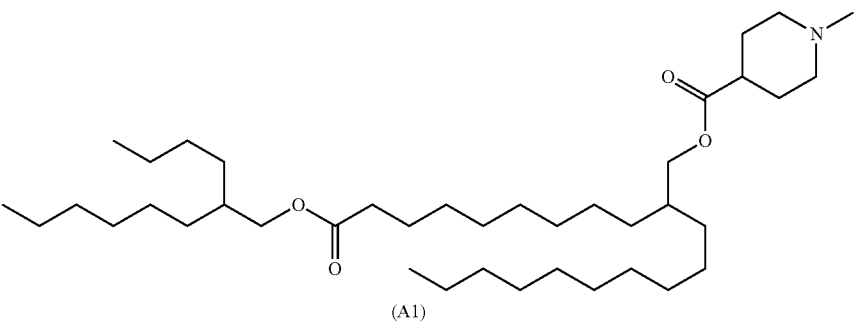

(A1)

Cationic lipid 2:
2-{9-oxo-9-[(3-pentyloctyl)oxy]nonyl}
dodecyl 1-methylpiperidine-
4-carboxylate

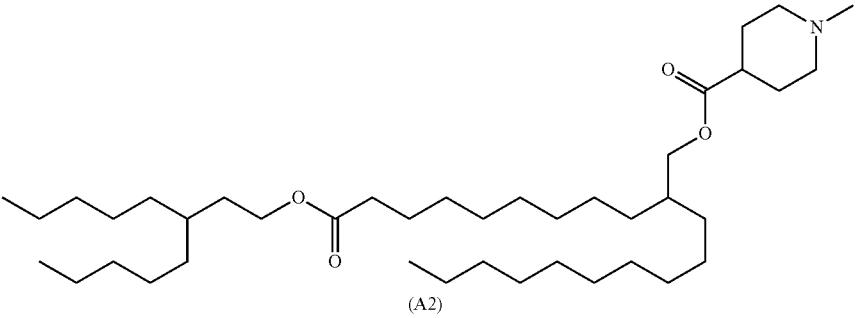

(A2)

Cationic lipid 3:
2-nonyl-11-oxo-11-[(3-pentyloctyl)
oxy]undecyl 1-methylpiperidine-
4-carboxylate

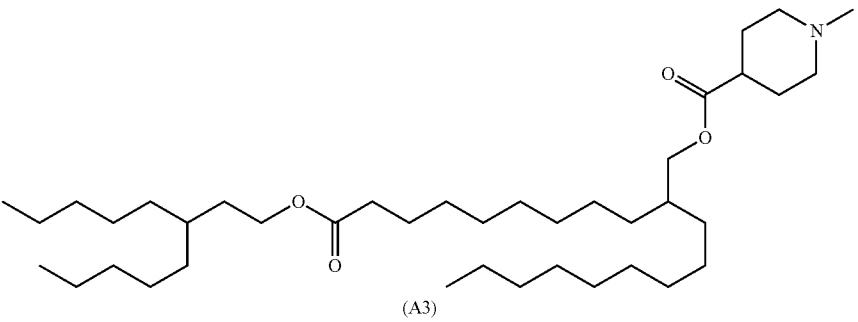

(A3)

Cationic lipid 4:
bis(3-pentyloctyl)
9-{[(1-methylpiperidine-4-carbonyl)
oxy]methyl}heptadecanedioate

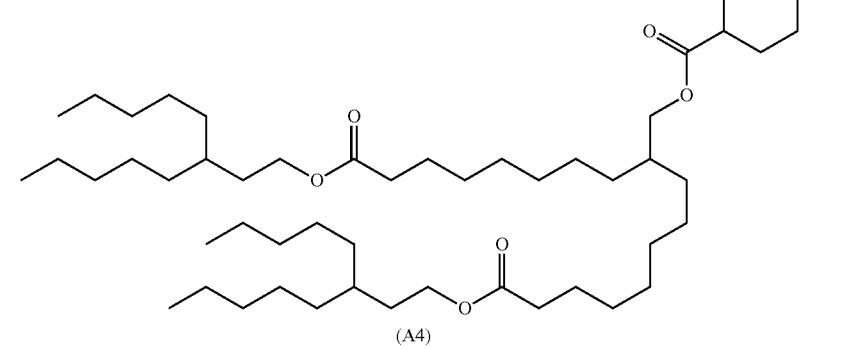

(A4)

TABLE A-continued

Synthesized cationic lipids 1 to 22

Structure

Cationic lipid 5:
di[(Z)-2-nonen-1-yl]
9-{[(1-methylpiperidine-4-carbonyl)
oxy]methyl}heptadecanedioate

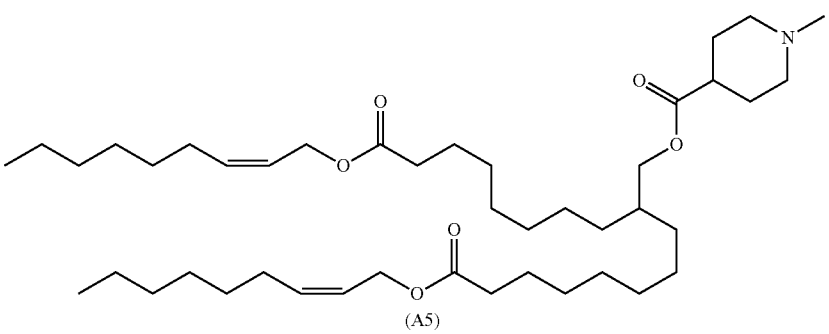

(A5)

Cationic lipid 6:
(1R,5S,6r)-2-{9-[(2-butyloctyl)oxy]-
9-oxononyl}dodecyl
3-methyl-3-azabicyclo[3.1.0]
hexane-6-carboxylate

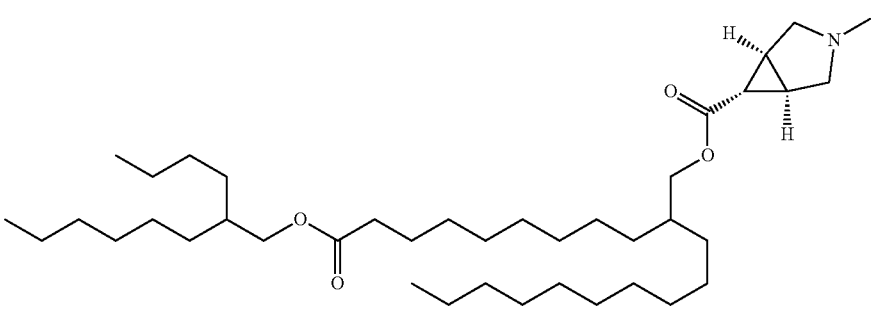

(A6)

Cationic lipid 7:
(1R,5S,6s)-2-{9-[(2-butyloctyl)oxy]-
9-oxononyl}dodecyl
3-methyl-3-azabicylco[3.1.0]
hexane-6-carboxylate

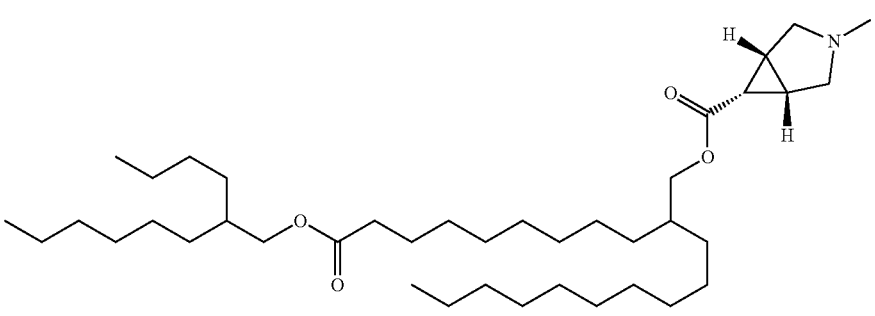

(A7)

Cationic lipid 8:
2-{9-[(2-butyloctyl)oxy]-9-oxononyl}
dodecyl 4-methylpiperazine-1-
carboxylate

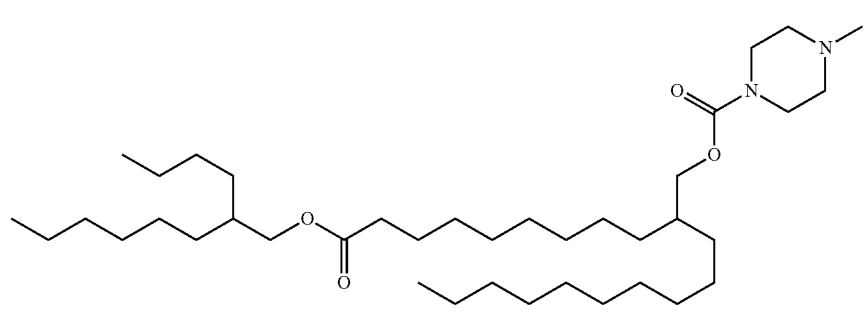

(A8)

TABLE A-continued

Synthesized cationic lipids 1 to 22

| | Structure |
|---|---|
| Cationic lipid 9:<br>2-[9-(hexyloxy)-9-oxononyl]dodecyl<br>1-methylpiperidine-4-carboxylate | 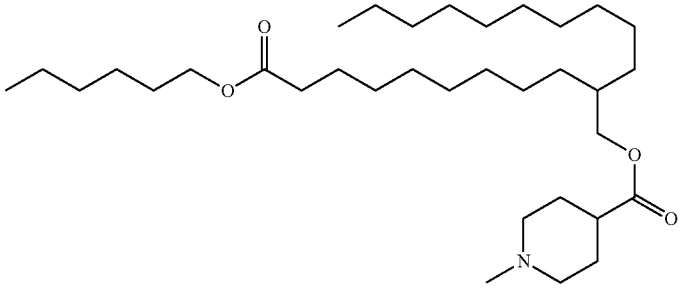<br>(A9) |
| Cationic lipid 10:<br>2-[9-(octyloxy)-9-oxononyl]dodecyl<br>1-methylpiperidine-4-carboxylate | 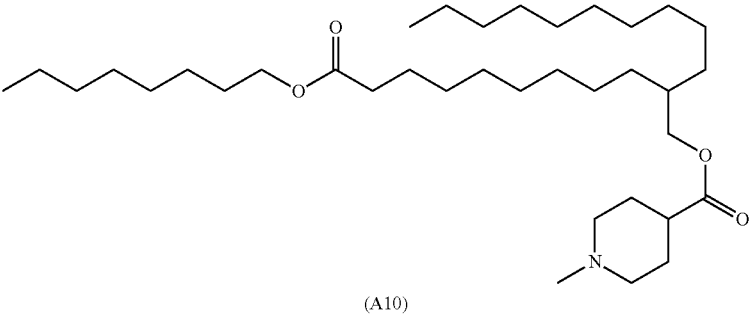<br>(A10) |
| Cationic lipid 11:<br>2-[9-(decyloxy)-9-oxononyl]dodecyl<br>1-methylpiperidine-4-carboxylate | 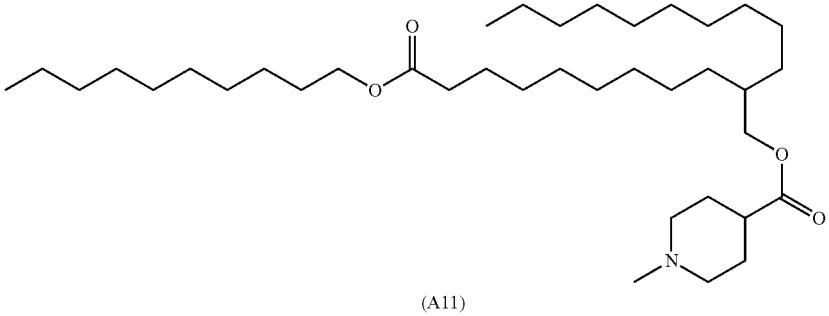<br>(A11) |
| Cationic lipid 12:<br>2-{9-oxo-9-[(4-pentylnonyl)oxy]<br>nonyl}dodecyl 1-methylpiperidine-<br>4-carboxylate | 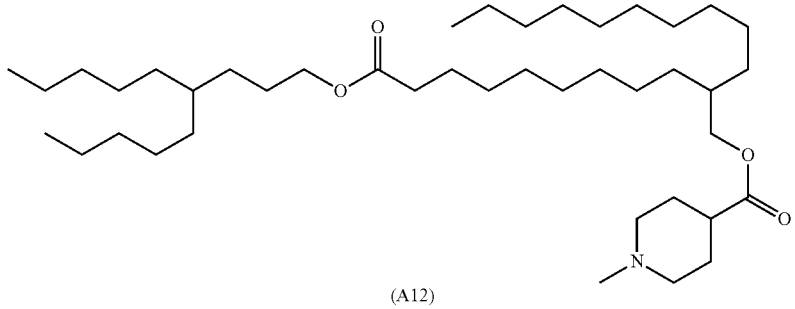<br>(A12) |

TABLE A-continued

Synthesized cationic lipids 1 to 22

Structure

Cationic lipid 13:
2-(4-oxo-4-(tridecyloxy)butyl)dodecyl
1-methylpiperidine-4-carboxylate

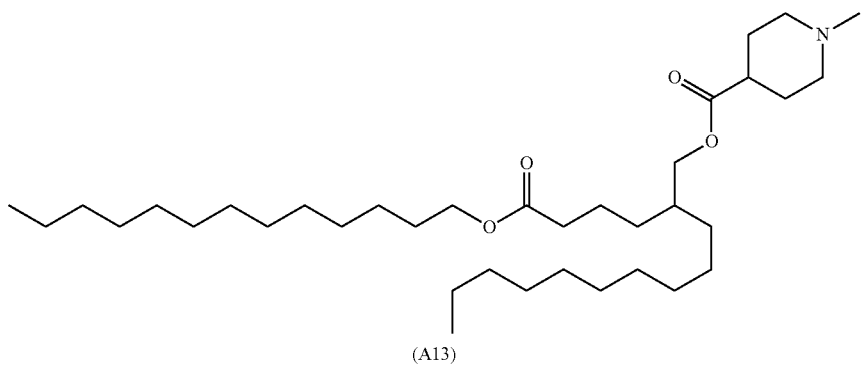

(A13)

Cationic lipid 14:
2-(4-oxo-4-((8-pentyltridecyl)oxy)
butyl)dodecyl 1-methylpiperidine-
4-carboxylate

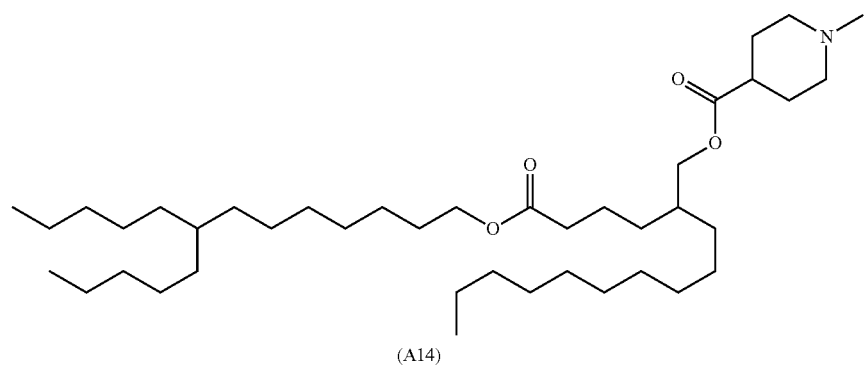

(A14)

Cationic lipid 15:
2-{4-[(4-Nonyltridecyl)oxy]-4-
oxobutyl}dodecyl
1-methylpiperidine-4-carboxylate

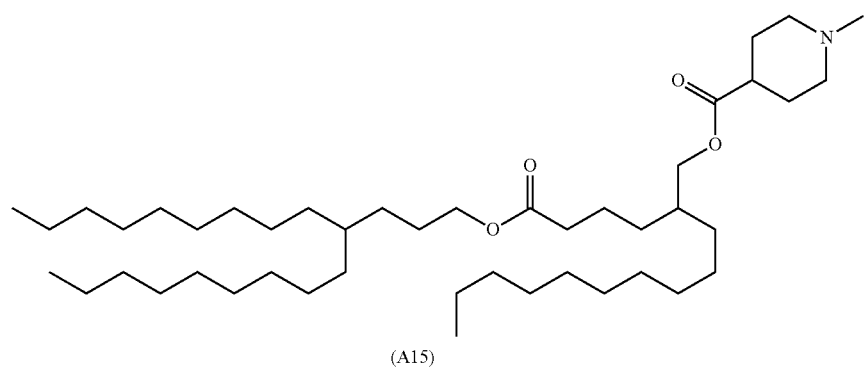

(A15)

Cationic lipid 16:
Dioctyl 9-{[(1-methylpiperidine-4-
carbonyl)oxy]methyl}
heptadecanedioate

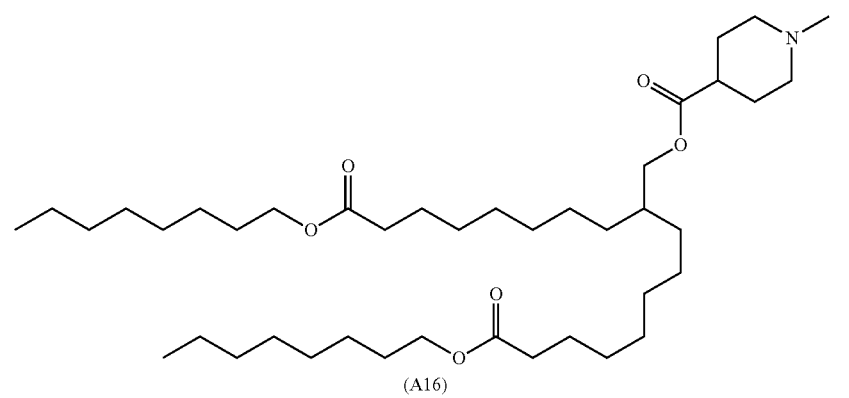

(A16)

TABLE A-continued
Synthesized cationic lipids 1 to 22
Structure
Cationic lipid 17:
Bis(4-pentylnonyl) 9-{[(1-methylpiperidine-4-carbonyl)oxy]methyl} heptadecanedioate
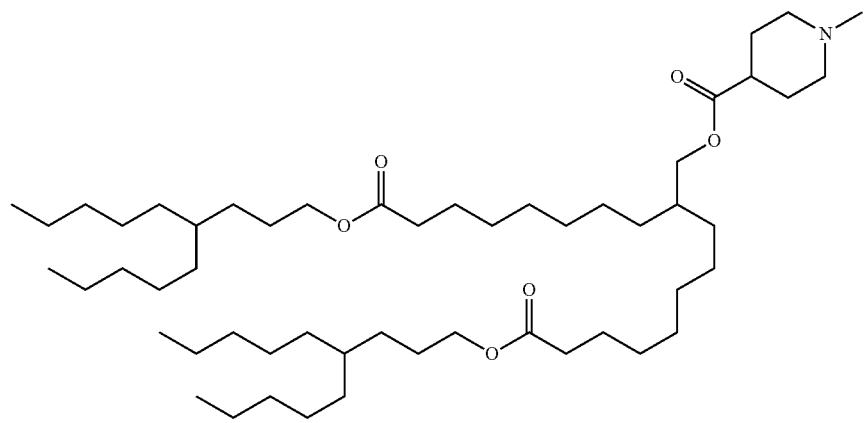
(A17)
Cationic lipid 18:
Ditridecyl 5-{[(1-methylpiperidine-4-carbonyl)oxy]methyl}nonanedioate
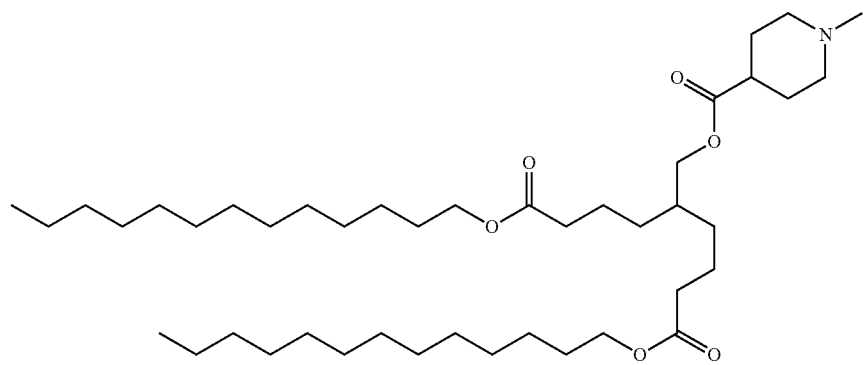
(A18)
Cationic lipid 19:
Bis(8-pentyltridecyl) 5-{[(1-methylpiperidine-4-carbonyl)oxy]methyl}nonanedioate
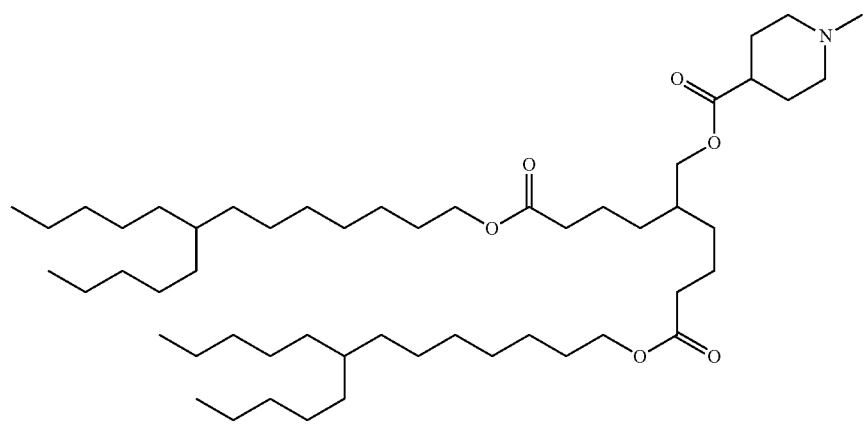
(A19)

TABLE A-continued
Synthesized cationic lipids 1 to 22
Structure
Cationic lipid 20:
Bis(4-nonyltridecyl)
5-{[(1-methylpiperidine-4-
carbonyl)oxy]methyl}nonanedioate
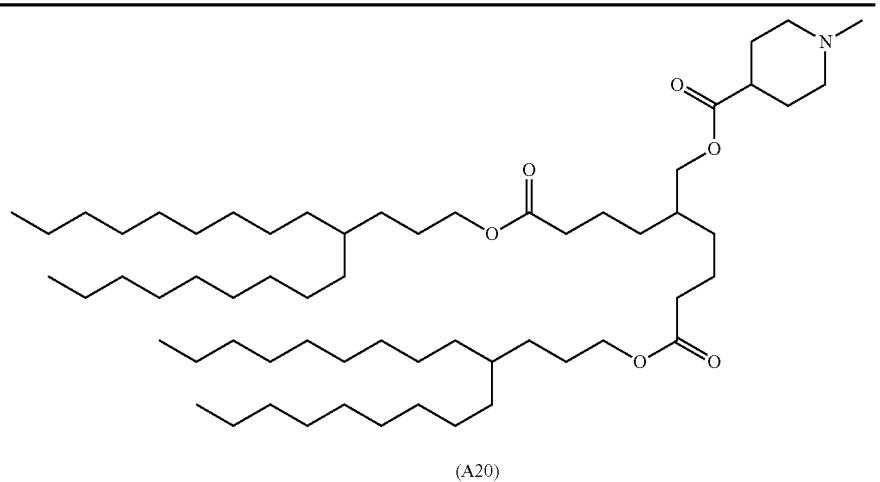
(A20)
Cationic lipid 21:
Diundecyl 7-{[(1-methylpiperidine-4-
carbonyl)oxy]methyl}tridecanedioate
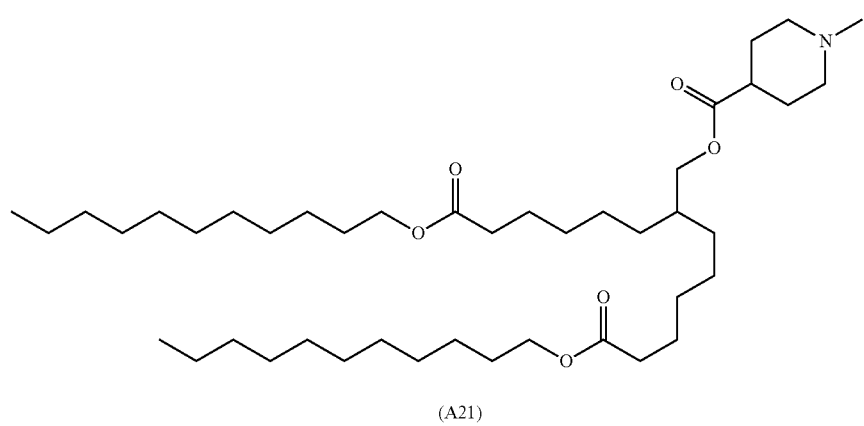
(A21)
Cationic lipid 22:
Bis(4-heptylundecyl)
7-{[(1-methylpiperidine-4-carbonyl)
oxy]methyl}tridecanedioate
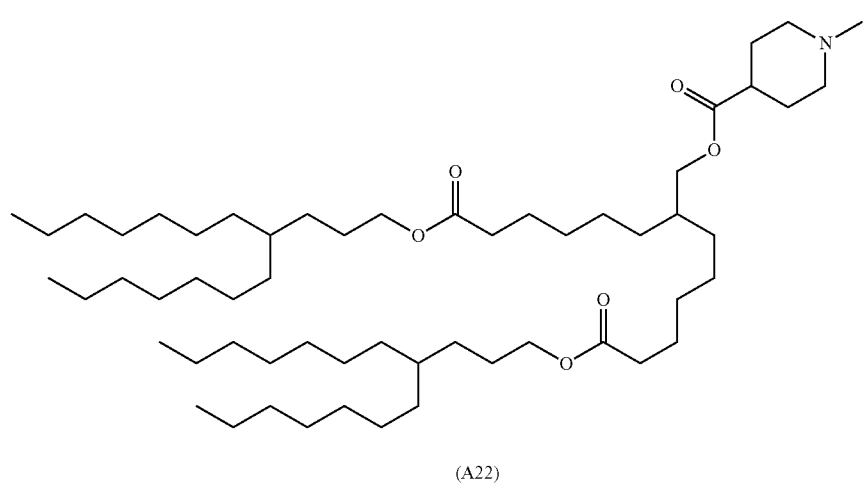
(A22)

B. Preparation and analysis of compositions

Preparation of Compositions (1)

Example B-1

A composition was prepared with cationic lipid 1 of Example A-1. As the nucleic acid, annealed siRNA (GeneDesign Inc., hereinafter also referred to as "Factor VII siRNA") that silences expression of the Factor VII (blood coagulation factor VII) gene and consists of a sense strand having a base sequence: 5'-GGAfUfCAfUfCfUfCfUfCAAGfUfCfUfUAfCT*T-3' (T: DNA, fU, fC=2'-Fluoro RNA, *=Phosphorothioate linkage) (SEQ ID NO: 1) and an antisense strand having a base sequence: 5'-GfUAAGAfCfUfUGGAAAfUGAfUfCfCT*T-3' (T: DNA, fU, fC=2'-Fluoro RNA, *=Phosphorothioate linkage) (SEQ ID NO: 2) was used.

Factor VII siRNA was dissolved in 25 mM sodium acetate (pH 4.0) at 80 μg/mL to obtain a diluted siRNA solution. Cationic lipid 1, DSPC (Nippon Fine Chemical Co., Ltd.), Cholesterol (Nippon Fine Chemical Co., Ltd.), MPEG2000-DMG (NOF Corporation) were dissolved in ethanol at a ratio of 60/8.5/30/1.5 (molar ratio) so that the total lipid concentration was set to 7.2 mM, and then a lipid solution was obtained. The diluted siRNA solution and the lipid solution were fed and mixed at flow rates of 3 mL/min and 1 mL/min, respectively, to obtain a lipid complex aqueous solution. The obtained lipid complex aqueous solution was subjected to dialysis using a dialysis membrane (product name "Float-A-Lyzer G2", SPECTRUM, Inc., 50K MWCO) to replace the external solution with phosphate buffer (PBS, pH 7.4). After the dialysis, concentration and filter sterilization were performed, thereby obtaining a liquid composition of Example B-1.

Example B-2

A composition of Example A-7 was obtained in the same manner as Example B-1 except that as the cationic lipid, cationic lipid 2 of Example A-2 was used instead of cationic lipid 1.

Example B-3

A composition of Example B-3 was obtained in the same manner as Example B-1 except that as the cationic lipid, cationic lipid 3 of Example A-3 was used instead of cationic lipid 1.

Example B-4

A composition of Example B-4 was obtained in the same manner as Example B-1 except that as the cationic lipid, cationic lipid 4 of Example A-4 was used instead of cationic lipid 1.

Example B-5

A composition of Example B-5 was obtained in the same manner as Example B-1 except that as the cationic lipid, cationic lipid 5 of Example A-5 was used instead of cationic lipid 1.

Example B-6

A composition of Example B-6 was obtained in the same manner as Example B-1 except that as the cationic lipid, cationic lipid 6 of Example A-6 was used instead of cationic lipid 1.

Example B-7

A composition of Example B-7 was obtained in the same manner as Example B-1 except that as the cationic lipid, cationic lipid 7 of Example A-7 was used instead of cationic lipid 1.

Example B-8

A composition of Example B-8 was obtained in the same manner as Example B-1 except that as the cationic lipid, cationic lipid 8 of Example A-8 was used instead of cationic lipid 1.

Comparative Example B-1

A composition of Comparative Example B-1 was obtained in the same manner as in Example B-1 except that as the cationic lipid, di((Z)-non-2-en-1-yl)9-((4-(dimethylamino) butanoyl)oxy)heptadecanedioate (hereinafter also referred to as "ALN-319") represented by formula (12) below disclosed in Patent Literature 2 that was synthesized according to the method disclosed in Patent Literature 2, was used instead of cationic lipid 1.

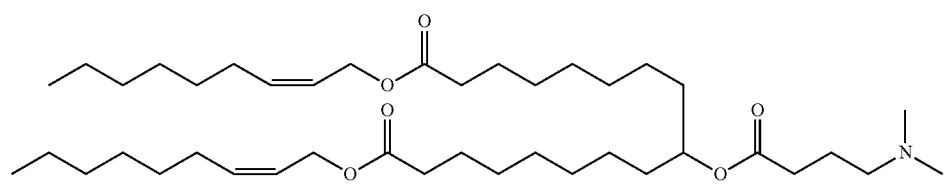

(12)

(Analysis of Compositions (1))

In the compositions of Example B-1 to Example B-8 and Comparative Example B-1, the encapsulation rate of siRNA into lipid complexes were measured.

Specifically, the siRNA concentration (A) measured with Quant-iT RiboGreen RNA Reagent (Invitrogen) after diluting a composition with RNase Free Water was set as the concentration of siRNA present in the external solution of the lipid complex. The siRNA concentration (B) measured after diluting the composition with 1% Triton X-100 was set as the total siRNA concentration in the composition. Next, according to formula (F1) below, the encapsulation rate of the nucleic acid was calculated.

$$\text{Encapsulation rate (\%)} = 100 - (A/B) \times 100 \tag{F1}$$

The average particle diameter of lipid complexes was measured using a particle diameter analyser (product name "Zetasizer Nano ZS", produced by Malvern Panalytical Ltd.).

Table 1 shows the encapsulation rate of siRNA and the average particle diameter (Z-average) and the polydispersion index of lipid complexes.

[Table 1]

TABLE 1

| Composition | Cationic lipid | Encapsulation rate (%) | Average particle diameter (nm) | Polydispersion index |
|---|---|---|---|---|
| Example B-1 | 1 | 98 | 87 | 0.11 |
| Example B-2 | 2 | 98 | 78 | 0.09 |
| Example B-3 | 3 | 98 | 77 | 0.10 |
| Example B-4 | 4 | 99 | 86 | 0.11 |
| Example B-5 | 5 | 96 | 76 | 0.14 |
| Example B-6 | 6 | 91 | 69 | 0.17 |
| Example B-7 | 7 | 96 | 69 | 0.14 |
| Example B-8 | 8 | 97 | 69 | 0.14 |
| Comparative Example B-1 | ALN-319 | 98 | 84 | 0.11 |

It is confirmed that the compositions of Example B-1 to Example B-8 exhibit high encapsulation rates of siRNA, equivalent to that of the composition of Comparative Example B-1.

Preparation of Compositions (2)

Example B-9

A composition was prepared with cationic lipid 1 of Example A-1. As the nucleic acid, mRNA of Firefly Luciferase (FLuc) (TriLink Biotechnologies, hereinafter also referred to as "FLuc mRNA") was used.

FLuc mRNA was dissolved in 50 mM sodium acetate (pH 4.0) at 27 µg/mL to obtain a diluted mRNA solution. Cationic lipid 1, DSPC (Nippon Fine Chemical Co., Ltd.), Cholesterol (Nippon Fine Chemical Co., Ltd.), MPEG2000-DMG (NOF Corporation) were dissolved in ethanol at a ratio of 60/8.5/30/1.5 (molar ratio) so that a total lipid concentration was set to 2.4 mM and a lipid solution was obtained. The diluted mRNA solution and the lipid solution were fed and mixed at flow rates of 3 mL/min and 1 mL/min, respectively, to obtain a lipid complex aqueous solution. The obtained lipid complex aqueous solution was subjected to dialysis using a dialysis membrane (product name "Float-A-Lyzer G2", SPECTRUM, Inc., 50K MWCO) to replace the external solution with phosphate buffer (PBS, pH 7.4). After the dialysis, concentration and filter sterilization was performed, thereby obtaining a composition of Example B-9.

Example B-10

A composition of Example B-10 was obtained in the same manner as Example B-9 except that as the cationic lipid, cationic lipid 2 of Example A-2 was used instead of cationic lipid 1.

Comparative Example B-2

A composition of Comparative Example B-2 was obtained in the same manner as Example B-9 except that as the cationic lipid, ALN-319 described above was used instead of cationic lipid 1.

(Analysis of Compositions (2))

In the same manner as in analysis of compositions (1), the encapsulation rate of mRNA in lipid complexes and the average particle diameter of the lipid complexes were measured for the compositions of Example B-9, Example B-10 and Comparative Example B-2. Table 2 shows the encapsulation rate of mRNA and the average particle diameter (Z-average) of lipid complexes.

[Table 2]

TABLE 2

| Composition | Cationic lipid | Encapsulation rate (%) | Average particle diameter (nm) | Polydispersion index |
|---|---|---|---|---|
| Example B-9 | 1 | 94 | 104 | 0.06 |
| Example B-10 | 2 | 92 | 110 | <0.01 |
| Comparative Example B-2 | ALN-319 | 95 | 125 | 0.04 |

It is confirmed that the compositions of Example B-9 and Example B-10 exhibit high encapsulation rates of mRNA, equivalent to that of the composition of Comparative Example B-2.

Preparation of Compositions (3)

Example B-11

A composition was prepared with cationic lipid 2 of Example A-2. A composition of Example B-11 was obtained in the same manner as in Example B-9 except that as the cationic lipid, cationic lipid 2 was used instead of cationic lipid 1 and as the nucleic acid, Human Erythropoietin (hEPO) mRNA (TriLink Biotechnologies, hereinafter also referred to as "EPO mRNA") was used instead of FLuc mRNA.

Comparative Example B-3

A composition of Comparative Example B-3 was obtained in the same manner as in Example B-11 except that as the cationic lipid, ALN-319 described above was used instead of cationic lipid 2.

(Analysis of Compositions (3))

In the same manner as in analysis of compositions (1), the encapsulation rate of mRNA in lipid complexes and the average particle diameter of the lipid complexes were measured for the compositions of Example B-11 and Comparative Example B-3. Table 3 shows the encapsulation rate of mRNA and the average particle diameter (Z-average) of lipid complexes.

[Table 3]

TABLE 3

| Composition | Cationic lipid | Encapsulation rate (%) | Average particle diameter (nm) | Polydispersion index |
|---|---|---|---|---|
| Example B-11 | 2 | 98 | 109 | 0.06 |
| Comparative Example B-3 | ALN-319 | 92 | 127 | 0.06 |

It is confirmed that the composition of Example B-11 exhibits a high encapsulation rate of mRNA, equivalent to that of the composition of Comparative Example B-3.

Preparation of Compositions (4)

Example B-12

In the same manner as in preparation of compositions (1), a composition of Example B-12 containing Factor VII siRNA was obtained using cationic lipid 1 of Example A-1.

Example B-13

A composition of Example B-13 was obtained in the same manner as in Example B-12 except that as the cationic lipid, cationic lipid 2 of Example A-2 was used instead of cationic lipid 1.

Comparative Example B-4

A composition of Comparative Example B-4 was obtained in the same manner as in Example B-12 except that as the cationic lipid, ALN-319 described above was used instead of cationic lipid 1.

(Analysis of Compositions (4))

In the same manner as in analysis of compositions (1), the average particle diameter (pre-storage average particle diameter) of lipid complexes were measured for the compositions of Example B-12, Example B-13 and Comparative Example B-4. The compositions were further stored in sealed vials at 4° C. for 3 months and the average particle diameter (post-storage average particle diameter) of lipid complexes was measured. Table 4 shows the change in the average particle diameter (Z-average) of lipid complexes. In the table, the change (%) in the average particle diameter was calculated by post-storage average particle diameter/pre-storage average particle diameter×100.

[Table 4]

TABLE 4

| Composition | Cationic lipid | Pre-storage average particle diameter (nm) | Post-storage average particle diameter (nm) | Change in average particle diameter (%) |
|---|---|---|---|---|
| Example B-12 | 1 | 91 | 96 | 105 |
| Example B-13 | 2 | 90 | 92 | 102 |
| Comparative Example B-4 | ALN-319 | 76 | 115 | 151 |

It was demonstrated that the compositions of Example B-12 and Example B-13 had average particle diameters that hardly changed after a storage over 3 months and were physically more stable than the composition of Comparative Example B-4.

Preparation of Compositions (5)

Example B-14

In the same manner as in preparation of compositions (1), a composition of Example B-14 containing Factor VII siRNA was obtained using cationic lipid 9 of Example A-9.

Example B-15

A composition of Example B-15 was obtained in the same manner as in Example B-14 except that as the cationic lipid, cationic lipid 10 of Example A-10 was used instead of cationic lipid 9.

Example B-16

A composition of Example B-16 was obtained in the same manner as in Example B-14 except that as the cationic lipid, cationic lipid 11 of Example A-11 was used instead of cationic lipid 9.

Example B-17

A composition of Example B-17 was obtained in the same manner as in Example B-14 except that as the cationic lipid, cationic lipid 12 of Example A-12 was used instead of cationic lipid 9.

Example B-18

A composition of Example B-18 was obtained in the same manner as in Example B-14 except that as the cationic lipid, cationic lipid 13 of Example A-13 was used instead of cationic lipid 9.

Example B-19

A composition of Example B-19 was obtained in the same manner as in Example B-14 except that as the cationic lipid, cationic lipid 14 of Example A-14 was used instead of cationic lipid 9.

Example B-20

A composition of Example B-20 was obtained in the same manner as in Example B-14 except that as the cationic lipid, cationic lipid 15 of Example A-15 was used instead of cationic lipid 9.

Example B-21

A composition of Example B-21 was obtained in the same manner as in Example B-14 except that as the cationic lipid, cationic lipid 2 of Example A-2 was used instead of cationic lipid 9.

(Analysis of Compositions (5))

In the same manner as in analysis of compositions (1), the encapsulation rate of siRNA in lipid complexes and the average particle diameter of lipid complexes were measured for the compositions of Example B-14 to Example B-21. Table 5 shows the encapsulation rate of siRNA and the average particle diameter (Z-average) and the polydispersion index of lipid complexes.

[Table 5]

TABLE 5

| Composition | Cationic lipid | Encapsulation rate (%) | Average particle diameter (nm) | Polydispersion index |
|---|---|---|---|---|
| Example B-14 | 9 | 80 | 84 | 0.11 |
| Example B-15 | 10 | 94 | 78 | 0.14 |
| Example B-16 | 11 | 96 | 71 | 0.06 |
| Example B-17 | 12 | 98 | 78 | 0.16 |
| Example B-18 | 13 | 99 | 77 | 0.12 |
| Example B-19 | 14 | 99 | 73 | 0.05 |
| Example B-20 | 15 | 99 | 74 | 0.06 |
| Example B-21 | 2 | 99 | 87 | 0.16 |

Preparation of Compositions (6)

Example B-22

In the same manner as in preparation of compositions (1), a composition of Example B-22 containing Factor VII siRNA was obtained using cationic lipid 16 of Example A-16.

Example B-23

A composition of Example B-23 was obtained in the same manner as in Example B-22 except that as the cationic lipid, cationic lipid 17 of Example A-17 was used instead of cationic lipid 16.

Example B-24

A composition of Example B-24 was obtained in the same manner as in Example B-22 except that as the cationic lipid, cationic lipid 18 of Example A-18 was used instead of cationic lipid 16.

Example B-25

A composition of Example B-25 was obtained in the same manner as in Example B-22 except that as the cationic lipid, cationic lipid 19 of Example A-19 was used instead of cationic lipid 16.

Example B-26

A composition of Example B-26 was obtained in the same manner as in Example B-22 except that as the cationic lipid, cationic lipid 20 of Example A-20 was used instead of cationic lipid 16.

Example B-27

A composition of Example B-27 was obtained in the same manner as in Example B-22 except that as the cationic lipid, cationic lipid 21 of Example A-21 was used instead of cationic lipid 16.

Example B-28

A composition of Example B-28 was obtained in the same manner as in Example B-22 except that as the cationic lipid, cationic lipid 22 of Example A-22 was used instead of cationic lipid 16.

Example B-29

A composition of Example B-29 was obtained in the same manner as in Example B-22 except that as the cationic lipid, cationic lipid 2 of Example A-2 was used instead of cationic lipid 16.

(Analysis of Compositions (6))

In the same manner as in analysis of compositions (1), the encapsulation rate of siRNA in lipid complexes and the average particle diameter of lipid complexes were measured for the compositions of Example B-22 to Example B-29. Table 6 shows the encapsulation rate of siRNA and the average particle diameter (Z-average) and the polydispersion index of lipid complexes.

[Table 6]

TABLE 6

| Composition | Cationic lipid | Encapsulation rate (%) | Average particle diameter (nm) | Polydispersion index |
|---|---|---|---|---|
| Example B-22 | 16 | 72 | 87 | 0.12 |
| Example B-23 | 17 | 97 | 80 | 0.08 |
| Example B-24 | 18 | 97 | 90 | 0.13 |
| Example B-25 | 19 | 97 | 78 | 0.18 |
| Example B-26 | 20 | 97 | 91 | 0.11 |
| Example B-27 | 21 | 96 | 90 | 0.13 |
| Example B-28 | 22 | 97 | 82 | 0.14 |
| Example B-29 | 2 | 99 | 87 | 0.16 |

Preparation of Compositions (7)

Example B-30

In the same manner as in preparation of compositions (1), a composition of Example B-30 containing Factor VII siRNA was obtained using cationic lipid 1 of Example A-1.

Example B-31

A composition of Example B-30 was obtained in the same manner as in Example B-30 except that as the cationic lipid, cationic lipid 2 of Example A-2 was used instead of cationic lipid 1.

Example B-32

A composition of Example B-32 was obtained in the same manner as in Example B-30 except that as the cationic lipid, cationic lipid 3 of Example A-3 was used instead of cationic lipid 1.

Example B-33

A composition of Example B-33 was obtained in the same manner as in Example B-30 except that as the cationic lipid, cationic lipid 4 of Example A-4 was used instead of cationic lipid 1.

Comparative Example B-5

A composition of Comparative Example B-5 was obtained in the same manner as in Example B-30 except that as the cationic lipid, ALN-319 described above was used instead of cationic lipid 1.

(Analysis of Compositions (7))

In the same manner as in analysis of compositions (1), the average particle diameter (pre-storage average particle diameter) of lipid complexes were measured for the compositions of Example B-30 to Example B-33 and Comparative Example B-5. The compositions were further stored in sealed vials at 4° C. and the average particle diameter (post-storage average particle diameter) of lipid complexes after 3 months and 6 months was measured. Table 7 shows the change in the average particle diameter (Z-average) of lipid complexes. In the table, the change (%) in the average particle diameter was calculated by post-storage average particle diameter (after 6 months)/pre-storage average particle diameter×100.
[Table 7]

TABLE 7

| | | Pre-storage | | After 3 months | | After 6 months | | |
|---|---|---|---|---|---|---|---|---|
| Composition | Cationic lipid | Average particle diameter (nm) | Polydispersion index | Average particle diameter (nm) | Polydispersion index | Average particle diameter (nm) | Polydispersion index | Change in average particle diameter (%) |
| Example B-30 | 1 | 87 | 0.11 | 88 | 0.09 | 91 | 0.12 | 105 |
| Example B-31 | 2 | 78 | 0.09 | 80 | 0.12 | 85 | 0.14 | 109 |
| Example B-32 | 3 | 77 | 0.10 | 79 | 0.12 | 83 | 0.12 | 108 |
| Example B-33 | 4 | 86 | 0.11 | 85 | 0.11 | 87 | 0.08 | 101 |
| Comparative Example B-5 | ALN-319 | 84 | 0.11 | 102 | 0.10 | 117 | 0.09 | 139 |

It was demonstrated that the compositions of Example B-30 to Example B-33 had average particle diameters that hardly changed after a storage of 6 months and were physically more stable than the composition of Comparative Example B-5.

Preparation of Compositions (8)

Example B-34

A composition was prepared with cationic lipid 2 of Example A-2. As the nucleic acid, EPO mRNA was used.
EPO mRNA was dissolved in 10 mM sodium citrate (pH 4.0) at 80 µg/mL to obtain a diluted mRNA solution. Cationic lipid 2, DOPE (NOF Corporation), Cholesterol (Nippon Fine Chemical Co., Ltd.), MPEG2000-DMG (NOF Corporation) were dissolved in ethanol at a ratio of 60/5.0/33.5/1.5 (molar ratio) so that the total lipid concentration was set to 2.25 mM, and then a lipid solution was obtained. The diluted mRNA solution and the lipid solution were fed and mixed at flow rates of 3 mL/min and 1 mL/min, respectively, to obtain a lipid complex aqueous solution. The obtained lipid complex aqueous solution was subjected to dialysis using a dialysis membrane (product name "Float-A-Lyzer G2", SPECTRUM, Inc., 50K MWCO) to replace the external solution with phosphate buffer (PBS, pH 7.4). After the dialysis, concentration and filter sterilization were performed, thereby obtaining a composition of Example B-34.

Example B-35

A composition of Example B-35 was obtained in the same manner as in preparation of compositions (1) except that as the nucleic acid, Luciferase siRNA was used instead of Factor VII siRNA and as the cationic lipid, cationic lipid 2 of Example A-2 was used instead of cationic lipid 1. Luciferase siRNA was annealed siRNA (GeneDesign Inc.) that consists of a sense strand having a base sequence: 5'-CUUACGCUGAGUACUUCGAT*T-3' (T: DNA, *=Phosphorothioate linkage) (SEQ ID NO: 3) and an antisense strand having a base sequence: 5'-UCGAAGUACUCAGCGUAAGT*T-3' (T: DNA, *=Phosphorothioate linkage) (SEQ ID NO: 4).
(Analysis of Compositions (8))
In the same manner as in analysis of compositions (1), the encapsulation rate of mRNA or siRNA in lipid complexes and the average particle diameter of lipid complexes were measured for the compositions of Example B-34 and Example B-35. Table 8 shows the encapsulation rate of mRNA or siRNA and the average particle diameter (Z-average) of lipid complexes.

[Table 8]

TABLE 8

| Composition | Nucleic acid | Encapsulation rate (%) | Average particle diameter (nm) | Polydispersion index |
|---|---|---|---|---|
| Example B-34 | EPO mRNA | 98 | 105 | 0.06 |
| Example B-35 | Luciferase siRNA | 99 | 66 | 0.06 |

It is confirmed that the compositions of Example B-34 and Example B-35 exhibit high encapsulation rates of nucleic acid. This result indicates that the compositions of Examples may be used for nucleic acid delivery regardless of the type of nucleic acids.

C. Test Examples

Test Example 1

The compositions of Example B-1 to Example B-3 and Comparative Example B-1 were diluted with PBS so that the Factor VII siRNA concentration encapsulated in lipid complexes was 1 µg/mL or 5 µg/mL. The compositions were administered to ICR mice (5 weeks old, female, average weight: 25 g, n=3) via the tail vein at a dosage of 10 mL/kg, and the blood and liver were collected under anesthesia 24 hours after administration. The plasma was separated from the blood by centrifugation and the Factor VII protein concentration in the plasma was assayed using a commercially available kit (product name "BIOPHEN FVII", HYPHEN BioMed). As a negative control, the same treatment was carried out in a group to which PBS was administered.
When setting the Factor VII protein concentration of the group to which PBS was administered to 100%, the Factor VII protein concentrations of the groups to which the compositions were administered were calculated as a relative value. The results are shown in FIG. 1 and Table 9.
[Table 9]

TABLE 9

| siRNA dose (mg/kg) | Composition | Cationic lipid | Factor VII protein concentration (relative value) |
|---|---|---|---|
| 0.01 | Example B-1 | 1 | 50% |
| | Example B-2 | 2 | 46% |

TABLE 9-continued

| siRNA dose (mg/kg) | Composition | Cationic lipid | Factor VII protein concentration (relative value) |
|---|---|---|---|
| | Example B-3 | 3 | 44% |
| | Comparative Example B-1 | ALN-319 | 63% |
| 0.05 | Example B-1 | 1 | 13% |
| | Example B-2 | 2 | 12% |
| | Example B-3 | 3 | 11% |
| | Comparative Example B-1 | ALN-319 | 21% |

It is confirmed that the compositions of Example B-1 to Example B-3 have a higher inhibitory effect on Factor VII protein expression than the composition of Comparative Example B-1. This result indicates that the compositions of Examples effectively release nucleic acids into the cytoplasm.

Test Example 2

In the same manner as in Test Example 1, the compositions of Example B-4 and Comparative Example B-1 were administered to ICR mice (5 weeks old, female, average weight: 25 g, n=3) and the relative value of Factor VII protein concentration in the plasma 24 hours after administration was calculated. The results are shown in FIG. 2 and Table 10.
[Table 10]

TABLE 10

| siRNA dose (mg/kg) | Composition | Cationic lipid | Factor VII protein concentration (relative value) |
|---|---|---|---|
| 0.01 | Example B-4 | 4 | 68% |
| | Comparative Example B-1 | ALN-319 | 77% |
| 0.05 | Example B-4 | 4 | 18% |
| | Comparative Example B-1 | ALN-319 | 24% |

It is confirmed that the composition of Example B-4 has a higher inhibitory effect on Factor VII protein expression than the composition of Comparative Example B-1. This result indicates that the compositions of Examples effectively release nucleic acids into the cytoplasm.

Test Example 3

In the same manner as in Test Example 1, the composition of Example B-5 was administered to ICR mice (5 weeks old, female, average weight: 25 g, n=3) and the relative value of Factor VII protein concentration in the plasma 24 hours after administration was calculated. The results are shown in Table 11.
[Table 11]

TABLE 11

| siRNA dose (mg/kg) | Composition | Cationic lipid | Factor VII protein concentration (relative value) |
|---|---|---|---|
| 0.01 | Example B-5 | 5 | 77% |
| 0.05 | Example B-5 | 5 | 14% |

It is confirmed that the composition of Example B-5 has a high inhibitory effect on Factor VII protein expression. This result indicates that the compositions of Examples effectively release nucleic acids into the cytoplasm.

Test Example 4

The compositions of Example B-11 and Comparative Example B-3 were diluted with PBS so that the hEPO mRNA concentration encapsulated in lipid complexes was 1 µg/mL or 3 µg/mL. The compositions were administered to ICR mice (5 weeks old, female, average weight: 25 g, n=3) via the tail vein at a dosage of 10 mL/kg, and the blood was collected under anesthesia 24 hours after administration. The plasma was separated from the blood by centrifugation and the hEPO protein concentration in the plasma was assayed using a commercially available kit (product name "Human Erythropoietin Quantikine IVD ELISA Kit", R&D Systems). As a negative control, the same treatment was carried out in a group of mice without administration (no treatment) and a group of mice to which PBS was administered. The results are shown in Table 12.
[Table 12]

TABLE 12

| mRNA dose (mg/kg) | Composition | Cationic lipid | hEPO protein concentration (pg/mL) |
|---|---|---|---|
| No treatment | | | Not detected |
| PBS administration | | | Not detected |
| 0.01 | Example B-11 | 2 | 29.7 |
| 0.03 | Example B-11 | 2 | 234.1 |
| | Comparative Example B-3 | ALN-319 | 165.4 |

It is confirmed that the composition of Example B-11 has a higher effect of hEPO protein expression than the composition of Comparative Example B-3. This result indicates that the compositions of Examples effectively release nucleic acids into the cytoplasm.

Test Example 5

The compositions of Example B-14 to Example B-21 were diluted with PBS so that the Factor VII siRNA concentration encapsulated in lipid complexes was 3 µg/mL or 30 µg/mL. The compositions were administered to ICR mice (5 weeks old, female, average weight: 25 g, n=3) via the tail vein at a dosage of 10 mL/kg, and the blood and liver were collected under anesthesia 24 hours after administration. The plasma was separated from the blood by centrifugation and the Factor VII protein concentration in the plasma was assayed using a commercially available kit (product name "BIOPHEN FVII", HYPHEN BioMed). As a negative control, the same treatment was carried out in a group to which PBS was administered.

When the Factor VII protein concentration of the group to which PBS was administered was set to 100%, the Factor VII protein concentrations of the groups to which the compositions were administered were calculated as a relative value. The results are shown in Table 13.

[Table 13]

TABLE 13

| siRNA dose (mg/kg) | Composition | Cationic lipid | Factor VII protein concentration (relative value) |
|---|---|---|---|
| 0.03 | Example B-14 | 9 | 38% |
|  | Example B-15 | 10 | 69% |
|  | Example B-16 | 11 | 71% |
|  | Example B-17 | 12 | 52% |
|  | Example B-18 | 13 | 93% |
|  | Example B-19 | 14 | 88% |
|  | Example B-20 | 15 | 44% |
|  | Example B-21 | 2 | 45% |
| 0.3 | Example B-14 | 9 | 7% |
|  | Example B-15 | 10 | 15% |
|  | Example B-16 | 11 | 19% |
|  | Example B-17 | 12 | 3% |
|  | Example B-18 | 13 | 93% |
|  | Example B-19 | 14 | 57% |
|  | Example B-20 | 15 | 2% |
|  | Example B-21 | 2 | 2% |

Test Example 6

In the same manner as in Test Example 5, the compositions of Example B-22 to Example B-29 were administered to ICR mice (5 weeks old, female, average weight: 25 g, n=3) and the relative value of Factor VII protein concentration in the plasma 24 hours after administration was calculated. The results are shown in Table 14.

[Table 14]

TABLE 14

| siRNA dose (mg/kg) | Composition | Cationic lipid | Factor VII protein concentration (relative value) |
|---|---|---|---|
| 0.03 | Example B-22 | 16 | 45% |
|  | Example B-23 | 17 | 51% |
|  | Example B-24 | 18 | 101% |
|  | Example B-25 | 19 | 53% |
|  | Example B-26 | 20 | 18% |
|  | Example B-27 | 21 | 62% |
|  | Example B-28 | 22 | 59% |
|  | Example B-29 | 2 | 20% |
| 0.3 | Example B-22 | 16 | 6% |
|  | Example B-23 | 17 | 4% |
|  | Example B-24 | 18 | 83% |
|  | Example B-25 | 19 | 4% |
|  | Example B-26 | 20 | <1% |
|  | Example B-27 | 21 | 23% |
|  | Example B-28 | 22 | <1% |
|  | Example B-29 | 2 | 1% |

Test Example 7

The composition of Example B-34 encapsulating EPO mRNA was diluted with PBS so that the RNA concentration encapsulated in the lipid complex was 30 μg/mL. The compositions were administered to BALB/c mice (female, n=4) via the tail vein at a dosage of 10 mL/kg, and the blood was collected under anesthesia 1 day and 4 days after administration. The plasma was separated from the blood by centrifugation and the hEPO protein concentration in the plasma was assayed using a commercially available kit (product name "Human Erythropoietin Quantikine IVD ELISA Kit", R&D Systems). The number of reticulocytes was also measured. As negative controls, the same treatment was carried out in a group of mice without administration (no treatment) and a group of mice to which the composition of Example B-35 encapsulating Luciferase siRNA was administered. The results are shown in Table 15.

[Table 15]

TABLE 15

| Administered sample | Composition | Nucleic acid dose (mg/kg) | Day(s) after administration | hEPO concentration (pg/mL) (Ave ± S.D.) | Number of reticulocytes ($10^9$/L) (Ave ± S.D.) |
|---|---|---|---|---|---|
| No treatment | — | — | — | Not detected | 435 ± 57 |
| Luc siRNA | Example B-35 | 0.30 | 1 day | Not detected | 404 ± 74 |
| EPO mRNA | Example B-34 | 0.30 | 1 day | 3175 ± 379 | 310 ± 25 |
| Luc siRNA | Example B-35 | 0.30 | 4 days | Not detected | 330 ± 101 |
| EPO mRNA | Example B-34 | 0.30 | 4 days | Not detected | 615 ± 60 |

In the no treatment group and the Luc siRNA administration group, hEPO was not detected, while in the EPO mRNA administration group, hEPO was detected 1 day after administration. It was also confirmed that due to the action of generated EPO, the number of reticulocytes increased 4 days after administration. This result indicates that the compositions of Examples effectively release nucleic acids into the cytoplasm.

From the above results, according to the cationic lipid of the present invention, it is possible to release effectively nucleic acids into the cytoplasm. In addition, according to the cationic lipid of the present invention, it is possible to suppress an increase in the particle diameter of lipid complexes after a storage over a certain period of time.

INDUSTRIAL APPLICABILITY

According to the present invention, it is possible to provide a cationic lipid that can effectively release nucleic acids into the cytoplasm.

The invention claimed is:

1. A compound represented by formula (1a) below or a pharmaceutically acceptable salt thereof:

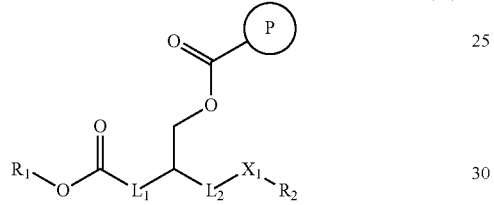
(1a)

wherein $L_1$ and $L_2$ independently represent an alkylene group having 3 to 10 carbon atoms; $R_1$ and $R_2$ independently represent an alkyl group having 4 to 22 carbon atoms or an alkenyl group having 4 to 22 carbon atoms; $X_1$ represents a single bond or —CO—O—; and the ring P represents any of formulae (P-1) to (P-5) below:

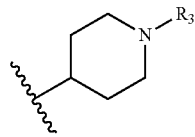
(P-1)

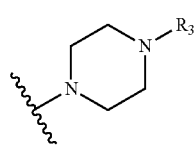
(P-2)

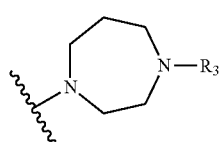
(P-3)

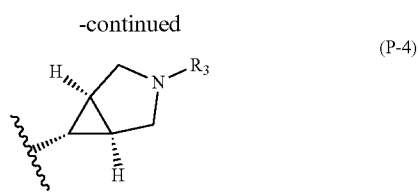
(P-4)

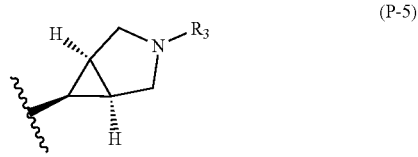
(P-5)

wherein $R_3$ represents an alkyl group having 1 to 3 carbon atoms.

2. The compound according to claim 1 represented by formula (1) or a pharmaceutically acceptable salt thereof:

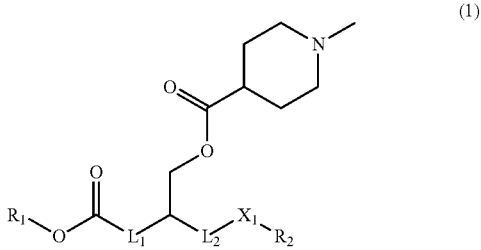
(1)

wherein $L_1$ and $L_2$ independently represent an alkylene group having 3 to 10 carbon atoms; $R_1$ and $R_2$ independently represent an alkyl group having 4 to 22 carbon atoms or an alkenyl group having 4 to 22 carbon atoms; and $X_1$ represents a single bond or —CO—O—.

3. The compound according to claim 1, selected from the group consisting of compounds represented by formulae (A1) to (A22) below, or a pharmaceutically acceptable salt thereof:

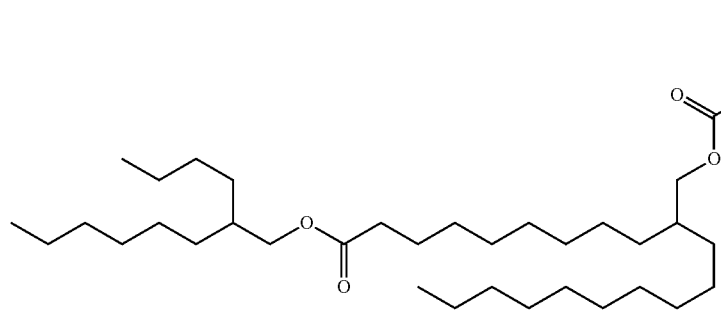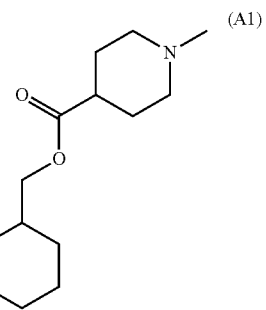
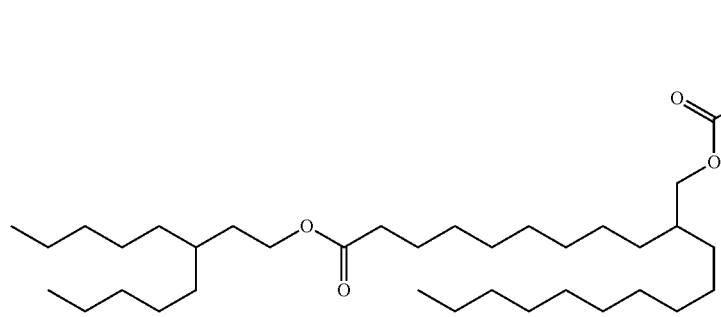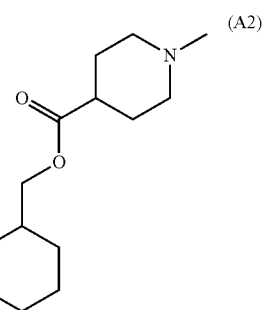
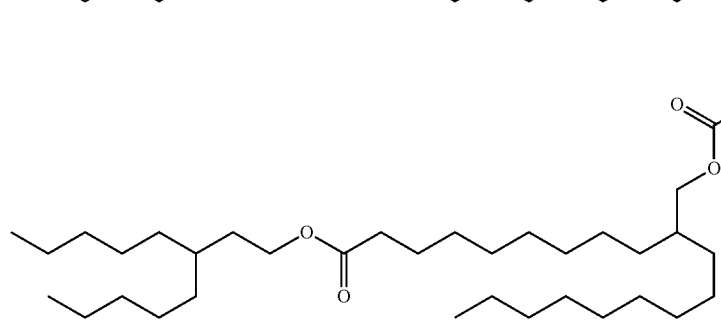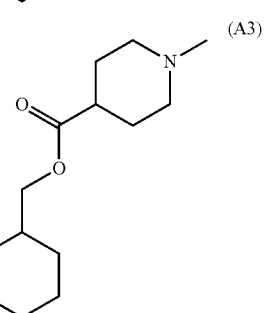
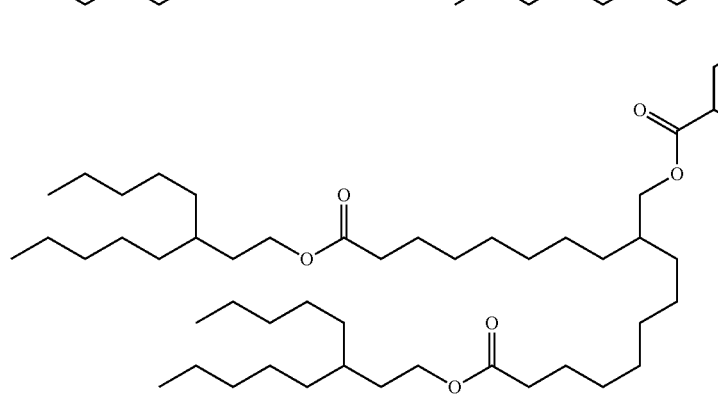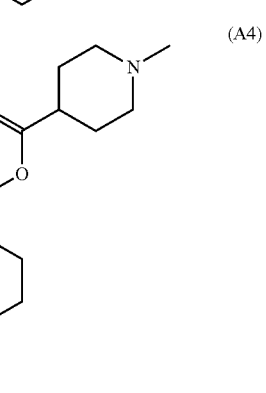
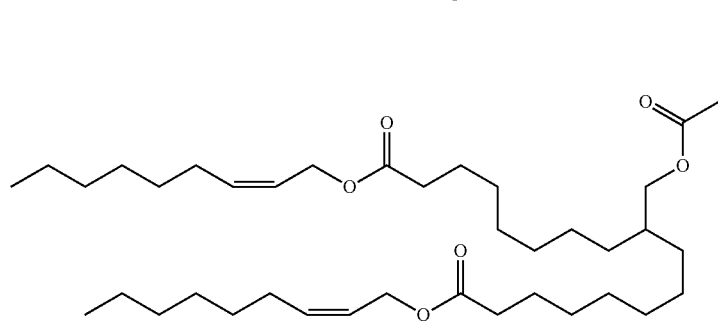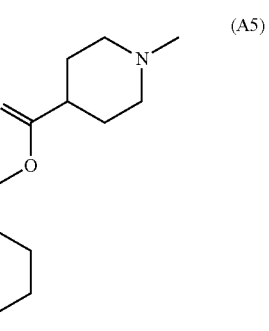

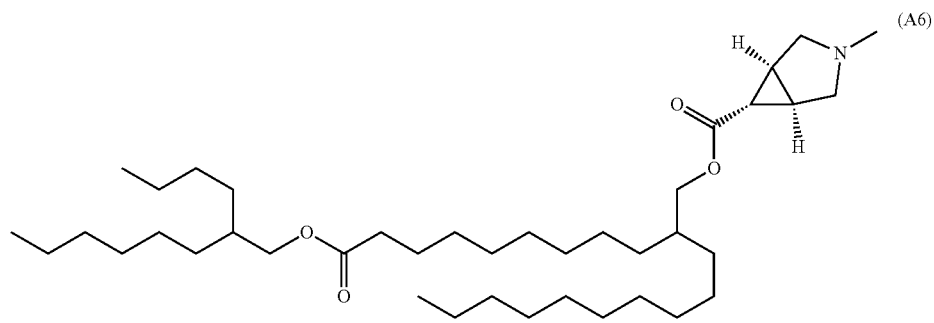
(A6)
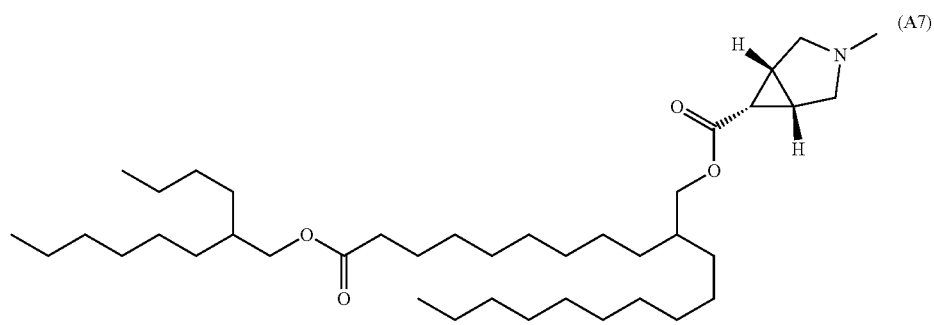
(A7)
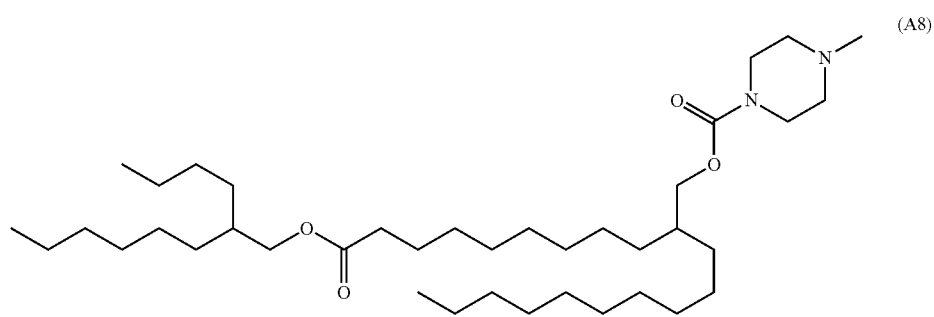
(A8)
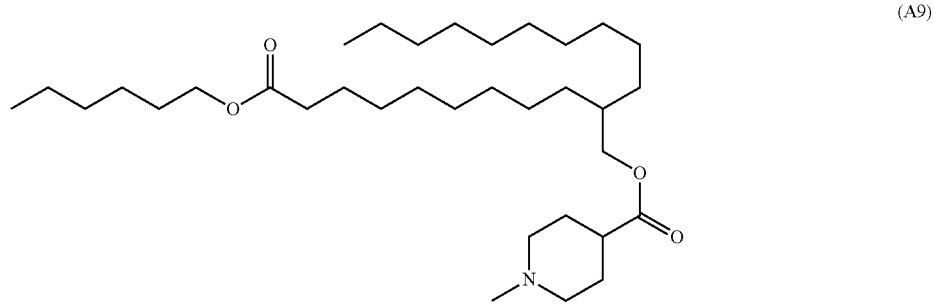
(A9)
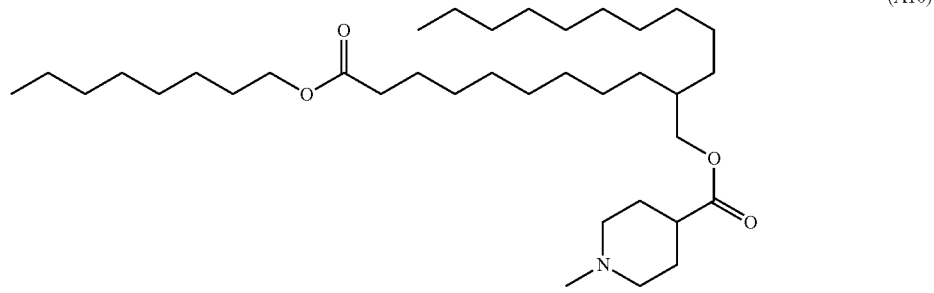
(A10)

-continued
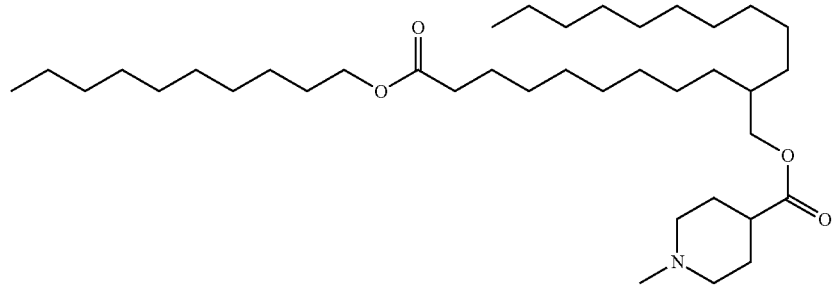
(A11)
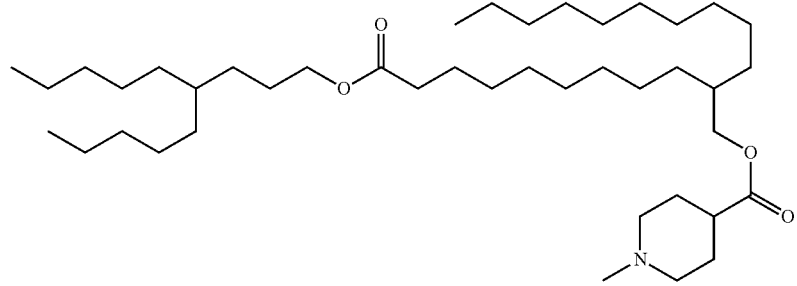
(A12)
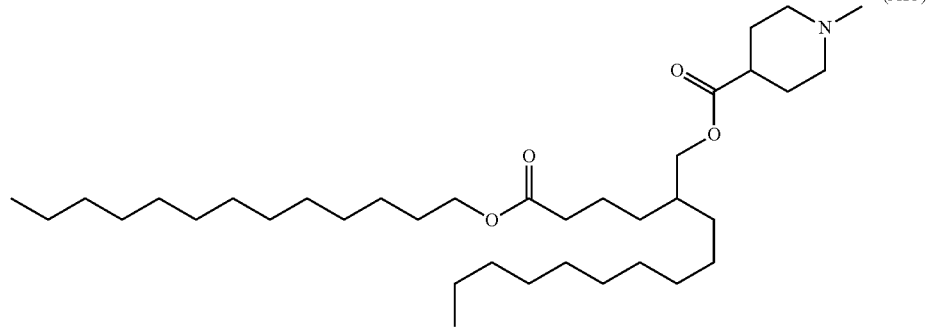
(A13)
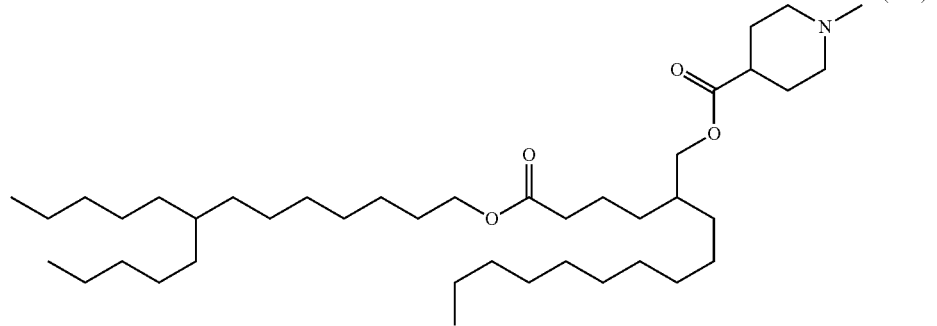
(A14)
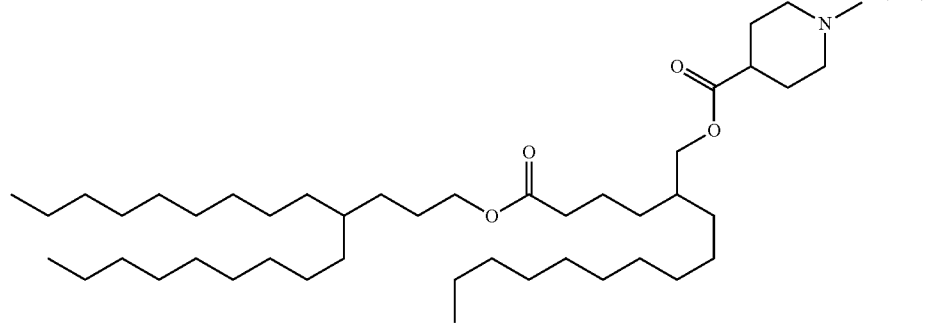
(A15)

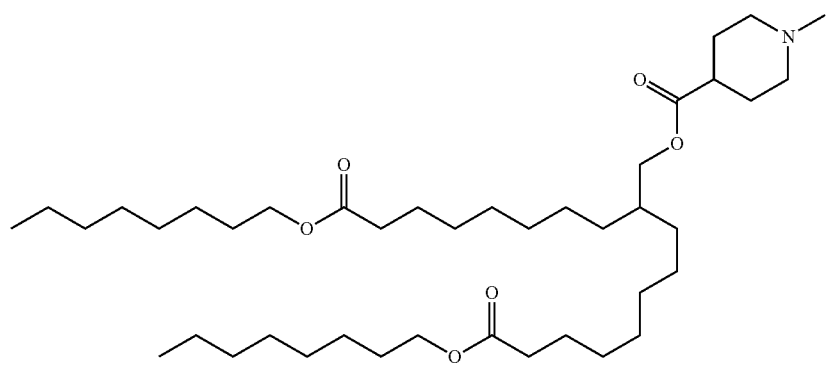
(A16)
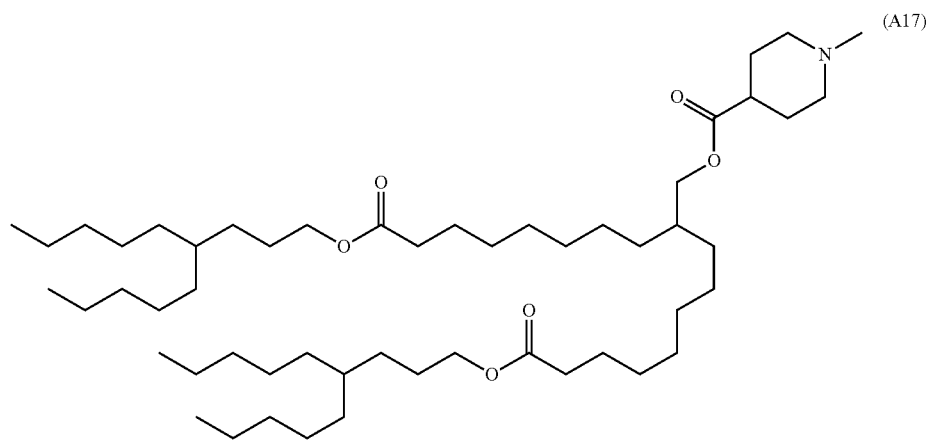
(A17)
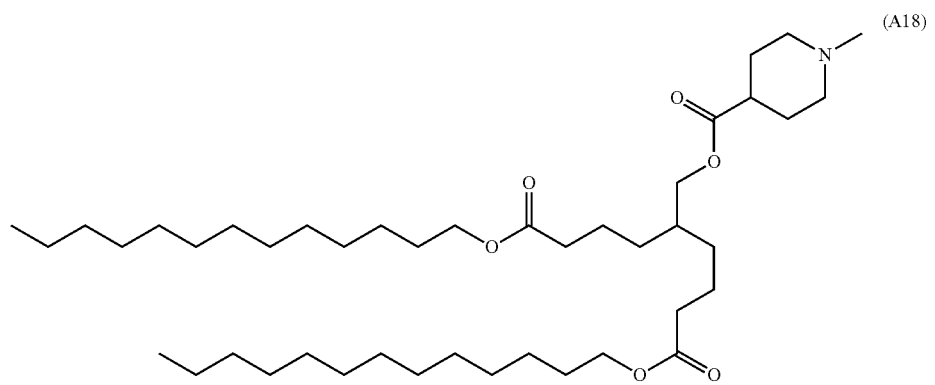
(A18)
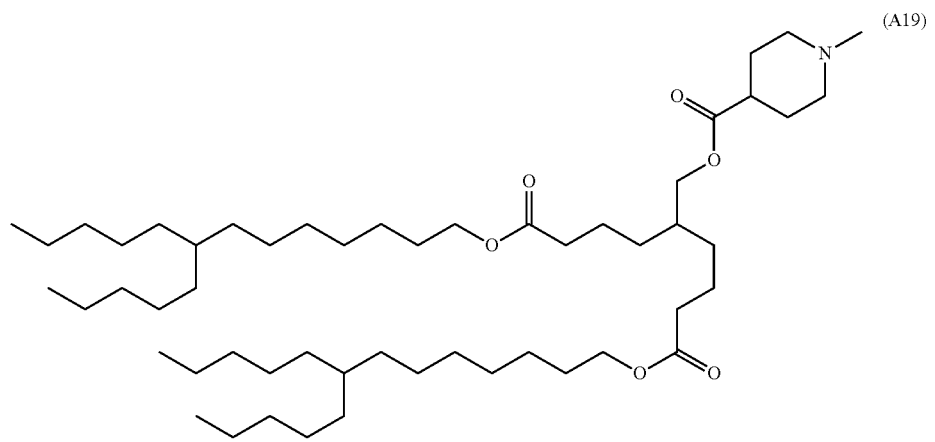
(A19)

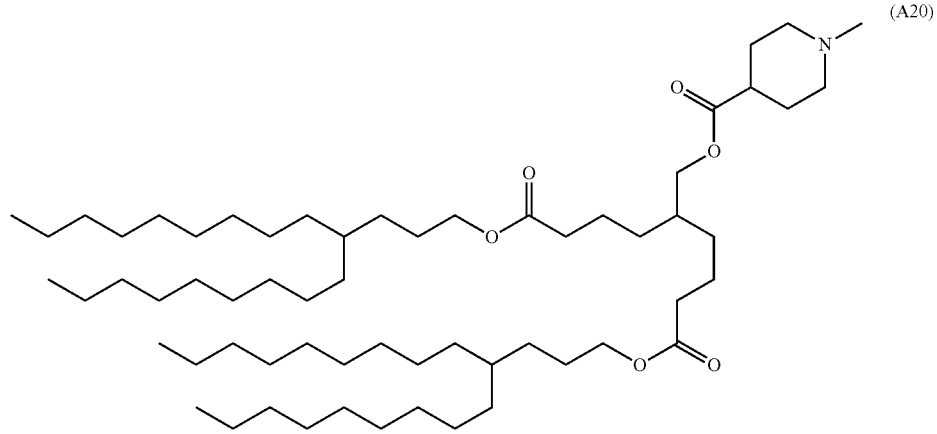
(A20)
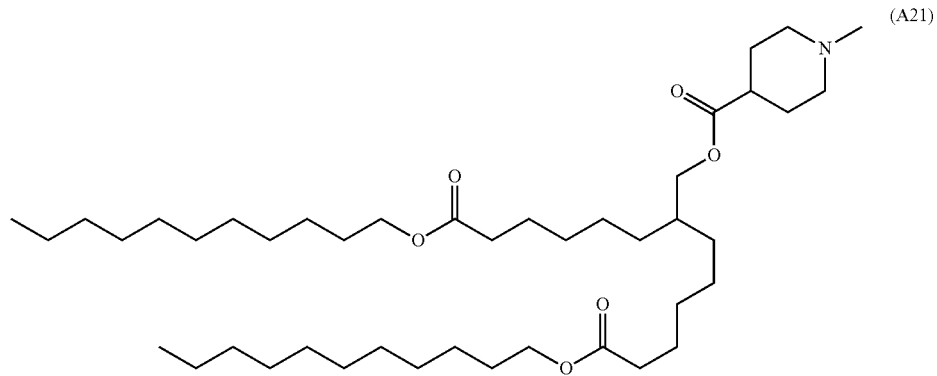
(A21)
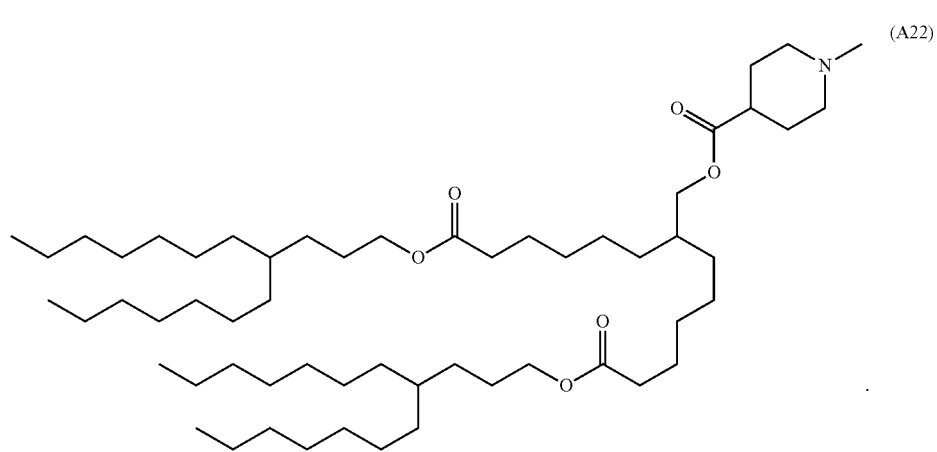
(A22)

4. The compound according to claim 1 represented by formula (A1) below, or a pharmaceutically acceptable salt thereof:

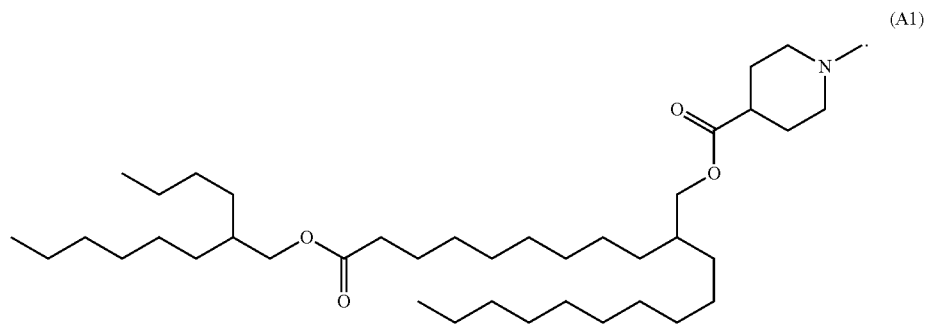 [SMILES: CCCCCCCCCCC(CCCCCCCCC(=O)OCC(CCCC)CCCCCC)COC(=O)C1CCN(C)CC1]
(A1)

5. The compound according to claim 1, represented by formula (A2) below, or a pharmaceutically acceptable salt thereof:

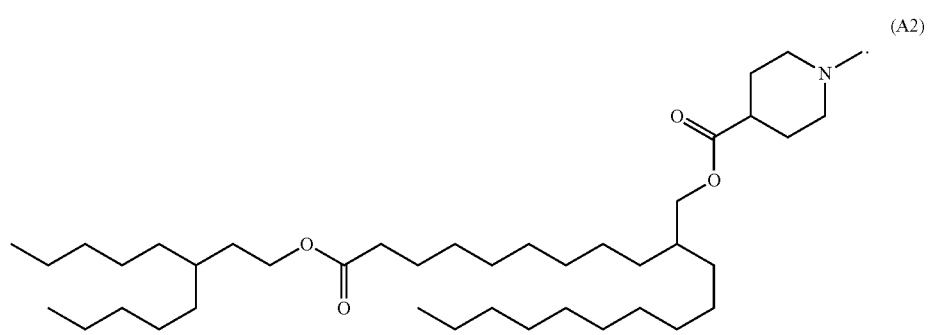
(A2)

6. The compound according to claim 1 represented by formula (A3) below, or a pharmaceutically acceptable salt thereof:

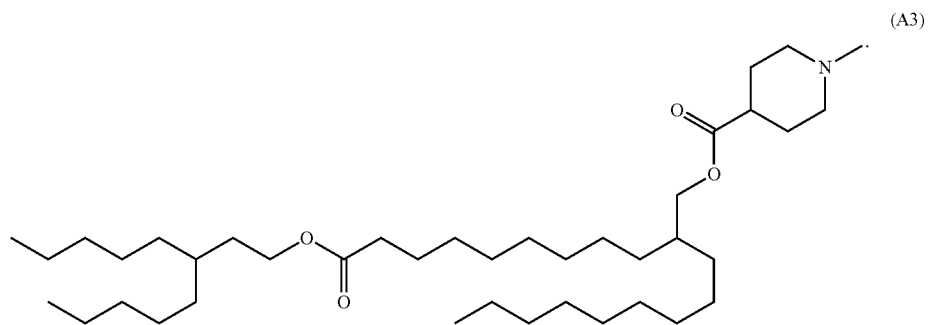 [SMILES: CCCCCCCCCC(CCCCCCCCC(=O)OCCC(CCCCC)CCCCC)COC(=O)C1CCN(C)CC1]
(A3)

7. The compound according to claim 1, represented by formula (A4) below, or a pharmaceutically acceptable salt thereof:

(A4)
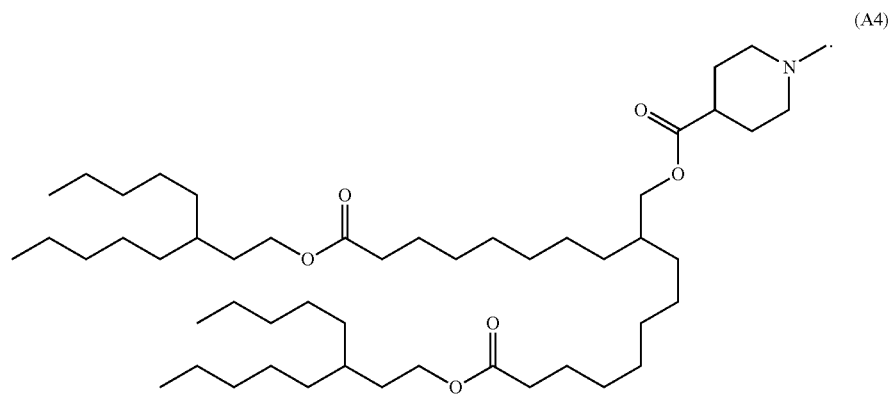 [SMILES: CCCCCC(CCCCC)CCOC(=O)CCCCCCCC(CCCCCCCC(=O)OCCC(CCCCC)CCCCC)COC(=O)C1CCN(C)CC1]
8. The compound according to claim 1, represented by formula (A5) below, or a pharmaceutically acceptable salt thereof:
(A5)
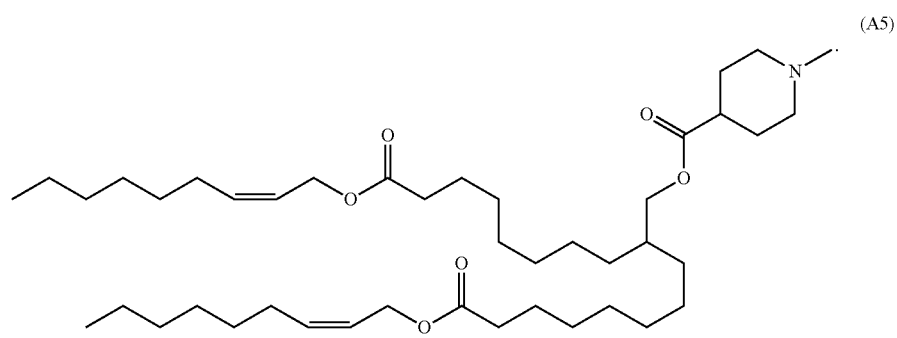 [SMILES: CCCCCC/C=C\COC(=O)CCCCCCCC(CCCCCCCC(=O)OC/C=C\CCCCCC)COC(=O)C1CCN(C)CC1]
9. The compound according to claim 1, represented by formula (A9) below, or a pharmaceutically acceptable salt thereof:
(A9)
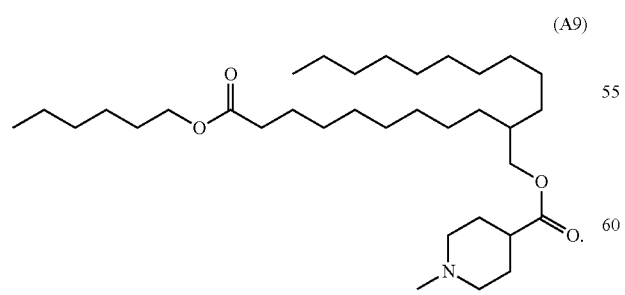
10. The compound according to claim 1, represented by formula (A12) below, or a pharmaceutically acceptable salt thereof:

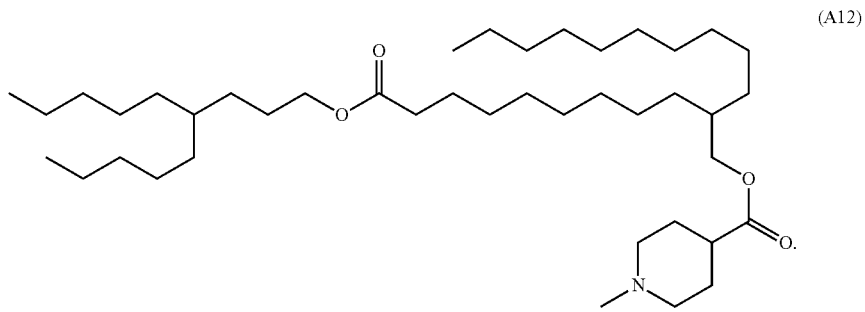 [SMILES: CCCCCCCCCCC(CCCCCCCCC(=O)OCCCC(CCCCC)CCCCC)COC(=O)C1CCN(C)CC1]

(A12)

11. The compound according to claim 1, represented by formula (A15) below, or a pharmaceutically acceptable salt thereof:

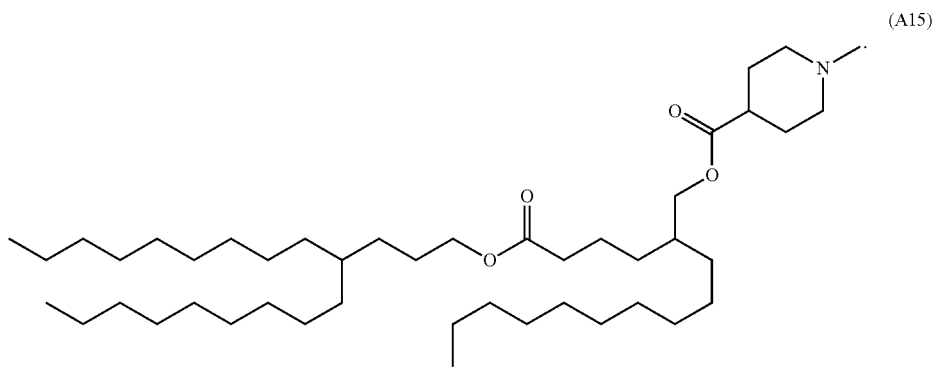 [SMILES: CCCCCCCCCCC(CCCC(=O)OCCCC(CCCCCCCCC)CCCCCCCCC)COC(=O)C1CCN(C)CC1]

(A15)

12. The compound according to claim 1, represented by formula (A20) below, or a pharmaceutically acceptable salt thereof:

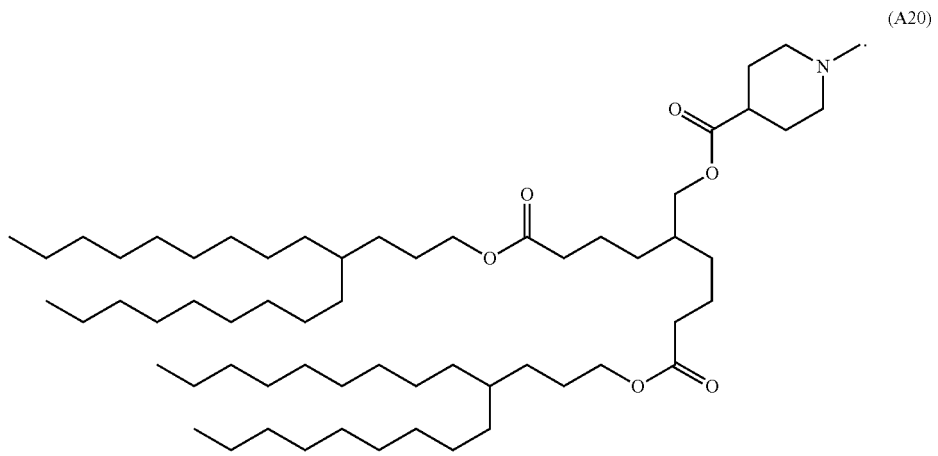 [SMILES: CCCCCCCCCC(CCCCCCCCC)CCCOC(=O)CCCC(CCCC(=O)OCCCC(CCCCCCCCC)CCCCCCCCC)COC(=O)C1CCN(C)CC1]

(A20)

13. A lipid complex comprising:

(I) the compound according to claim 1 or a pharmaceutically acceptable salt thereof; and (II) at least one lipid selected from the group consisting of a neutral lipid, a polyethylene glycol-modified lipid and a sterol.

14. A composition comprising:

(I) the compound according to claim 1 or a pharmaceutically acceptable salt thereof;

(II) at least one lipid selected from the group consisting of a neutral lipid, a polyethylene glycol-modified lipid and a sterol; and (III) a nucleic acid.

15. A method for producing a composition, the method comprising:

the step of mixing a polar organic solvent-containing aqueous solution containing (I) the compound according to claim 1 or a pharmaceutically acceptable salt thereof, and (II) at least one lipid selected from the group consisting of a neutral lipid, a polyethylene glycol-modified lipid and a sterol with an aqueous solution containing (III) a nucleic acid to obtain a mixed solution; and the step of reducing a content percentage of the polar organic solvent in the mixed solution.

\* \* \* \* \*